(12) United States Patent
Dumas et al.

(10) Patent No.: US 8,618,141 B2
(45) Date of Patent: Dec. 31, 2013

(54) ARYL UREAS WITH ANGIOGENESIS INHIBITING ACTIVITY

(75) Inventors: Jacques Dumas, Bethany, CT (US); William J. Scott, Guilford, CT (US); James Elting, Madison, CT (US); Holia Hatoum-Makdad, Hamden, CT (US)

(73) Assignee: Bayer Healthcare LLC, Whippany, NJ (US)

( * ) Notice: Subject to any disclaimer, the term of this patent is extended or adjusted under 35 U.S.C. 154(b) by 0 days.

(21) Appl. No.: 13/551,884

(22) Filed: Jul. 18, 2012

(65) Prior Publication Data

US 2012/0289552 A1 Nov. 15, 2012

Related U.S. Application Data

(63) Continuation of application No. 12/888,887, filed on Sep. 23, 2010, now Pat. No. 8,242,147, which is a continuation of application No. 10/361,858, filed on Feb. 11, 2003, now Pat. No. 7,838,541.

(60) Provisional application No. 60/354,950, filed on Feb. 11, 2002.

(51) Int. Cl.
*A61K 31/44* (2006.01)
*C07D 213/30* (2006.01)

(52) U.S. Cl.
USPC ............................... 514/346; 546/291

(58) Field of Classification Search
None
See application file for complete search history.

(56) References Cited

U.S. PATENT DOCUMENTS

| | | |
|---|---|---|
| 502,504 A | 8/1893 | Thoms |
| 1,792,156 A | 2/1931 | Fitzky |
| 2,046,375 A | 7/1936 | Goldstein et al. |
| 2,093,265 A | 9/1937 | Coffey et al. |
| 2,288,422 A | 6/1942 | Rohm |
| 2,649,476 A | 8/1953 | Martin |
| 2,683,082 A | 7/1954 | Hill et al. |
| 2,722,544 A | 11/1955 | Martin |
| 2,745,874 A | 5/1956 | Schetty et al. |
| 2,781,330 A | 2/1957 | Downey |
| 2,797,214 A | 6/1957 | Bossard |
| 2,867,659 A | 1/1959 | Model et al. |
| 2,877,268 A | 3/1959 | Applegath et al. |
| 2,960,488 A | 11/1960 | Tamblyn et al. |
| 2,973,386 A | 2/1961 | Weldon |
| 3,151,023 A | 9/1964 | Martin |
| 3,177,110 A | 4/1965 | Ogait |
| 3,200,035 A | 8/1965 | Martin et al. |
| 3,230,141 A | 1/1966 | Frick et al. |
| 3,284,433 A | 11/1966 | Becker et al. |
| 3,424,760 A | 1/1969 | Helsley et al. |
| 3,424,761 A | 1/1969 | Helsley et al. |
| 3,424,762 A | 1/1969 | Helsley |
| 3,547,940 A | 12/1970 | Brantley |
| 3,639,668 A | 2/1972 | Alles et al. |
| 3,646,059 A | 2/1972 | Brantley |
| 3,668,222 A | 6/1972 | Hauser |
| 3,689,550 A | 9/1972 | Schellenbaum et al. |
| 3,743,498 A | 7/1973 | Brantley |
| 3,754,887 A | 8/1973 | Brantley |
| 3,823,161 A | 7/1974 | Lesser |
| 3,828,001 A | 8/1974 | Broad et al. |
| 3,860,645 A | 1/1975 | Nikawitz |
| 3,990,879 A | 11/1976 | Soper |
| 4,001,256 A | 1/1977 | Callahan et al. |
| 4,009,847 A | 3/1977 | Aldrich et al. |
| 4,042,372 A | 8/1977 | Harper |
| 4,062,861 A | 12/1977 | Yukinaga et al. |
| 4,063,928 A | 12/1977 | Johnston |
| 4,071,524 A | 1/1978 | Banitt |
| 4,103,022 A | 7/1978 | Sirrenberg et al. |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |
| 4,240,820 A | 12/1980 | Dickore et al. |
| 4,279,639 A | 7/1981 | Okamoto et al. |
| 4,293,328 A | 10/1981 | Yukinaga et al. |
| 4,358,596 A | 11/1982 | Krüger |
| 4,405,644 A | 9/1983 | Kabbe et al. |
| 4,410,697 A | 10/1983 | Török et al. |
| 4,437,878 A | 3/1984 | Acker et al. |
| 4,468,380 A | 8/1984 | O'Doherty et al. |

(Continued)

FOREIGN PATENT DOCUMENTS

| | | |
|---|---|---|
| AU | 5721786 A1 | 11/1986 |
| AU | 3163389 A1 | 9/1989 |

(Continued)

OTHER PUBLICATIONS

Adjei et al., "A Phase 1 study of BAY 43-9006 and gefitinib in patients with refractory or recurrent non-small-cell lung cancer (NSCLC)," Abstract #3067. Meeting: *2005 ASCO Annual Meeting*, Category: Developmental Therapeutics: Molecular Therapeutics, Subcategory: Antiangiogenic or Antimetastatic agents.

Ahmad et al., "Kinase Inhibition with BAY 43-9006 in Renal Cell Carcinoma," *Clinical Cancer Research*, Sep. 15, 2004, vol. 10(suppl,), pp. 6388s-6392s.

Amornphimoltham et al., "Persistent Activation of the Akt Pathway in Head and Neck Squamous Cell Carcinoma: A Potential Target for UCN-01," Clinical Cancer Research, vol. 10, Jun. 15, 2004, pp. 4029-4037.

Arzneimitteltherapie, "Sorafenib" Oct. 6, 2006, Auflage 18498, 7 pages.

Arnone et al., "Selectivities in the Oxidation of Tertiary Amines and Pyridine Derivatives Perfluoro *Cis* -2,3-dialkyloxaziridines," Tetrahedron, vol. 54, 1998, pp. 7831-7842.

(Continued)

*Primary Examiner* — Zinna Northington Davis
(74) *Attorney, Agent, or Firm* — Millen, White, Zelano & Branigan, P.C.

(57) ABSTRACT

This invention relates to methods of using aryl ureas to treat diseases mediated by the VEGF induced signal transduction pathway characterized by abnormal angiogenesis or hyperpermeability processes.

11 Claims, No Drawings

(56) References Cited

U.S. PATENT DOCUMENTS

| | | |
|---|---|---|
| 4,473,579 A | 9/1984 | Devries et al. |
| 4,499,097 A | 2/1985 | Tomcufcik et al. |
| 4,511,571 A | 4/1985 | Böger et al. |
| 4,514,571 A | 4/1985 | Nakai et al. |
| 4,526,997 A | 7/1985 | O'Doherty et al. |
| 4,540,566 A | 9/1985 | Davis et al. |
| 4,546,191 A | 10/1985 | Nishiyama et al. |
| 4,587,240 A | 5/1986 | Hider et al. |
| 4,623,662 A | 11/1986 | De Vries |
| 4,643,849 A | 2/1987 | Hirai et al. |
| 4,740,520 A | 4/1988 | Hallenbach et al. |
| 4,760,063 A | 7/1988 | Hallenbach et al. |
| 4,775,763 A | 10/1988 | Dalton et al. |
| 4,808,588 A | 2/1989 | King |
| 4,820,871 A | 4/1989 | Kissener et al. |
| 4,863,924 A | 9/1989 | Haga et al. |
| 4,921,525 A | 5/1990 | Grossman et al. |
| 4,973,675 A | 11/1990 | Israel et al. |
| 4,977,169 A | 12/1990 | Häusermann et al. |
| 4,983,605 A | 1/1991 | Kondo et al. |
| 4,985,449 A | 1/1991 | Haga et al. |
| 4,996,325 A | 2/1991 | Kristinsson |
| 5,036,072 A | 7/1991 | Nakajima et al. |
| 5,059,614 A | 10/1991 | Lepage et al. |
| 5,063,247 A | 11/1991 | Sekiya et al. |
| 5,098,907 A | 3/1992 | Kondo et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,331 A | 7/1992 | Pascual |
| 5,151,344 A | 9/1992 | Abe et al. |
| 5,151,413 A | 9/1992 | Caufield et al. |
| 5,162,360 A | 11/1992 | Creswell et al. |
| 5,177,110 A | 1/1993 | Oechslein et al. |
| 5,185,358 A | 2/1993 | Creswell et al. |
| 5,256,790 A | 10/1993 | Nelson |
| 5,258,389 A | 11/1993 | Goulet et al. |
| 5,270,458 A | 12/1993 | Lemischka |
| 5,283,354 A | 2/1994 | Lemischka |
| 5,297,159 A | 3/1994 | Dung et al. |
| 5,312,820 A | 5/1994 | Ashton et al. |
| 5,319,099 A | 6/1994 | Kamata et al. |
| 5,378,725 A | 1/1995 | Bonjouklian et al. |
| 5,399,566 A | 3/1995 | Katano et al. |
| 5,423,905 A | 6/1995 | Fringeli |
| 5,429,918 A | 7/1995 | Seto et al. |
| 5,432,468 A | 7/1995 | Moriyama et al. |
| 5,441,947 A | 8/1995 | Dodge et al. |
| 5,447,957 A | 9/1995 | Adams et al. |
| 5,456,920 A | 10/1995 | Matoba et al. |
| 5,468,773 A | 11/1995 | Dodge et al. |
| 5,470,882 A | 11/1995 | Dixon et al. |
| 5,480,906 A | 1/1996 | Creemer et al. |
| 5,500,424 A | 3/1996 | Nagamine et al. |
| 5,508,288 A | 4/1996 | Forbes et al. |
| 5,547,966 A | 8/1996 | Atwal et al. |
| 5,559,137 A | 9/1996 | Adams et al. |
| 5,596,001 A | 1/1997 | Hamanaka |
| 5,597,719 A | 1/1997 | Freed et al. |
| 5,624,937 A | 4/1997 | Reel et al. |
| 5,656,612 A | 8/1997 | Monia |
| 5,658,903 A | 8/1997 | Adams et al. |
| 5,667,226 A | 9/1997 | Janich |
| 5,696,138 A | 12/1997 | Olesen et al. |
| 5,698,581 A | 12/1997 | Kleemann et al. |
| 5,710,094 A | 1/1998 | Minami et al. |
| 5,721,237 A | 2/1998 | Myers et al. |
| 5,726,167 A | 3/1998 | Dodge et al. |
| 5,747,498 A | 5/1998 | Schnur et al. |
| 5,773,459 A | 6/1998 | Tang et al. |
| 5,777,097 A | 7/1998 | Lee et al. |
| 5,780,262 A | 7/1998 | Brent et al. |
| 5,780,483 A | 7/1998 | Widdowson et al. |
| 5,783,664 A | 7/1998 | Lee et al. |
| 5,786,362 A | 7/1998 | Krongrad |
| 5,801,794 A | 9/1998 | Lehureau et al. |
| 5,807,876 A | 9/1998 | Armistead et al. |
| 5,807,891 A | 9/1998 | Bold et al. |
| 5,808,080 A | 9/1998 | Bell et al. |
| 5,814,646 A | 9/1998 | Heinz et al. |
| 5,869,043 A | 2/1999 | McDonnell et al. |
| 5,871,934 A | 2/1999 | Lee et al. |
| 5,886,044 A | 3/1999 | Widdowson et al. |
| 5,891,895 A | 4/1999 | Shiraishi et al. |
| 5,908,865 A | 6/1999 | Doi et al. |
| 5,919,773 A | 7/1999 | Monia et al. |
| 5,929,250 A | 7/1999 | Widdowson et al. |
| 5,955,366 A | 9/1999 | Lee et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,017,692 A | 1/2000 | Brent et al. |
| 6,020,345 A | 2/2000 | Vacher et al. |
| 6,022,884 A | 2/2000 | Mantlo et al. |
| 6,025,151 A | 2/2000 | Peterson |
| 6,033,873 A | 3/2000 | McDonnell et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,103,692 A | 8/2000 | Avruch et al. |
| 6,114,517 A | 9/2000 | Monia et al. |
| 6,130,053 A | 10/2000 | Thompson et al. |
| 6,133,319 A | 10/2000 | Widdowson |
| 6,136,779 A | 10/2000 | Foulkes et al. |
| 6,143,764 A | 11/2000 | Kubo et al. |
| 6,147,107 A | 11/2000 | Dent et al. |
| 6,147,116 A | 11/2000 | Barbachyn et al. |
| 6,150,415 A | 11/2000 | Hammock et al. |
| 6,159,901 A | 12/2000 | Kanno et al. |
| 6,174,901 B1 | 1/2001 | Mantlo et al. |
| 6,177,401 B1 | 1/2001 | Ullrich et al. |
| 6,178,399 B1 | 1/2001 | Takebayashi et al. |
| 6,180,631 B1 | 1/2001 | McMahon et al. |
| 6,180,675 B1 | 1/2001 | Widdowson et al. |
| 6,187,799 B1 | 2/2001 | Wood et al. |
| 6,193,965 B1 | 2/2001 | Karin et al. |
| 6,204,267 B1 | 3/2001 | Tang et al. |
| 6,210,710 B1 | 4/2001 | Skinner |
| 6,211,373 B1 | 4/2001 | Widdowson et al. |
| 6,218,539 B1 | 4/2001 | Widdowson |
| 6,228,881 B1 | 5/2001 | Regan et al. |
| 6,235,764 B1 | 5/2001 | Larson et al. |
| 6,236,125 B1 | 5/2001 | Oudet et al. |
| 6,242,601 B1 | 6/2001 | Breu et al. |
| 6,262,113 B1 | 7/2001 | Widdowson et al. |
| 6,271,261 B1 | 8/2001 | Widdowson |
| 6,294,350 B1 | 9/2001 | Peterson |
| 6,297,381 B1 | 10/2001 | Cirillo et al. |
| 6,310,068 B1 | 10/2001 | Böttcher et al. |
| 6,316,462 B1 | 11/2001 | Bishop et al. |
| 6,319,921 B1 | 11/2001 | Cirillo et al. |
| 6,329,415 B1 | 12/2001 | Cirillo et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,352,977 B1 | 3/2002 | Astles et al. |
| 6,358,525 B1 | 3/2002 | Guo et al. |
| 6,358,945 B1 | 3/2002 | Breitfelder et al. |
| 6,361,773 B1 | 3/2002 | Lee et al. |
| 6,372,773 B1 | 4/2002 | Regan |
| 6,372,933 B1 | 4/2002 | Baine et al. |
| 6,380,218 B1 | 4/2002 | Marfat et al. |
| 6,383,734 B1 | 5/2002 | Marshall et al. |
| 6,387,900 B1 | 5/2002 | Pevarello et al. |
| 6,391,917 B1 | 5/2002 | Petrie et al. |
| 6,403,588 B1 | 6/2002 | Hayakawa et al. |
| 6,414,011 B1 | 7/2002 | Hogenkamp et al. |
| 6,444,691 B1 | 9/2002 | Oremus et al. |
| 6,448,079 B1 | 9/2002 | Monia et al. |
| 6,479,519 B1 | 11/2002 | Astles et al. |
| 6,492,393 B1 | 12/2002 | Breitfelder et al. |

(56) References Cited

U.S. PATENT DOCUMENTS

| | | |
|---|---|---|
| 6,495,331 B1 | 12/2002 | Gelfand et al. |
| 6,500,863 B1 | 12/2002 | Jin et al. |
| 6,511,800 B1 | 1/2003 | Singh |
| 6,511,997 B1 | 1/2003 | Minami et al. |
| 6,521,407 B1 | 2/2003 | Warenius et al. |
| 6,521,592 B2 | 2/2003 | Ko et al. |
| 6,524,832 B1 | 2/2003 | Kufe et al. |
| 6,525,046 B1 | 2/2003 | Cirillo et al. |
| 6,525,065 B1 | 2/2003 | Caldwell et al. |
| 6,525,091 B2 | 2/2003 | Robinson et al. |
| 6,583,282 B1 | 6/2003 | Zhang et al. |
| 6,608,052 B2 | 8/2003 | Breitfelder et al. |
| 6,617,324 B1 | 9/2003 | Naraian et al. |
| 6,635,421 B1 | 10/2003 | Klagsbrun et al. |
| 6,653,320 B2 | 11/2003 | Hayakawa et al. |
| 6,656,963 B2 | 12/2003 | Firestone et al. |
| 6,673,777 B1 | 1/2004 | Tracey et al. |
| 6,689,560 B1 | 2/2004 | Rapp et al. |
| 6,797,823 B1 | 9/2004 | Kubo et al. |
| 6,958,333 B1 | 10/2005 | Hayama et al. |
| 7,070,968 B2 | 7/2006 | Kufe et al. |
| 7,235,576 B1 | 6/2007 | Riedl et al. |
| 7,253,286 B2 | 8/2007 | Funahashi et al. |
| 7,307,071 B2 | 12/2007 | Lyons et al. |
| 7,329,670 B1 | 2/2008 | Dumas et al. |
| 7,351,834 B1 | 4/2008 | Riedl et al. |
| 7,371,763 B2 | 5/2008 | Dumas et al. |
| 7,517,880 B2 | 4/2009 | Miller et al. |
| 7,528,255 B2 | 5/2009 | Riedl et al. |
| 7,547,695 B2 | 6/2009 | Hoelzemann et al. |
| 7,557,129 B2 | 7/2009 | Scott et al. |
| 7,605,261 B2 | 10/2009 | Deprez et al. |
| 7,612,092 B2 | 11/2009 | Funahashi et al. |
| 7,678,811 B2 | 3/2010 | Dumas et al. |
| 2001/0006975 A1 | 7/2001 | Wood et al. |
| 2001/0011135 A1 | 8/2001 | Riedl et al. |
| 2001/0011136 A1 | 8/2001 | Riedl et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2001/0038842 A1 | 11/2001 | Achen et al. |
| 2002/0037276 A1 | 3/2002 | Ptasznik et al. |
| 2002/0042517 A1 | 4/2002 | Uday et al. |
| 2002/0062763 A1 | 5/2002 | Macholdt et al. |
| 2002/0065283 A1 | 5/2002 | McMahon et al. |
| 2002/0065296 A1 | 5/2002 | Dumas et al. |
| 2002/0082255 A1 | 6/2002 | Eastwood |
| 2002/0085857 A1 | 7/2002 | Kim et al. |
| 2002/0085859 A1 | 7/2002 | Hashimoto et al. |
| 2002/0103253 A1 | 8/2002 | Ranges et al. |
| 2002/0111495 A1 | 8/2002 | Magee et al. |
| 2002/0128321 A1 | 9/2002 | Widdowson et al. |
| 2002/0137774 A1 | 9/2002 | Riedl et al. |
| 2002/0161014 A1 | 10/2002 | Sadhu et al. |
| 2002/0165275 A1 | 11/2002 | Wu et al. |
| 2002/0165349 A1 | 11/2002 | Kirsch et al. |
| 2002/0165394 A1 | 11/2002 | Dumas et al. |
| 2002/0173507 A1 | 11/2002 | Santora et al. |
| 2002/0188027 A1 | 12/2002 | Robinson et al. |
| 2002/0197256 A1 | 12/2002 | Grewal |
| 2003/0069284 A1 | 4/2003 | Keegan et al. |
| 2003/0105091 A1 | 6/2003 | Riedl et al. |
| 2003/0125359 A1 | 7/2003 | Lyons et al. |
| 2003/0130309 A1 | 7/2003 | Moss et al. |
| 2003/0139605 A1 | 7/2003 | Riedl et al. |
| 2003/0144278 A1 | 7/2003 | Riedl et al. |
| 2003/0157104 A1 | 8/2003 | Waksal |
| 2003/0181442 A1 | 9/2003 | Riedl et al. |
| 2003/0207870 A1 | 11/2003 | Dumas et al. |
| 2003/0207872 A1 | 11/2003 | Riedl et al. |
| 2003/0207914 A1 | 11/2003 | Dumas et al. |
| 2003/0216396 A1 | 11/2003 | Dumas et al. |
| 2003/0216446 A1 | 11/2003 | Dumas et al. |
| 2003/0232400 A1 | 12/2003 | Radka et al. |
| 2003/0232765 A1 | 12/2003 | Carter et al. |
| 2004/0023961 A1 | 2/2004 | Dumas et al. |
| 2004/0052880 A1 | 3/2004 | Kobayashi et al. |
| 2004/0096855 A1 | 5/2004 | Stratton et al. |
| 2004/0147541 A1 | 7/2004 | Lane et al. |
| 2004/0192770 A1 | 9/2004 | Kozikowski et al. |
| 2004/0197256 A1 | 10/2004 | Rogers et al. |
| 2004/0209905 A1 | 10/2004 | Kubo et al. |
| 2004/0224937 A1 | 11/2004 | Furness et al. |
| 2004/0229937 A1 | 11/2004 | Dumas et al. |
| 2004/0235829 A1 | 11/2004 | Scott et al. |
| 2005/0032798 A1 | 2/2005 | Boyer et al. |
| 2005/0038031 A1 | 2/2005 | Dumas et al. |
| 2005/0038080 A1 | 2/2005 | Boyer et al. |
| 2005/0059703 A1 | 3/2005 | Wilhelm et al. |
| 2005/0069963 A1 | 3/2005 | Lokshin et al. |
| 2005/0096344 A1 | 5/2005 | Fraley et al. |
| 2005/0175737 A1 | 8/2005 | Knobel |
| 2005/0256174 A1 | 11/2005 | Wood et al. |
| 2005/0288286 A1 | 12/2005 | Flynn et al. |
| 2006/0058358 A1 | 3/2006 | Dumas et al. |
| 2006/0078617 A1 | 4/2006 | Schueckler |
| 2006/0211738 A1 | 9/2006 | Mitchell et al. |
| 2006/0234931 A1 | 10/2006 | Biggs, III et al. |
| 2006/0241301 A1 | 10/2006 | Hoelzemann et al. |
| 2006/0247186 A1 | 11/2006 | Carter et al. |
| 2006/0281762 A1 | 12/2006 | Staehle et al. |
| 2007/0020704 A1 | 1/2007 | Wilhelm et al. |
| 2007/0037224 A1 | 2/2007 | Hamer et al. |
| 2007/0066060 A1 | 3/2007 | Stahle et al. |
| 2007/0105142 A1 | 5/2007 | Wilhelm |
| 2007/0149594 A1 | 6/2007 | Finsinger et al. |
| 2007/0173514 A1 | 7/2007 | Moss et al. |
| 2007/0178494 A1 | 8/2007 | Elting et al. |
| 2007/0244120 A1 | 10/2007 | Dumas et al. |
| 2007/0254295 A1 | 11/2007 | Harvey et al. |
| 2007/0265315 A1 | 11/2007 | Dumas et al. |
| 2008/0009527 A1 | 1/2008 | Dumas et al. |
| 2008/0027061 A1 | 1/2008 | Riedl et al. |
| 2008/0032979 A1 | 2/2008 | Riedl et al. |
| 2008/0045546 A1 | 2/2008 | Bouchon et al. |
| 2008/0045589 A1 | 2/2008 | Kelley |
| 2008/0085902 A1 | 4/2008 | Bold et al. |
| 2008/0108672 A1 | 5/2008 | Riedl et al. |
| 2008/0153823 A1 | 6/2008 | Riedl et al. |
| 2008/0194580 A1 | 8/2008 | Dumas et al. |
| 2008/0207699 A1 | 8/2008 | Hoelzemann et al. |
| 2008/0214545 A1 | 9/2008 | Lee et al. |
| 2008/0227828 A1 | 9/2008 | Dumas et al. |
| 2008/0242707 A1 | 10/2008 | Schuckler et al. |
| 2008/0262236 A1 | 10/2008 | Logers et al. |
| 2008/0269265 A1 | 10/2008 | Miller et al. |
| 2008/0300281 A1 | 12/2008 | Dumas et al. |
| 2008/0311601 A1 | 12/2008 | Elting et al. |
| 2008/0311604 A1 | 12/2008 | Elting et al. |
| 2009/0068146 A1 | 3/2009 | Wilhelm |
| 2009/0093526 A1 | 4/2009 | Miller et al. |
| 2009/0118268 A1 | 5/2009 | Riedl et al. |
| 2009/0176791 A1 | 7/2009 | Sandner et al. |
| 2009/0192127 A1 | 7/2009 | Scheuring et al. |
| 2009/0215833 A1 | 8/2009 | Grunenberg et al. |
| 2009/0215835 A1 | 8/2009 | Wilhelm |
| 2009/0221010 A1 | 9/2009 | Elting et al. |
| 2009/0227637 A1 | 9/2009 | Weber et al. |
| 2009/0306020 A1 | 12/2009 | Scheuring et al. |
| 2010/0035888 A1 | 2/2010 | Sandner et al. |
| 2010/0063088 A1 | 3/2010 | Wood et al. |

FOREIGN PATENT DOCUMENTS

| | | |
|---|---|---|
| AU | 4966497 A1 | 6/1998 |
| CA | 2028536 A1 | 4/1991 |
| CA | 2 146 707 A1 | 10/1995 |
| CH | 479557 | 11/1969 |
| CL | 38688 | 6/1993 |
| DD | 253997 A1 | 2/1988 |
| DE | 487014 C1 | 11/1929 |
| DE | 511468 C1 | 10/1930 |
| DE | 523437 C1 | 4/1931 |
| DE | 2436179 A1 | 2/1975 |

(56) References Cited

FOREIGN PATENT DOCUMENTS

| | | |
|---|---|---|
| DE | 2501648 A1 | 7/1975 |
| DE | 3305866 A1 | 8/1984 |
| DE | 2436179 C2 | 4/1986 |
| DE | 3529247 A1 | 11/1986 |
| DE | 3540377 A1 | 5/1987 |
| EP | 0016371 A1 | 10/1980 |
| EP | 0107214 A2 | 5/1984 |
| EP | 0116932 A1 | 8/1984 |
| EP | 0192263 A2 | 8/1986 |
| EP | 0202538 A1 | 11/1986 |
| EP | 0230400 A2 | 7/1987 |
| EP | 0233559 A1 | 8/1987 |
| EP | 0242666 A1 | 10/1987 |
| EP | 0264904 A2 | 4/1988 |
| EP | 0314615 A2 | 5/1989 |
| EP | 0335156 A1 | 10/1989 |
| EP | 0359148 A1 | 3/1990 |
| EP | 0371876 A1 | 6/1990 |
| EP | 0379915 A1 | 8/1990 |
| EP | 0380048 A2 | 8/1990 |
| EP | 0381987 A1 | 8/1990 |
| EP | 0405233 A1 | 1/1991 |
| EP | 0425443 A1 | 5/1991 |
| EP | 0459887 A1 | 12/1991 |
| EP | 0233559 B1 | 5/1992 |
| EP | 0192263 B1 | 7/1992 |
| EP | 0502504 A1 | 9/1992 |
| EP | 0509795 A2 | 10/1992 |
| EP | 0676395 A2 | 10/1995 |
| EP | 0690344 A1 | 1/1996 |
| EP | 0709220 A1 | 5/1996 |
| EP | 0709225 A1 | 5/1996 |
| EP | 0709225 B1 | 8/1998 |
| EP | 0860433 A1 | 8/1998 |
| EP | 1056725 A1 | 12/2000 |
| EP | 1199306 A1 | 4/2002 |
| EP | 1256587 A1 | 11/2002 |
| EP | 1537075 A0 | 6/2005 |
| FR | 1457172 A | 9/1966 |
| GB | 771333 | 3/1957 |
| GB | 828231 | 2/1960 |
| GB | 921682 | 3/1963 |
| GB | 1 110 099 | 4/1968 |
| GB | 1 111 554 | 5/1968 |
| GB | 1 590 870 | 6/1981 |
| HU | P0004437 | 6/2001 |
| IR | 26555 | 1/2000 |
| JO | 10-306078 A | 11/1998 |
| JP | 44-2569 B | 2/1969 |
| JP | 50-76072 A | 6/1975 |
| JP | 50-77375 A | 6/1975 |
| JP | 50-149668 A | 11/1975 |
| JP | 51-63170 A | 6/1976 |
| JP | 51-80862 A | 7/1976 |
| JP | 53-86033 A | 7/1978 |
| JP | 54-32468 A | 9/1979 |
| JP | 55-98152 A | 7/1980 |
| JP | 55-124763 A | 9/1980 |
| JP | 55-162772 A | 12/1980 |
| JP | 57-53785 B2 | 11/1982 |
| JP | 58-21626 B2 | 5/1983 |
| JP | 61-20039 A | 1/1986 |
| JP | 63-214752 A | 9/1988 |
| JP | 64-9455 A | 1/1989 |
| JP | 1-102461 A | 4/1989 |
| JP | 1-132580 A | 5/1989 |
| JP | 1-200254 A | 8/1989 |
| JP | 1-259360 A | 10/1989 |
| JP | 2-22650 A | 1/1990 |
| JP | 2-23337 A | 1/1990 |
| JP | 2-35450 A | 2/1990 |
| JP | 2-105146 A | 4/1990 |
| JP | 2-108048 A | 4/1990 |
| JP | 2-150840 A | 6/1990 |
| JP | 3-53247 A | 3/1991 |
| JP | 3-144634 A | 6/1991 |
| JP | 3-198049 A | 8/1991 |
| JP | 6-75172 A | 9/1994 |
| JP | 8-301841 A | 11/1996 |
| LB | 6124 | 1/2000 |
| WO | WO 90/02112 A1 | 3/1990 |
| WO | WO 92/03413 A1 | 3/1992 |
| WO | WO 92/05179 A1 | 4/1992 |
| WO | WO 93/04170 A1 | 3/1993 |
| WO | WO 93/18028 A1 | 9/1993 |
| WO | WO 93/24458 A1 | 12/1993 |
| WO | WO 94/02136 A1 | 2/1994 |
| WO | WO 94/02485 A1 | 2/1994 |
| WO | WO 94/04541 A1 | 3/1994 |
| WO | WO 94/14801 A1 | 7/1994 |
| WO | WO 94/18170 A1 | 8/1994 |
| WO | WO 94/22807 A1 | 10/1994 |
| WO | WO 94/23755 A1 | 10/1994 |
| WO | WO 94/25012 A2 | 11/1994 |
| WO | WO 95/02136 A1 | 1/1995 |
| WO | WO 95/02591 A1 | 1/1995 |
| WO | WO 95/07922 A1 | 3/1995 |
| WO | WO 95/13067 A1 | 5/1995 |
| WO | WO 95/14023 A1 | 5/1995 |
| WO | WO 95/16691 A1 | 6/1995 |
| WO | WO 95/19169 A2 | 7/1995 |
| WO | WO 95/31451 A1 | 11/1995 |
| WO | WO 95/33458 A1 | 12/1995 |
| WO | WO 95/33460 A1 | 12/1995 |
| WO | WO 96/02112 A1 | 1/1996 |
| WO | WO 96/10559 A1 | 4/1996 |
| WO | WO 96/13632 A1 | 5/1996 |
| WO | WO 96/25157 A1 | 8/1996 |
| WO | WO 96/40673 A1 | 12/1996 |
| WO | WO 96/40675 A1 | 12/1996 |
| WO | WO 96/41807 A1 | 12/1996 |
| WO | WO 97/03069 A1 | 1/1997 |
| WO | WO 97/09973 A2 | 3/1997 |
| WO | WO 97/17267 A1 | 5/1997 |
| WO | WO 97/17329 A1 | 5/1997 |
| WO | WO 97/29743 A1 | 8/1997 |
| WO | WO 97/30992 A1 | 8/1997 |
| WO | WO 97/34146 A1 | 9/1997 |
| WO | WO 97/40028 A1 | 10/1997 |
| WO | WO 97/40842 A1 | 11/1997 |
| WO | WO 97/45400 A1 | 12/1997 |
| WO | WO 97/49399 A1 | 12/1997 |
| WO | WO 97/49400 A1 | 12/1997 |
| WO | WO 98/17207 A1 | 4/1998 |
| WO | WO 98/17267 A1 | 4/1998 |
| WO | WO 98/20868 A1 | 5/1998 |
| WO | WO 98/22103 A1 | 5/1998 |
| WO | WO 98/22432 A1 | 5/1998 |
| WO | WO 98/32439 A1 | 7/1998 |
| WO | WO 98/34929 A1 | 8/1998 |
| WO | WO 98/45268 A1 | 10/1998 |
| WO | WO 98/52558 A1 | 11/1998 |
| WO | WO 98/52559 A1 | 11/1998 |
| WO | WO 98/52937 A2 | 11/1998 |
| WO | WO 98/52941 A1 | 11/1998 |
| WO | WO 98149150 A1 | 11/1998 |
| WO | WO 98/56377 A1 | 12/1998 |
| WO | WO 99/00357 A1 | 1/1999 |
| WO | WO 99/00370 A1 | 1/1999 |
| WO | WO 99/20617 A1 | 4/1999 |
| WO | WO 99/21835 A1 | 5/1999 |
| WO | WO 99/23091 A1 | 5/1999 |
| WO | WO 99/24035 A1 | 5/1999 |
| WO | WO 99/24398 A2 | 5/1999 |
| WO | WO 99/24635 A1 | 5/1999 |
| WO | WO 99/26657 A1 | 6/1999 |
| WO | WO 99/28305 A1 | 6/1999 |
| WO | WO 99/32106 A1 | 7/1999 |
| WO | WO 99/32109 A1 | 7/1999 |
| WO | WO 99/32110 A1 | 7/1999 |
| WO | WO 99/32111 A1 | 7/1999 |
| WO | WO 99/32436 A1 | 7/1999 |
| WO | WO 99/32437 A1 | 7/1999 |
| WO | WO 99/32455 A1 | 7/1999 |

(56) References Cited

FOREIGN PATENT DOCUMENTS

| | | |
|---|---|---|
| WO | WO 99/32463 A1 | 7/1999 |
| WO | WO 99/33458 A1 | 7/1999 |
| WO | WO 99135132 A1 | 7/1999 |
| WO | WO 99/40673 A1 | 8/1999 |
| WO | WO 99/58502 A1 | 11/1999 |
| WO | WO 99/62890 A1 | 12/1999 |
| WO | WO 00/1497 A2 | 3/2000 |
| WO | WO 00/17175 A1 | 3/2000 |
| WO | WO 00/19205 A1 | 4/2000 |
| WO | WO 00/26203 A1 | 5/2000 |
| WO | WO 00/27414 A2 | 5/2000 |
| WO | WO 00/31238 A2 | 6/2000 |
| WO | WO 00/34303 A1 | 6/2000 |
| WO | WO 00/35454 A1 | 6/2000 |
| WO | WO 00/35455 A1 | 6/2000 |
| WO | WO 00/39101 A1 | 7/2000 |
| WO | WO 00/39116 A1 | 7/2000 |
| WO | WO 00/41698 A1 | 7/2000 |
| WO | WO 00/42012 A1 | 7/2000 |
| WO | WO 00/43366 A1 | 7/2000 |
| WO | WO 00/43384 A1 | 7/2000 |
| WO | WO 00/47577 A1 | 8/2000 |
| WO | WO 00/50425 A1 | 8/2000 |
| WO | WO 00/55139 A2 | 9/2000 |
| WO | WO 00/55152 A2 | 9/2000 |
| WO | WO 00/56331 A1 | 9/2000 |
| WO | WO 00/71506 A2 | 11/2000 |
| WO | WO 00/71532 A1 | 11/2000 |
| WO | WO 01/04115 A2 | 1/2001 |
| WO | WO 01/07411 A1 | 2/2001 |
| WO | WO 01/09088 A1 | 2/2001 |
| WO | WO 01/12188 A1 | 2/2001 |
| WO | WO 01/36403 A1 | 5/2001 |
| WO | WO 01/4789 A1 | 7/2001 |
| WO | WO 01/03403 A2 | 8/2001 |
| WO | WO 01/54723 A1 | 8/2001 |
| WO | WO 01/54727 A1 | 8/2001 |
| WO | WO 01/57008 A1 | 8/2001 |
| WO | WO 01/66099 A2 | 9/2001 |
| WO | WO 01/66540 A1 | 9/2001 |
| WO | WO 01/72751 A1 | 10/2001 |
| WO | WO 01/80843 A2 | 11/2001 |
| WO | WO 02/06382 A1 | 1/2002 |
| WO | WO 02/07747 A1 | 1/2002 |
| WO | WO 02/07772 A2 | 1/2002 |
| WO | WO 02/10141 A1 | 2/2002 |
| WO | WO 02/14281 A1 | 2/2002 |
| WO | WO 02/14311 A2 | 2/2002 |
| WO | WO 02/18346 A1 | 3/2002 |
| WO | WO 02/24635 A2 | 3/2002 |
| WO | WO 02/25286 | 3/2002 |
| WO | WO 02/32872 A1 | 4/2002 |
| WO | WO 02/40445 A1 | 5/2002 |
| WO | WO 02/42012 A1 | 5/2002 |
| WO | WO 02/44156 A2 | 6/2002 |
| WO | WO 02/44158 A1 | 6/2002 |
| WO | WO 02/50091 A1 | 6/2002 |
| WO | WO 02/059081 A2 | 8/2002 |
| WO | WO 02/059102 A2 | 8/2002 |
| WO | WO 02/060900 A2 | 8/2002 |
| WO | WO 02/062763 A2 | 8/2002 |
| WO | WO 02/070008 A1 | 9/2002 |
| WO | WO 02/076930 A2 | 10/2002 |
| WO | WO 02/076977 A2 | 10/2002 |
| WO | WO 02/083628 A1 | 10/2002 |
| WO | WO 02/083642 A1 | 10/2002 |
| WO | WO 02/085857 A2 | 10/2002 |
| WO | WO 02/085859 A1 | 10/2002 |
| WO | WO 02/088090 A2 | 11/2002 |
| WO | WO 02/092576 A1 | 11/2002 |
| WO | WO 03/004523 A1 | 1/2003 |
| WO | WO 03/005999 A2 | 1/2003 |
| WO | WO 03/047523 A2 | 6/2003 |
| WO | WO 03/047579 A1 | 6/2003 |
| WO | WO 03/056036 A2 | 7/2003 |
| WO | WO 03/059373 A2 | 7/2003 |
| WO | WO 03/060111 A2 | 7/2003 |
| WO | WO 03/065995 A2 | 8/2003 |
| WO | WO 03/068223 A1 | 8/2003 |
| WO | WO 03/068228 A1 | 8/2003 |
| WO | WO 03/068229 A1 | 8/2003 |
| WO | WO 03/068746 A1 | 8/2003 |
| WO | WO 03/082272 A1 | 10/2003 |
| WO | WO 03/094626 A1 | 11/2003 |
| WO | WO 03/097854 A2 | 11/2003 |
| WO | WO 03/099771 A2 | 12/2003 |
| WO | WO 2004/004720 A1 | 1/2004 |
| WO | WO 2004/019941 A1 | 3/2004 |
| WO | WO 2004/037789 A2 | 5/2004 |
| WO | WO 2004/043374 A2 | 5/2004 |
| WO | WO 2004/045578 A2 | 6/2004 |
| WO | WO 2004/052880 A1 | 6/2004 |
| WO | WO 2004/078128 A2 | 9/2004 |
| WO | WO 2004/078746 A2 | 9/2004 |
| WO | WO 2004/078747 A1 | 9/2004 |
| WO | WO 2004/078748 A2 | 9/2004 |
| WO | WO 2004/085399 A1 | 10/2004 |
| WO | WO 2004/085425 A1 | 10/2004 |
| WO | WO 2004/108713 A1 | 12/2004 |
| WO | WO 2004/108715 A1 | 12/2004 |
| WO | WO 2004/113274 A2 | 12/2004 |
| WO | WO 2005/000284 A2 | 1/2005 |
| WO | WO 2005/002673 A1 | 1/2005 |
| WO | WO 2005/004863 A1 | 1/2005 |
| WO | WO 2005/004864 A1 | 1/2005 |
| WO | WO 2005/005434 A1 | 1/2005 |
| WO | WO 20051005389 A2 | 1/2005 |
| WO | WO 2005/0009367 A2 | 2/2005 |
| WO | WO 2005/009961 A2 | 2/2005 |
| WO | WO 2005/011700 A1 | 2/2005 |
| WO | WO 2005/016252 A2 | 2/2005 |
| WO | WO 2005/019192 A1 | 3/2005 |
| WO | WO 2005/032548 A1 | 4/2005 |
| WO | WO 2005/037273 A2 | 4/2005 |
| WO | WO 2005/037829 A1 | 4/2005 |
| WO | WO 20051037285 A1 | 4/2005 |
| WO | WO 2005/042520 A1 | 5/2005 |
| WO | WO 2005/047283 A1 | 5/2005 |
| WO | WO 2005/048948 A2 | 6/2005 |
| WO | WO 2005/049603 A1 | 6/2005 |
| WO | WO 2005/056764 A2 | 6/2005 |
| WO | WO 2005/058832 A1 | 6/2005 |
| WO | WO 2005/059179 A1 | 6/2005 |
| WO | WO 20051075425 A2 | 8/2005 |
| WO | WO 2005/089443 A2 | 9/2005 |
| WO | WO 2005/110994 A2 | 11/2005 |
| WO | WO 2006/027346 A2 | 3/2006 |
| WO | WO 20061026500 A1 | 3/2006 |
| WO | WO 20061026501 A1 | 3/2006 |
| WO | WO 2006/034397 A1 | 4/2006 |
| WO | WO 2006/094626 A1 | 9/2006 |
| WO | WO 20061105844 A1 | 10/2006 |
| WO | WO 2006/125540 A1 | 11/2006 |
| WO | WO 2007/015947 A2 | 2/2007 |
| WO | WO 2007/039403 A1 | 4/2007 |
| WO | WO 2007/039404 A1 | 4/2007 |
| WO | WO 2007/047955 A2 | 4/2007 |
| WO | WO 007/056011 A2 | 5/2007 |
| WO | WO 2007/053573 A2 | 5/2007 |
| WO | WO 2007/054215 A1 | 5/2007 |
| WO | WO 2007/056012 A2 | 5/2007 |
| WO | WO 2007/059094 A2 | 5/2007 |
| WO | WO 2007/059154 A2 | 5/2007 |
| WO | WO 2007/059155 A1 | 5/2007 |
| WO | WO 2007/064872 A2 | 6/2007 |
| WO | WO 2007/087575 A2 | 8/2007 |
| WO | WO 2007/096393 A1 | 8/2007 |
| WO | WO 2007/096395 A1 | 8/2007 |
| WO | WO 2007/123722 A2 | 11/2007 |
| WO | 2007/139930 A2 | 12/2007 |
| WO | WO 2008/055966 A1 | 5/2008 |
| WO | WO 2008/079968 A1 | 7/2008 |
| WO | WO 2008/079972 A2 | 7/2008 |

(56) References Cited

FOREIGN PATENT DOCUMENTS

| WO | WO 2008/089389 A2 | 7/2008 |
|---|---|---|
| WO | WO 2009/034308 A2 | 3/2009 |
| WO | WO 2009/054004 A2 | 4/2009 |

OTHER PUBLICATIONS

Arora et al.,"Stromelysin 3, Ets-1, and Vascular Endothelial Growth Factor Expression in Oral Precancerous and Cancerous Lesions: Correlation with Microvessel Density, Progression, and Prognosis." Clinical Cancer Research, 11: 2272-2284 (Mar. 15, 2005).

Ascierto et al., "Prognostic Value of Serum VEGF in Melanoma Patients: a Pilot Study" Anticancer Research, 24: 4255-4258 (2004).

Auclair et al., "Bay 43-9006 (Sorafenib) is a potent inhibitor of FLT3 tyrosine kinase signaling and proliferation in AML cells," Abstract #5991, 96$^{th}$ Annual Meeting Anaheirn/Orange County, CA, Apr. 16-20. 2005.

Audia et al., "Potent, Selective Tetrahydro-β-carboline Antagonists of the Serotonin 2B (5HT$_{2B}$) Contractile Receptor in the Rat Stomach Fundus," *J. Med. Chem.* 1996, 39, pp. 2773-2780.

Avruch et al., "Raf meets Ras: completing the framework of a signal transduction pathway," *TIBS* 19; Jul. 1994; pp. 279-283.

Awada et al., "Phase I safety and pharmacokinetics of Bay 43-9006 administered for 21 days on/7 days off in patients with advanced, refractory solid tumours" British Journal of Cancer 92, pp. 1855-1861 (2005).

Bachelot et al., "Prognostic value of serum levels of interleukin 6 and of serum and plasma levels of vascular endothelial growth factor in hormone-refractory metastatic breast cancer patients," British Journal of Cancer, 88: 1721-1726 (2003).

Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and immune Function," JPET 279: pp. 1453-1461 (1996).

Baka et al., "A review of the latest clinical compounds to inhibit VEGF in pathological angiogenesis," Expert Opinion Therapeutic Targets, 2006, vol. 10, No. 6, pp. 867-876.

Balant et at., "Metabolic Considerations in Prodrug Design," Chapter Twenty-Three In: Burger's Medicinal Chemistry and Drug Discovery, 5$^{th}$ ed. John Wiley & Sons, Inc.. New York. 1995: vol. 1.pp. 949-982.

Bando et al., "Association between intratumoral free and total VEGF, soluble VEGFR-1, VEGFR-2 and prognosis in breast cancer" British Journal of Cancer, 2005, vol. 92, pp. 553-561.

Banetjee et al., "Murine Coronavirus Replication-Induced p38 Mitogen-Activated Protein Kinase Activation Promotes Interleukin-6 Production and Virus Replication in Cultured Cells," Journal of Virology. American Society for Microbiology, 2002: vol. 76, pp. 5937-5948.

Bankston et al., "A Scaleable Synthesis of BAY 43-9006: A Potent Raf Kinase Inhibitor for the Treatment of Cancer," Organic Process Research & Development, 2002, vol. 6, pp, 777-781.

Barnett et al., "Identification and characterization of pleckstrin-homology-domain-dependent and isoenzyme-specific Akt inhibitors," Biochem J., vol. 385, 2005, pp. 399-408.

Bankston et al., "A Scaleable Synthesis of BAY 43-9006: A Potent Raf Kinase Inhibitor for the Treatment of Cancer," Organic Process Research & Development, vol. 6, pp. 777-781 (2002).

Bayer Corporation et al., "Trial of BAY 43-9006 in Patients with Relapsed or Refractory Advanced Non-Small Cell Lung Carcinoma", NCT0010413, clinicaltrials.gov, 3 pages,(Jan. 2005).

European Medicines Agency, "CHMP Assessment Report for Nexavar" Doc Ref: EMEA/CHMP/140610/2006, 63 pages. (Apr. 2006).

Strumberg et al., "Phase I Clinical, Pharmacokinetic and Pharmacodynamic Study of the Raf Kinase Inhibitor BAY 43-9006 in Patients with Locally Advanced or Metastatic Cancer," Proc. Am. Soc. Clin. Oncol. 20: 2001 (abstr 330) (2001).

Iwadate et al., MEDLINE/NLM, NLM8336809 "Intra-arterial ACNU, CDDP chemotherapy for brain metastases from lung cancer: comparison of cases with and without intra-arterial mannitol infusion," Clinical Trial, 21(6): p. 513-518, 1 page abstract, (Jun. 1993).

Abstract of EP 4931 A (Equivalent 4,240,820), Bayer AG, 1 page (Dec 23, 1980).

Abstract of EP 0405233A1, Mitsubishi Kasei Corp., 2 pages (Jun. 15, 1989).

Abstract of EP 0405233A1, Tetsuo Sekiya et al., 1 page (Jan 2, 1991).

esp@cenet Abstract of Japan 02-023337, 1 page (Jan 25, 1990).

Huang et al., "Blockade of VEGFR1 and 2 Suppresses Pathologique Angiogenesis and Vascular Leakage in the Eye." PloS ONE 6 (6); e21411. doi:10.1371/journal.pone.0021411 (2011).

English abstract of JP 50-149668 A and JP 56-29871 B, Derwent World Patents Index, Dialog File No. 351, Acc. No. 1488399, 3 pages, (Nov.29, 1975).

Peacock et al., "Angiogenesis Inhibition Suppresses Collagen Arthritis," J. Exp. Med. 175, 1135-1138, (1992).

Toi et al., "Inhibition of vascular endothelial growth-factor induced cell-growth by an angiogenesis inhibitor agm-1470 in capillary endothelial-cells," Oncol. Rep. Mar. 1994 ; 1(2) :423-426.

Diago et al., "Ranizumab Combined with Low-Dose Sorafenib for Exudative Age-Related Macular Degeneration," Mayo Clin. Proc. Feb. 2008 :83(2):231-234.

Baumann et al., "Raf induces NF-κB by mentbrane shuttle kinase MEKK1, a signaling pathway critical for transformation," Proc. Natl. Acad, Sci. USA, vol. 97: No. 9. 4615-4620 (Apr. 25, 2000).

Bellacosa et al., "Molecular Alterations of the AK172 Oncogene in Ovarian an Breast Carcinomas," Int. J. Cancer (Pred. Oncol.), vol. 64, 1995, pp. 280-285.

Berge et al., "Pharmaceutical Salts." Journal of Pharmaceutical Sciences. Jan. 19 77:1-19, vol. 66, No. 1.

Bergstralh et al., "Microtubule stabilizing agents: Their molecular signaling consequences and the potential for enhancement by drug combination," *Cancer Treatment Reviews*, 2006, vol. 32, pp. 166-179.

Bertrand et al., "Inhibition of PI3K, mTOR and MEK signaling pathways promotes rapid apoptosis in B-Lineage All in the presence of stromal cell support", Leukemia, vol. 19, pp. 98-102 (published online Oct. 21, 2004).

Bhagwat et at., "The angiogenic regulator CD13/APN is a transcriptional target of Ras signaling pathways in endothelial morphogenesis," Blood, vol. 101, No. 5, pp. 1818-1826, (Mar. 1, 2003).

Bianchi et al., "A Phase II Multi-center uncontrolled trial of sorafenib (BAY 43-9006) in patients with metastatic breast cancer" Journal of Clinical Oncology, Draft 33 pages (presented previously Oct. 30-Nov. 3, 2005).

Martin-Blanco, "p38 MAPK signalling cascades: ancient roles and new functions," BioEssays, 22:637-645, 2000.

Foussard-Blanpin, Odette, "Comparative pharmacological study of substituted carboxamides upon central nervous system," Ann. Pharm. Fr. (1982), 40 (4), pp. 339-350.

Board et al., "Platelet-derived growth factor receptor (PDGFR): A target for anticancer therapeutics," Drug Resistance Updates 8 (2005) 75-83.

Bok et al., "Vascular Endothelial Growth Factor and Basic Fibroblast, Growth Factor Urine Levels as Predictors of Outcome in Hormone refractoryProstate Cancer Patients: A Cancer and Leukemia Group B Study," Cancer Research, 61: 2533-2536 (Mar. 15, 2001).

Bollag et al., "Raf pathway inhibitors in oncology," Current Opinion in Investigational Drugs (2003) 4(12): pp. 1436-1441.

Bolton et al., "Chapter 17. *Ras* Oncogene Directed Approaches in Cancer Chemotherapy," Annual Reports in Medicinal Chemistry, vol. 29, 1994, pp. 165-174.

Bono et al., "Serum KIT and KIT ligand levels in patients with gastrointestinal stromal tumors treated with imatinib," Blood 103:2929-2935 (2004).

Bos, J.L. "*ras* Oncogenes in Human Cancer: A Review," *Cancer Research*, vol. 49, Sep. 1, 1989, pp. 4682-4689.

Boulton et al, "Heterocyclic Rearrangements, Part X. A Generalised Monocyclic Rearrangement," J. Chem. Soc. (C), 1967, pp. 2005-2007.

(56) References Cited

OTHER PUBLICATIONS

Boyer, S.J., "Small Molecule Inhibitors of KDR (VEGFR-2) Kinase: An Overview of Structure Activity Relationships," Current Topics in Medicinal Chemistry, 2002, vol. 2, pp. 973-1000.
Boyd, et al. "Areae Oxides of Quinoline: Epoxidation, N-Oxidation and N-Methylation Reactions," J. Chem. Soc. Perkin Trans. 1, 1991: pp. 2189-2192.
Braybrooke et al, "A Phase II Study of Razoxane, an Antiangiogenic Topoisomerase II Inhibitor, in Renal Cell Cancer with Assessment of Potential Surrogate Markers of Angiogenesis," Clin. Canc. Res. 6:4697-4704 (2000).
Broll et al, "Vascular endothelial growth factor (VEGF)—a valuable serum tumour marker in patients with colorectal cancer?" Fur. J. Surg. Oncol. 27:37-42 (2001).
Bruder et al., "Adenovirus Infection Stimulates The Raf/MAPK Signaling Pathway and Induces Interleukin-8 Expression" Journal of Virology, vol. 71, pp. 398-404, 1997.
Bundgaard, Hans, "Design of prodrugs: Bioreversible derivatives for various functional groups and chemical entities." pp. 1-92, in Design of Prodrugs, Elsevier Science Publishers B.V., Amsterdam, The Netherlands, 1985.
Campbell et al., "Increasing complexity of Ras signaling," Oncogene, 1998 vol. 17, pp. 1395-1413.
Cancer Weekly, "Antisense Technology (Clinical Trial). Phase II Trial of Second Antisense Caner Drug Begins," Cancer Weekly, p. 4 (Dec. 8, 1997).
Canetta et al., "Carboplatin: current status and future prospects," Cancer Treatment Reviews, 1998, pp. 17-32, vol. 15(Supplement B).
Caponigro et al., "Epidermal growth factor receptor as a major anticancer drug target," Exp. Opin. Thera. Targets, 2006, Vol, 10, No. 6, pp. 877-888.
Carey et al., "Contents of Part A," pp. vii-xi and "Contents of Part B," pp. xiii-xviii, in Advanced Organic Chemistry. Second Edition, Part A: Structure and Mechanisms, Plenum Press, NY (1984).
Carling et al., "1-(3-Cyanobenzylpiperidin-4-,yl)-5,-methyl-4-pheny1-1,3-dihydroimidazol-2-one: A Selective High AffinityAntagonist for the Human Dopamine $D_4$ Receptor with Excellent Selectivity over Ion Channels," J. Med. Chem., 1999, 42, pp. 2706-2715.
Carlomagno et al., "BAY 43-9006 inhibition of Oncogenic RET Mutants," Journal of the National Cancer Institute, 2006, vol. 98, No, 5, pp. 326-334.
Carney et al., "Monitoring the Circulating Levels of the HER2/*neu*, Oncoprotein in Breast Cancer," Clin Breast Cancer 5(2): 105-116, (2004).
Carter et al., "Anti-Tumor Efficacy ot the Orally Active *Raf* Kinase Inhibitor BAY 43-9006 in Human Tumor Xenograft Models," Proceedings of the American Association for Cancer Res., vol. 42: p. 923. Mar. 2001, Abstract #4954.
Carter et al., "Drug-Tumor Interactions" pp. 362-365, in: Chemotllerapy of Cancer,Second Edition, John Wiley & Sons, NY (1981).
Carter et al., "Sorafenib is efficacious and tolerated in combination with cytotoxic or cytostatic agents in preclinical models of human non-small cell lung carcinoma," Cancer Chemotherapy and Pharmacology, Springer Berlin/Heidelberg, vol. 59, No. 2, pp. 183-195 (Feb. 2007). Abstract.
Chang et al., "BAY 43-9006 (Sorafenib) inhibits ectopic (s.c.) and orthotopic growth of a murine model of renal adenocarcinoma (Renca) predominantly through inhibition of tumor angiogenesis," 96th Annual Meeting, Anaheim/Orange County, CA, Apr. 16-20, 2005, 1 page.
Chang et al., "Sorafenib (BAY 43-9006) inhibits tumor growth and vascularization and induces tumor apoptosis and hypoxia in RCC xenograft models," Cancer Chemother. Pharmacol., 2007, vol. 59, pp. 561-574.
Chen et al., "Role of Regulatory Elements and the MAP/ERK OR p38 MAPK Pathways for Activation of Human Cytomegalovirus Gene :Expression," Journal of Virology. 2002: vol. 76, No. 10, pp, 4873-4885.
Chen et al., "Suppression of Japanese encephalitis virus infection by non- steroidial, anti-inflammatory drugs," Journal of General Virology, 2002, vol. 83, pp. 1897-1905.
Chen et al., "Expression of Proinflammatory and Proangiogenic Cytokines in Patients with Head and Neck Cancer" Clinical Cancer Research 5:1369-1379 (Jun. 1999).
Chialda et al., "Inhibitors of mitogen-activated protein kinases differentially regulate costimulated T cell cytokine production and mouse airway eosinophilia," Respiratory Research 2005, 6:36, pp. 1-19.
Chin et al., "Vascular endothelial growth factor and soluble Tie-2 receptor in colorectal cancer: associations with disease recurrence," European Journal of Surgical Oncology. 29:497-505 (2003).
Choi et al., "Imatinib-Resistant Cell Lines Are Sensitive to the Raf inhibitor BAY 43-9006," Blood, W.E.B. Saunders Company, Orlando, FL, US, vol. 100, No. 11, Abstract # 1427 (Dec. 10, 2002).
Choong et al., "Forthcoming receptor tyrosine kinase inhibitors," Exp. Opin. Ther. 'Targets, 2006,vol. 10, No. 6, pp. 793-797.
Chow et al., "Measurement of MAP Kinase Activation by Flow Cytometry Using Phospho-Specific Antibodies to MEK and ERK: Potential for Pharmacodynamic Monitoring of Signal Transduction inhibitors," Cytometry (Communications in Clinical Cytometry) 46:72-78 (2001).
Christensen, et al., "Plasma vascular endothelial growth factor and interleukin 8 as biontarkers of antitumor efficacy of a prototypical erbB family tyrosine lase inhibitor," Mol. Cancer Ther., 4(6):938-947 (Jun. 2005).
Chu et al., "Cardiotoxicity associated with tyrosine kinase inhibitor sunitmib," Lancet. 2007, vol. 370, pp. 2011-2019.
Chustecka et al., "Bortezomib and Sorafenib Show Activity in Thyroid Cancer," Medscape. 2 pages. (Nov. 2, 2006).
Clark et al., "Safety and Pharmacokinetics of the Dual Action Raf Kinase and Vascular Endothelial Growth Factor Receptor Inhibitor, BAY 43-9006, in Patients with Advanced, Refractory Solid Tumors," Clinical Cancer Res., Aug. 1.2005, vol. 11, No. 15, pp, 5432-5480.
Garbe, "Ruch ern Therapieplatz für Sorafenib?" Medical Special (2006) 2 pages.
Copéret et al., "A Simple and Efficient Method for the Preparation of Pyridine-N -oxides II," Tetrahedron Letters, Elsevier Science Ltd., Pergamon Press, Oxford, UK 1998: vol. 39, pp. 761-764.
Cortes et al., "Targeting the Microtubules in Breast Cancer Beyond Taxanes: The Epothilones " *The Oncologist*, 2007, vol. 12. pp. 271-280.
Craig, "The mechanisms of drug release from solid dispersions in water-soluble polymers." International Journal of Pharmaceutics 231 (2002) 131-144, Elsevier Science B.V.
Le Cras et at., "Treatment of newborn rats with a VEGF receptor inhibitor causes pulmonary hypertension and abnormal lung structure." Am. J. Physiol. Lung. Cell. Mot. Physiol. vol. 283, pp. L555-L562, 2002.
Crump, Micheal, "Ihhibition of raf kinase in the treatment of acute myeloid leukemia," Medline Abstract ISSN:1381--6128, Current Pharmaceutical Design, vol. 8, issue 25, 2002, pp. 2243-2248.
Cunningham et al, "A Phase I Trial of H-*ras* Antisense Oligonucleotide ISIS 2503 Administered as a Continuous intravenous Infusion in Patients with Advanced Carcinoma," Cancer, 2001, American Cancer Society, vol. 92, No. 5, pp. 1265-1271.
Danson et al., "Improving Outcomes in Advanced Malignant Melanoma. Update on Systemic Therapy," *Drugs*, 2005, vol. 65, No. 6, pp. 733-743.
Dasmahapatra et al., "*In vitro* Combination Treatment with Perifosine and UCN-01 Demonstrates Synergism against Prostate (PC-3) and Lung (A549) Epithelial Adenocarcinoma Cell Lines," Clinical Cancer Research, vol. 10, Aug. 1. 2004, pp, 5242-5252.
Daum et al., "The ins and outs of Raf kinases," TIBS 19, Nov. 1994, pp. 474-480.
Dayan et al., "Tertiary Amine Oxidation using $HOF-CH_3$ CN: A Novel Synthesis of N-Oxides," Synthesis, 1999, No. SI, pp. 1427-1430.
DeGrendele, "Activity of the Raf Kinase Inhibitor BAY 43-9006 in Patients with Advanced Solid Tumors," Clinical Colorectal Cancer, May 2003, vol. 3, pp. 16-18.

(56) References Cited

OTHER PUBLICATIONS

Dehtiing, J. "Große Onkologie-Pipeline" Medizinische Monatsschrift für Pharmazeuten, 2006, 'Village 12914, 2 pages.

Denny, "Prodrug strategies in cancer therapy," European Journal of Medicinal Chemistry. 2001: vol. 36, pp. 577-595.

DeVita et al., "Elevated Perioperative Serum Vascular Endothelial Growth Factor Levels in Patients with Colon Carcinoma," Cancer, 100 (2) pp. 270-278 (2004).

Devlin et al.. "GATT and DISCOVERY: Significant Changes in U.S. Patent Law" Screening Forum, vol. 3, No. 4, pp. 1, 3 and 6 (Dec. 1995).

Doanes et al., "VEGF Stimulates MAPK through a Pathway That Is Unique for Receptor Tyrosine Kinases," Biochem Biophys. Res. Commun. 255: pp. 545-548, 1999.

Dörwald, "Preface," p. IX, in Side Reactions in Organic Synthesis: A Guide to Successful Synthesis Design, Wiley-VCH Verlag GmbH & Co. KGaA (2005).

Downward, J., "Mechanisms and consequence of activation of protein kinase B/Akt," Current Opinion in Cell Biology, vol. 10, 1998, pp. 262-267.

Drevs et at., "Soluble markers for the assessment of biological activity with PTK787/ZK 222584 (PTK/ZK), a vascular endothelial growth factor receptor (VEGFR) tyrosine kinase inhibitor in patients with advanced colorectal cancer from two phase I trials," Annals of Oncology, 16: 558-565 (2005).

Drevs, J., "Soluble Markers for the Detection of Hypoxia under Antiangiogenic Treatment," Anticancer Research, 23: 1159-1162 (2003).

Drevs. J., DieMedizinische Welt, 2006, pp. 3/5, 4/5, 5/5.

"Doxorubicin HCl (ADR)," in drugs: facts and comparisons, 1994 Ed,. pp. 2703-2705.

Dudek et al., "Circulating Angiogenic Cytokines in Patients with Advanced Non-Small Cell Lung Cancer: Correlation with Treatment Response and Survival," Cancer Investigation, 23: 193-200 (2005).

Dumas, J. "Protein kinase inhibitors from the urea class," Curr. Opin. In Drug Discovery and Dev., 5(s):718-727, 2002.

Dumas et al., "Discovery of a New Class of p38 Kinase Inhibitors," Bioorganic & Medicinal Chemistry Letters vol. 10, (2000), pp, 2047-2050.

Dumas et al., "1-Phenyl-5-pyrazolyi Llreas: Potent and Selective p38 Kinase Inhibitors," Bioorganic & Medicinal Chemistry Letters, 2000, vol. 10, pp. 2051-2054.

Dumas, J., "Growth factor receptor kinase inhibitors: Recent progress and clinical impact," Current Opinion in Drug Discovery & Development. 2001, Vol, 4, No. 4, pp, 378-389.

Dumas, J "Protein kinase inhibitors: emerging pharmacophores 1997-2000," Expert Opinion on Therapeutic Patents (2001) vol. 11, No. 3, pp. 405-429.

Durnas et al., "Orally Active p38 Kinase inhibitors from the Urea Class " Poster, 222nd American Cancer Society National Meeting 2001, Med I 256, 1 page.

Dumas, J., "Raf Kinase inhibitors," Expert Opinion on T lerapeutic Patients, vol. 8, No. 12, pp. 1749-1750, 1998.

Dumas et al., "Recent developments in the discovery of protein kinase inhibitors from the urea class," *Current Opinion in Drug Discovery & Development*, 2004, vol. 7, No. 5, pp. 600-616.

Dumas et al., "Synthesis and Pharmacological Characterization of a Potent, Orally Active p38 Kinase Inhibitor," *Bioorganic & Medicinal Chemistry Letters*, 2002, vol. 12, pp. 1559-1562.

Dunst et al., "Tumor Hypoxia and Systemic Levels of Vascular Endothelial Growth Factor (VEGF) in Head and Neck Cancers," Strahlentherapie and Onkologie, 177(9): 469-473 (2001).

Ebos et al., "Multiple circulating proangiogenic factors induced by sunitinib malate are tumor-independent and correlated with antitumor efficacy" PNAS vol. 104, No. 43, pp, 17069-17074 (Oct. 23, 2007).

Ebrahimi et al., "Cytokines in Pancreatic Carcinoma, Correlation with Phenotypic Characteristics and Prognosis," Cancer, 101(12): 2727-2736 (Published on-line Nov 3, 2004).

Eisen et al., "Phase I trial of BAY 43-9006 (Sorafenib) combined with dacarbazine (DTIC) in metastatic melanoma patients," Abstract #7508, Meeting: *2005 ASCO Annual Meeting*, Category: Melamona, Subcategory: Melamona.

Eisen et al., "Somfenib in advanced melanoma: a Phase II randomised discontinuation trial analysis" British Journal of Cancer 95, 581-586 (2006).

Eisenhauer et al., "Impact of new non-cytotoxics in the treatment in ovarian cancer," international J. Gynecol. Cancer, 2001, vol. 11, Supplement 1, pp. 68-72.

El-Deiry, Wafik S., "Meeting Report: The international Conference on Tumor Progression and Therapeutic Resistance", Cancer Research, 2005; vol. 65, No. 11. pp. 4475-4484.

Elting et al., "Biomarkers associated with clinical outcomes in TARGETs, a Phase III single-agent, placebo-controlled study of sorafenib in advanced renal cell carcinoma," Proc. Amer. Assoc. Cancer Res. vol. 47, Abstract # 2909, 2006, pp. 683-684.

Escudier et al., "Randomized Phase III trial of the Raf kinase and VEGFR inhibitor sorafenib (BAY 43-9006) in patients with advanced renal cell carcinoma (RCC)," Meeting: 2005 ASCO Annual Meeting, Category: Genitourinary Cancer, Subcategory: Kidney Cancer, 1 page.

Escudier et al., "Sorafenib in Advanced Clear-Cell Renal-Cell Carcinoma" New England Journal of Medicine vol. 356: 125-134 (Jan. 11, 2007).

European Medicines Agency, "CHMP Assessment Report for Nexavar" Doc Ref: EMEA/CHMP/140610/2006, 63 pages.

Fabian et al., "A small molecule-kinase interaction map for clinical kinase inhibitors," Nature . Biotechnology, 2005, vol. 23, No. 3, pp. 329-336, 4 supplementary pages.

Faderl et al., "Angiogenic factors may have a different prognostic; role in adult acute lymphoblastic leukemia," Blood, 2005 vol. 106 No. 13, pp. 4303-4307.

Faivre et al., "Molecular basis for sunitinib efficacy and future clinical development" Nature Reviews Drug Discovery, Nature Publishing Group, pp. 734-745, vol. 6 (Sep. 2007).

Fakhari et al., "Lipregulation of Vas cular Endothelial Growth Factor Receptors is Associated with Advanced Neuroblastoma," Journal of Pediatric Surgery, 37(4): 582-587 (Apr. 2002).

Favaro et al., "Targeted therapy in renal cell carcinoma," Expert Opin. Investig. Drugs 14(10):1251-1258 (2005).

Fiedler et al. "A phase 2 clinical study of SU5416 in patients with refractory acute myeloid leukemia," Blood. 102(8): 2763-2767(prepublished online Jul. 3, 2003).

Feldmann, "Pathogenesis of arthritis: recent research progress," Nature Immunology 2001, Vol, 2, No. 9. pp. 771-771.

Fields Virology Second Editon, "Contents,":vol. 1, pp. ix-xiv, Raven Press, NY (1990).

Flaherty et al., "A Phase I Trial of the Oral, Multikinase Inhibitor Sorafenib in Combinatiot with Carboplatin and Paclitaxel" Clin Cancer Res 41(15).4836-4842 (Aug. 1, 2008).

Flaherty et al., "Phase I/II trial of Bay 43-9006 carboplatin (C) and paclitaxel (P) demonstrates preliminary antitumor activity in the expansion cohort of patients with metastatic melanoma." Journal of Clinical Oncology, 2004 ASCO annual meeting proceedings, vol. 22, No. 14S (2004) Supplement: 7507, 4 pages.

Flaherty et al., "Antisense therapeutics: lessons from early clinical trials," Current Opin. in Oncol. 13: 499-505 (2001).

Foekens et al., "High Tumor Levels of Vascular Endothelial Growth Factor Predict Poor Response to Systemic Therapy in Advanced Breast Cancer," *Cancer Research*, 2001, vol. 61, pp. 5407-5411.

Forbes et al., "$N$ -(1-Methyl-5-indolyl)-$N$ '-(3-methyl-5-isothiazolyl)urea: A Novel, High-Affinity 5-HT$_{2B}$ Receptor Antagonist," Journal of Medicinal Chemistry, 1995, vol. 38, No. 6, pp. 855-857.

Franco et al., "Dissolution properties and anticonvulsant activity of phenytoin-polyethylene glycol 6000 and -polyvinylpyrrolidone K-30 solid dispersions," International Journal of Pharmaceutics 225 (2001) pp. 63-73.

Fridman et al., "The Minimal Fragments of c-Raf-1 and NF1 That Can Suppress v-Ha-Ras-Induced Malignant Phenotype," The Journal of Biological Chemistry, vol. 269, No. 48, 1994, pp. 30105-30108.

(56) References Cited

OTHER PUBLICATIONS

Garcia-López et al., "New Routes for the Synthesis of Pyrrolo[3,2-*d*]- and [2,-*d*]-pyrimidine Systems starting from a Common Pyrrole Derivative," Journal of the Chemical Society, Perkin Transactions 1: Organic and Bio-Organic Chemistry (1972-1999), 1978, pp. 483-487.

Gatzemeier et al., "Phase II trial of single-agent soratenib in patients with advanced non-small cell lung carcinoma," Journal of Clinical Oncology, 2006 ASCO Annual Meeting Proceedings Part I. vol. 24, No. 18S (Jun. 20 Supplement) 2006, abstract No. 7002, 4 pages.

Geiger et al., "Antitumor Activity of a C-raf Antisense Oligonucleolide in Combination with Standard Chemotherapeutic Agents against Various Human Tumors Transplanted Subcutaneously into Nude Mice," Clinical Cancer Research vol. 3, 1179-1185, Jul. 1997.

Geng et al., "A Specific Antagonist of the p110δCatalytic Component of Phosphatidylinositol 3'-Kinase, IC486068, Enhances Radiation-Induced Tumor Vascular Destruction," Cancer Research, 64, Jul. 2004, pp. 4893-4899.

Gennaro, Alfonso R. "Table of Contents," pp. xiv-xv, in Remington: The Science and Practice of Pharmacy, 20TH Ed. Remington. Lippincott Williams & Wilkins, 2000.

George et al., "VEGF-A, VEGF-C and VEGF-D in Colorectal Cancer Progression," Neoplasia, 3(5): 420-427 (2001).

George et al., "Prognostic Significance of Plasma Vascular Endothelial Growth Factor Levels in Patients with Hormone-refractory Prostate Cancer Treated on Cancer and Leukemia Group B 9480," Clinical Cancer Research, 7: 1932-1936 (Jul. 2001).

Abou-Alfa et al., "Phase II Study of Sorafenib in Patients with Advanced Ilepatoceidular Carcinoma" Journal of Clinical Oncology, vol. 24, No. 26, pp. 4293-4300 (Sep. 10, 2006).

Giambartolomei et al., "Sustained activation of the Rai/MEK/Erk pathway in response to EGF in stable cell lines expressing the Hepatitis C Virus (HCV) core protein," Oncogene, Nature Publishing Group, 2001: vol. 20, pp, 2606-2610.

Gills et al., "'The development of phosphatidylinositol ether lipid analogues as inhibitors of the serine/threonine kinase, Akt," Expert Opin. Investig. Drugs, vol. 13, No. 7, 2004, pp. 787-797.

Gollob, "Sorafenib: scientific rationales for single-agent anti combination therapy in clear-cell renal cell carcinoma" Pub Med PMID: 16425993, Clin. Genitourin. Cancer 4(3):167-174 (2005) abstract.

Gómez-Esquer et al., "MRNA expression of the angiogenesis markers VEGF and CD105 (endoglin) in human breast cancer," Anticancer Res., 200z1, vol. 24, No. 3a, pp. 1581-1585, XP-002455577, abstract.

Grant et at., "Some Hypotensive Thiadiazoles," J. Med. Chem. (1972), 15(10), pp. 1082-1054.

Greene et al., "Contents," pp. xi-xii, in: Protective Groups in Organic Synthesis, 3rd Ed. John Wiley & Sons, Inc., New York, 1999.

Gelasser, "The Importance of Solvates," in: Polymorphism in the Pharmaceutical Industry, Chapter 8, p. 211, 2006, Wilev-VCH Verlug GmbH & Co., KGaA, Weinhelm.

Gridelli et al, "Sorafenib and Sunitinib in the Treatment of Advanced Non-Small Cell Lung Cancer" The Oncologist (2007) 12:191-200.

Guan et al., "H5N1 influenza: A protean pandemic threat," Proc. Natl. Acad. Sci. USA, May 25, 2004; vol. 101,pp. 8156-8161.

Gupta et al., "Sorafenib targets BRAF and VEGFR in metastatic thyroid carcinoma" Journal of Clinical Oncology, 2007 ASCO Annual Meeting Proceedings (Post-Meeting Edition) vol. 25, No. 18S (Jun. 20 Supplement), 2007: 6019 abstract.

Gura, "Systems for identifying new drugs are often faulty." Science, 1997, vol. 278, (5340), pp. 104-1042, MEDLINE with Full text.

Hahn et al., "Sorafenib," Curr. Opin. Oncol., 18:615-621 (2006).

Hall-Jackson et al., "Paradoxical activation of Raf by a novel Raf inhibitor," Chemistry & Biology, 6: 559-568 (Jul. 1999).

Han et al., "Targeted Prodrug Design to Optimize Drug Delivery." AAPS Pharmsci. 2000: vol. 2, No. 1, Article 6, 1-11.

Hanna, "Second-Tine Treatment of Non-small Cell Lung Cancer: Big Targets, Small Progress; Small Targets, Big Progress?" Journal of Thoracic Oncology vol. 1, No. 9. pp. 927-928 (Nov. 2006).

Hansch et al., "Contents." 21 pages, in: Comprehensive Medicinal Chemistry. The Rational Design, Mechanistic Study & Therapeutic Application of Chemical Compounds, Pergamon Press, Oxford, UK, 1990.

Hanson, "Pulmonary-Allergy, Dermatological, Gastrointestinal & Arthritis, inhibitors of p38 kinase," Exp. Opin. Ther. Patents, 1997, vol. 7, No. 7, pp. 729-733.

Hardmann et al., excerpts from chapter 3. Principles of Therapeutics, in: Goodman & Gilman' The Pharmacological Basis of Therapeutics, 9th ed., 1996, pp. 51 and 57-58.

Harris Fil et al., "Soluble Tie2 and Fltl Extracellular Domains in Serum of Patients with Renal Cancer and Response to Antiangiogenic Therapy," Clin. Cancer Res. 7:1992-1997 (2001).

Hayes et at., "Serum vascular endothelial growth factor as a tumour marker in soft tissue sarcoma," British Journal of Surgery, 91:242-247 (Published on-line Nov. 24, 2003).

Hegedus, L.S. "Contents," 4 pages in: Transition Metals in the Synthesis of Complex Organic Molecules, University Science Books, Mill Valley, California, 1994.

Heim et al., "Antitumor effect and potentiation or reduction in cytotoxic drug activity in human colon carcinoma cells by the Raf kinase inhibitor (RKI) BAY 43-9006," International Journal of Clinical Pharmacology and Therapeutics, 2003 vol. 41, No. 12, pp. 616-617.

Heim et al., "The Raf kinase inhibitor BAY 43-9006 reduces cellular uptake of platinum compounds and cytotoxicity in human colorectal carcinoma cell lines," Anti-Cancer Drugs, 2005, vol. 16, pp. 129-136.

Herlaar et al., "p38 MAPK signalling cascades in inflammatory disease," Molecular Medicine Today, vol. 5, pp. 439-447 (Oct. 1999).

Herrera et al., "Unraveling the complexities of the Raft/MAP kinase pathway for pharmacological intervention," Trends in Molecular Medicine, 2002, vol. 8, No. 4 (Supp.), pp. S27-S31.

Higuchi T. et al., "Contents," in: Prodrugs as Novel Drug Delivery Systems, Acs Symposium Series 14, American Chemical Society, Washington, DC, 1975, p. vii.

Higuchi et al, "Mitochondrial DNA determines androgen dependence in prostate cancer cell lines," Oncogene, 2006, vol. 25, pp. 1437-1445.

Hilger et al., "Correlation of ERK-phosphorylation and toxicities in patients treated with the Raf kinase inhibitor BAY 43-9006" international Journal of Clinical Pharmacology and Therapeutics, vol. 42, No. 11, pp. 648-649 (2004).

Hilger et al., "ERK1/2 phosphorylation: a biomarker analysis within a phase I study with the new Raf kinase inhibitor BAY 43-9006" International Journal of Clinical Pharmacology and Therapeutics, vol. 40, No. 12, pp. 567-568 (2002).

Hilger et al., "Inhibition of ERK phosphorylation and clinical outcome in patients treated with the Raf kinase inhibitor BAY 43-9006" Proc Am Soc Clin Oncol 21: 2002 (abstr 1916), 3 pages.

Hirasawa et al., "Effect of p38 Mitogen-Activated Protein Kinase on the Replication of Encephalmyocarditis Virus." Journal of Virology, May 2003: vol. 77, No.10, pp. 5649-5656.

Holmlund et al., "Phase I Trial of C-raf Antisense Oligonucleotide ISIS 5132 (CGP 69846A) By 21-Day Continuous intravenous Infusion (CIV) In Patients With Advanced Cancer," (Meeting abstract), 1998 ASCO Annual Meeting, Abstract No. 811, 2 pages.

H otte et al., "BAY 43-9006: Early clinical data in patients with advanced solid malignancies," Current Pharmaceutical Design, 8: 2249-2253, 2002.

Hu et al., "Soluble Vascular Endothelial Growth Factor Receptor I. And Not Receptor 2, Is an Independent Prognostic Factor in Acute Myeloid Leukemia and Myelodyslastic Syndromes," Cancer, 100(9): 1884-1891 (Published on-line Mar. 29, 2004).

Hubbard, "Oncogenic Mutations in B-Raf: Some Losses Yield Gains," Cell vol. 116, Issue 6, 764-766 (2004).

Hyodo et al.,"Clinical Significance of Plasma Vascular Endothelial Growth Factor in Gastrointestinal Cancer," European Journal of Ganser, 34(13): 2041-2045 (1998).

Ihle et al., "Molecular pharmacology and antitumor activity of PX-866, a novel inhibitor of phosphoinositide-3-kinase signaling," Molecular Cancer Therapy, vol. 3, No. 7, 2004, pp, 763-772.

(56) References Cited

OTHER PUBLICATIONS

Ishigami et al., "Predictive value of vascular endothelial growth factor (VEGF) in metastasis and prognosis of human colorectal cancer," British Journal of Cancer, 78(10): 1379-1384 (1998).

Jacobsen et al., "Vascular Endothelial Growth Factor as Prognostic Factor in Renal Cell Carcinoma," Journal of Urology, 163(1): 343-347 (Jan. 2000).

Jacobsen et al., "Prognostic importance of serum vascular endothelial growth factor in relation to platelet and leukocyte counts in human renal cell c m arcinoa," European Journal of Cancer Prevention, 2002, 11(3) pp. 245-252.

Jain et al., "Randomized Discontinuation Trial of Sorafenib (BAY 43-9006)," Cancer Biology & Therapy, vol. 5, Issue 10, pp. 1270-1272 (2006).

Jeffcoat et al., "The Metabolism and Toxicity of Halogenated Carbanilides," Drug Metabolism and Disposition, vol. 5, No. 2, pp. 157-166 (1977).

Jimeno et. al., "Analysis of Biologic Surrogate Markers from a Children's Oncology Group Phase 1 Trial of Gefitinib in Pediatric Patients with Solid Tumors," Pediatr. Blood Cancer, 49(3): 352-357 (2007).

Jin et al., "Inhibition of AKT survival pathway by a small molecule inhibitor in human endometrial cancer cells," British Journal of Cancer vol. 91, 2004, pp. 1808-1812.

Johnson et al., "Relationships between drug activity in NCI preclinical in vitro and in vivo models and early clinical trials," British Journal of Cancer, 2001, vol. 84, No. 10, pp. 1424-1431.

Johnston, D, et al., "Elevation of the Epidermal Growth Factor Receptor and Dependent Signaling in Human Papillomavirus-infected Laryngeal Papillomas," Cancer Research, 1999: vol. 59, pp. 968-974.

Jungmayr, P., "Aktueller Stand der Krebstherapie," Deutsche Apotheker Zeitung, Sept 30, 2004, Auflage ca. 36.000.

Kapoun et al., "TGFβR1 kinase activity, but not p38 activation is required for TGFβR1 inducedmyofibroblast differentiation and profibrotic gene expression," Molecular Pharmacology Fast Forward, abstract, 2006, www,molpharmaspetjournals.org, 2 pages.

Karayiannakis et al, "Circulating VEGF Levels in the Serum of Gastric Cancer Patients," Annals of Surgery, 236(1): 37-42 (Jul. 2002).

Karayiannakis et al "Clinical significance of preoperative serum vascular endothelial growth factor levels in patients with colorectal cancer and the effect of tumor surgery," Surgery, 131(5): 548-555 (May 2002).

Karp et al., "Targeting Vascular Endothelial Growth Factor for Relapsed and Refractory Adult Acute Myelogenous Leukemias: Therapy with Sequential 1-β-D Arabinofuranosylcytosine, Mitoxantrone, and Bevacizumab," Clinical Cancer Research, 10: 3577-3585 (Jun. 1, 2004).

Katritzky et al,, "1.18. Azetidines, Azetines, and Azetes: Monocylcic" pp. 507-508 in: Comprehensive Heterocyclic Chemistry II, A Review of the Literature 1982-1995: The Structure, Reactions, Synthesis, and Uses of Heterocyclic Compounds. Pergamon Press, Oxford, UK, 1996.

Katritzky,Alan R. Tables of Content, in: Comprehensive Organic Functional Group Transformations, Pergamon Press, Oxford, UK, 1995, 25 pages.

Katritzky et al., "Contents," 2 pages in: Comprehensive Heterocyclic Chemistry, The Structure, Reactions, Synthesis, and Uses of Heterocyclic Compounds. Pergamon Press, Oxford, UK, 1984.

Keller et al., "The role of Raf kinase inhibitor protein (RKIP) in health and disease," Biochemical Pharmacology 68; pp. 1049-1053 (2004).

Kempter et al., "Synthese potentieller Pflanzenschutz- und Schädlingsbekampfungsmittel aus substituierten Anilitien," Pädagogsische Hochschule, Eingegangen am 1.7.1982, vol. 27, Issue 1, 101-120 (1983).

Kessler et al., "Use of the DNA Flow-Thru Chip, a Three-Dimensional Biochip, for Typing and Subtyping of Influenza Viruses." Journal of Clinical Microbiology. May 2004: vol. 42, pp. 2173-2185.

Mtire et al., "Omega-carboNypyridyl substituted ureas as Raf kinase inhibitors: SAR of the amide substituent," Bioorg. Med. Chem. Lett., 2004, vol. 14, pp. 783-786.

Kido, Y., "Vascular Endothelial Growth Factor (VEGF) Serum Concentration Changes during Chemotherapy in Patients with Lung Cancer," Kurume Medical Journal, 48(1): 43-47 (2001).

Klemm et al., "Chemistry of Thienopyridines, XXXVII. Syntheses in the Cyclopenta. Cyclohexa-, and Cycloheptathieno [2,-b ]pyridine Series. Threee Analogs of 9-Amino-1,2,3,4-tetrahydroacridine [1]," J. Heterocyclic Chem., 27, 1990, pp. 1537-1541.

van Muijlwijk-Koezen et al., "Isoquinoline and Quinazohne Urea Analogues as Antagonists for the Human Adenosine $A_3$ Receptor," J. Med. Chem. 2000, 43, pp. 2227-2238.

Kolch et al., "Raf-1 protein kinase is required for growth ot induced NIH-1/3T3 cells," Nature, Voi. 349, Jan. 31, 1991. pp. 426-428.

Kolch et al., "The role of Raf kinases in malig,nallt transformation" Expert reiews in molecular medicine (Apr. 25, 2002) ISSN: 1462-3994 © Cambridge University Press. 18 pages.

Konecny et al., "Association between HER-2/*neu* and Vascular Endothelial Growth. Factor Expression Predicts Clinical Outcome in Primary Breast. Cancer Patients," Clinical Cancer Research, 10: 1706-1716 (Mar. 1, 2004).

Korfee et al., "New targeted treatments in lung cancer-overview of clinical trials," Lung Cancer, 45 (Suppl. 2): S199-S208 (2004).

Kraft et al., "Vascular Endothelial Growth Factor in the Sera and Effusions of Patients with Malignant and Nonmalignant Disease," Cancer, 85(1): 178-187 (Jan 1, 1999).

Kubo et al., "Herbicidal Activity of 1,3,4-Thiadiazole Derivatives," J. Agr. Food Chem. (1970), 18(1), pp. 60-65.

Kubo et al., "Synthesis and structure-activity relationship of quinazoline-urea derivatives as novel orally active VEGF receptor tyrosine kinase selective inhibitors," Proceedings of the American Association of Cancer Res., 2002, vol. 43, p. 182, abstract No. 913.

Kuefer et al., "Translational research in renal cell cancer. Illustrated by the example of the vascular endothelial growth factor pathway," Der Urologe, 2006, vol. 45, No. 3, pp. 328, 330-335.

Kumar et al., "Drugs targeted against protein kinases" Expert Opin. Emerging Drugs 6(2):303-315 (2001).

Kupsch et al., "Results of a Phase I Trial of Sorafenib BAY 43-9006) in Combination with Oxaliplatin in Patients with Refractory Solid Tumors, including Colorectal Cancer," Clinical Colorectal Cancer, Cancer information Group journal, vol. 5 Issue 3, pp. 188-196, abstract (Sep. 2005).

Kurik et al', "Optical Properties of Segmented Oligourethane with Atomethine Terrain,. Fragments," Polymer Science. series B, 1996, vol. 38 pp. 2038-2041.

Kyriakis et al., "Raf-1 activates 'MAP kinase-kinase" Nature. 358, 6385, pp. 417-421 (Jul. 30, 1992).

Laack et al., "Pretreatment serum levels of matrix metalloproteinase-9 and vascular endothelial growth factor in non-small-cell lung cancer," Annals of Oncology, 13(10): 1550-1557 (Oct 2002).

Dal Lago et al., "Selected Combination therapy with Soralenib: A Review of Clinical Data and Perspectives in Advanced Solid Tumors" The Oncologist, vol. 13, No. 8, pp. 845-858 (Aug. 11, 2008).

Lau et al., "Abrogation of c-Raf expression induces apoptosis in tumor cells," Oncogene 16, 1899-1902 (1998).

Lee et al., "BAY-43-9006 Bayer/Onyx," Current Opinion in Investig .tional Drugs, 2003, vol. 4, No. 6, pp. 757-763.

Lee et al., "Bicyclic Imidazoles as a Novel Class of Cytokine Biosynthesis Inhibitors," Annals N.Y. Academy of Science, 1993, vol. 696, pp. 149-170.

Lee et al.: "FTY720 induces apoptosis of human hepatoma cell lines through PI3-K-mediated Akt dephosphorylation," Carcinogenesis, vol. 25, No. 12, 2004, pp. 2397-2405.

Lee et al., "Prognostic value of vascular endothelial growth factor expression in colorectal cancer patients," European Journal of Cancer, 36(6): 748-753 (Apr. 2000).

Lee and Heymach, "Emerging Antiangiogenic Agents in Lung Cancer," Clinical Lung Cancer, 7(5): 304-308 (Mar. 2006).

(56) References Cited

OTHER PUBLICATIONS

Legros et al., "Imatinib mesylate (STI571) decreases the vascular endothelial growth factor plasma concentration in patients with chronic myeloid leukemia," Blood, 104(2): 495-501 (Prepublished on-line Feb. 19, 2004).
Lemoine, "Overview of *ras* oncogenes and their clinical potential," Chapter 10, In: Mutant Oncogenes: Targets for Therapy? (eds. Lemoine NR & Epenetos A), Chapman & Hall, London. pp. 85-91; 2004.
Lepage et al., "New N-aryl isoxazolecarboxamides and N-isc. zolybenzamides as anticonvulsant agents," *Eur. J. Med. Chem.*, vol. 27, 1992, pp. 581-593.
Leaner et al., "Improving drug solubility for oral delivery using solid dispersions," European Journal of Pharmaceutics and Biopharmaceutics, 50, 2000, pp. 47-60.
Liang et al., "Differential Expression of VEGF and Its Receptors in the Primary Cells of Various Risk Classified Acute Lymphoblastic Leukemia Patients," Blood 104: Abstract 4446 (2004).
Li et al. "Correlation of Serum Vegf Levels with Clinical Stage, Therapy Efficacy, Tumor Metastasis and Patient Survival in Ovarian Cancer," Anticancer Research, 24: 1973-1980 (2004).
Lin, "Synthesis of 1-(2-Pyridine-1-oxide)-2-(1-Methv 1-2-Pyridinium)-Ethane Chloride," OPPI Briefs, vol. 23, No. 1, 1991, pp. 114-115.
Linderholin et al., "Correlation of Vascular Endothelial Growth Factor Content with Recurrences, Survival, and First Relapse Site in Primary Node-Positive Breast Carcinoma After Adjuvant Treatment," Journal of Clinical Oncology, 18(7): 1423-1431 (Apr. 2000).
lLinderholm et al., "p53 and Vascular-Endothelial-Growth-Factor (VEGF) Expression Predicts Outcome in 833 Patients with Primary Breast Carcinoma," Int. J. Cancer (Pred. Oncol.): 89(1): 51-62 (2000).
Lissoni et al., "Anti-angiogenic activity of melatonin in advanced cancer patients," Neuroendocrinology Letters, 2001, 22:45-47.
Lissoni et al., "Chemotherapy and angiogenesis in advanced cancer: vascular endothelial growth factor (VEGF) decline as predictor of disease control during taxol therapy in metastatic breast cancer," International Journal of Biological Markers, 15(4): 308-311 (Oct. 1, 2000).
Lissoni et al., "Abnormally enhanced blood concentrations of vascular endothelial growth factor (VEGF) in metastatic cancer patients and their relation to circulating dendritic cells, IL-12 and endothelin-1," Journal of Biological Regulators and Homeostatic Agents, 15(2): 140-1,14 (Apr. 2001).
Lissoni et al., "Changes in circulating VEGF levels in relation to clinical response during chemotherapy for metastatic cancer," International Journal of Biological Markers, 18(2): 152-155 (2003).
Llovet et al., "Molecular Targeted Therapies in Hepatocellular Carcinoma," .Hepatology, vol. 48, No. 4, pp. 1312-1327, 2008.
Lockhart et al., "Phase I/Pilot Study of SU5416 (Semaxinib) in Combination With Irinotecan/Bolus 5-FU/LV (IFL) in Patients With Metastatic Colorectal Cancer," American Journal of Clinical Oncology, 29(2):109-115 (Apr. 2006).
Lorigan et al., "Phase II trial of sorafenib combined with dacarbayine in metastatic melanoma patients" ASCO 2006 DTIC abstract, 2 pages (Jan. 11, 2006).
Lowinger et al., "Design and Discovery of Small Molecules Targeting Raf-1 Kinase," Current Pharmaceutical Design, 2002, vol. 8, pp. 2269-2278.
Lowinger et al., "Discovery of novel class of potent Raf kinase inhibitors: structure activity relations is " Clinical Cancer Research, Nov. 2000, vol. 6 (Supp.), p. 4533s, abstract No. 335.
Lowy et al "Function and Regulation of RAS" Annual Review of Biochemistry, vol. 62, pp. 851-891, 1993.
Ludwig et al., "MEK inhibition impairs influenza B virus propagation without emergence of resistant variants," FEBS Letters, 2004, vol. 561, pp. 37-43.
Luo et al.,nh , "Enhancement of radiation effects by pXLG-mENDO in a lung carcinoma model," Int. J. Radiation Oncology Biol. Phys., 2005, vol. 63, No. 2, pp. 553-564.

Lyons et al., "Discovery of a novel Raf kinase inhibitor," *Endocrine-Related Cancer*, 2001, vol. 8. pp. 219-225.
Madwed et al., "Pharmacological evaluation of BIRB 796, a selective inhibitor of p38 MAP kinase (MAPK), in animal models of endotoxic shock, inflammation and arthritis," Inflammation Res., 50:5184, abstract No. W22/03, 2001.
Magnuson et al., "The Raf-1 serinetthreonine protein kinase," Cancer Biology, vol. 5, 1994, pp. 247-253.
Manenti et al., "Circulating plasma vascular endothelial growth factor in mice bearing human ovarian carcinoma xengraft correlates with tumor progression and response to therapy," Molecular Cancer Therapeutics, 4(5): 715-725 (May 2005).
Mannováet al., "Activation of the N-Ras-P13K-Akt-mTOR Pathway by Hepatitis C Virus: Control of Cell Survival and Viral Replication," Journal of Virology, Jul. 2005, vol. 79, No. 14, pp. 8742-8749.
Markgraf et al., "Strained Heterocyclic Systems. 19. 1-Azatriptycene and Derivatives," Tetrahedron. vol. 47, No. 2, 1991, pp. 183-188.
Marshall, "MAP kinase kinase kinase, MAP kinase kinase, and MAP kinase," Curr. Opin. Genet. Dev. 4: 82-89. 1994.
Marx, J., "Why a New Cancer Drug Works Well, in Some Patients." Science, vol. 304, pp. 658-659, 2004.
McGoon et al, "Screening, Early Detection, and Diagnosis of Pulmonary Arterial Hypertension " CHEST, 2004: 126, pp. 14S-34S.
Medinger et al., "Hemmung der Tumorangiogenese Neue Therapieoptionen in der Onkologie,"Med Welt, 2006, 57, pp. 437-441.
Med Report Deutschland, "Sorafenib zur Therapie des fortgeschrittenen Nierenzelikarzinoms zugelassen," (2006), 1 page.
Meuillet et al., "In Vivo Molecular Pharmacology and Antitumor Activity of the Targeted Akt Inhibitor PX-316," Oncology Research, vol. 14, 2004, pp. 513-527.
Michaelis, "Phenylharnstoff des 1-Phenyl-3- ethyl-5-aminopyrazols."Justus Liebigs Ann. Chem. (JLACBF) 397, 1913, p. 143.
Milanini et al., "p42/p41 MAP Kinase Module Plays a Key Role in the Transcriptional Regulation of the Vascular Endothelial Growth Factor Gene in Fibroblasts," Journal of Biological Chemistry, 273(29): 18165-18172 (Jul. 17, 1998).
Milano et al., "New molecular targeted therapies in thyroid cancer" Anti-Cancer Drugs (2006) © Lippincott Williams & Wilkins vol. 17:869-879.
Mills et al., "The Effects of Standard Anthracycline-Based Chemotherapy on Soluble ICAM-1 and Vascular Endothelial Growth Factor Levels in Breast Cancer," Clinical Cancer Research, 10: 4998-5003 (Aug. 1, 2004).
Milojokovic et al.. "limmunohistochemical Characterisation of Vascular Endothelial Growth Factor (VEGF) and its Receptors Flt-1 and KDR in Chronic Myeloid Leukaemia (CML) Patients Treated with Imatinib Mesylate," Blood, 104 Abstract 1999 (2004).
Minna et al., "A Bull's Eye for Targeted Lung Cancer Therapy," Science, vol. 304, pp. 1458-1460, 2004.
Mita et al., "The Molecular Target of Rapamycin (mTOR) as a Therapeutic rget Against angainst Cancer." Biology & Therapy 2:4 Suppl. 1, S169-S177 (Jul./Aug. 2003).
Moelling et al., "Signal E'ransuction as Target of Gene Therapy," Institute of Medical Virology, University of Zurich, Recent Results in Cancer Research, vol. 142, pp. 63-71 (1996).
Molhoek et al., "Synergistic inhibition of human melanoma proliferation by combination treatment with B-Raf inhibitor BAY 43-9006 and mTOR inhibitor rapamycin," Journal of Translational Medicine (2005) 3:39, pp. 1-11.
Monia, "First-and second-generation antisense oligonucleotide inhibitors targeted against human c-*raf* kinase," (1997) Oligonucleotides as therapeutic agents Wiley, Chichester (Ciba Foundation Symposium 209) pp. 107-123.
Monia et al "Antitumor activity of a phosphorothioate antisense oligodeoxynucleotide targeted against C-*raf* kinase," Nature Medicine, Vol. 2, No. 6, Jun. 1996, pp. 668-675.
Monia et al., "Sequence-specific antitumor activity of a phosphorothioate oligodeox)fribonucleotide targeted to human C-*raf* kinase supports and antisense mechanism of action *in vivo*," Proc. Natl. Acad. Sci USA, vol. 93, 15481-15484 (Dec, 1996).

(56) References Cited

OTHER PUBLICATIONS

Morabito et al., Tyrosine Kinase Inhibotors of Vascular Endothelial Growth Factor Receptors I Clinical Trials: Current Status and Future directions, The Oncologist, 11: 753-764 (2006).
Mori et al., "Differential activation of the c-Jun N-terminal kinase/stress-activated protein kinase and p38 mitogen-activated protein kinase signal transduction pathways in the mouse brain upon infection with neurovirulent influenza A virus," Journal of General Virology, 2003. 84, pp. 2401-2408.
Moore et al., "Phase I study to determine the safety and pharmacokinetics of the novel Raf kinase and VEGFR inhibitor BAY 43-9006, administered for 28 days on/7 days off in patients with advanced, refractory solid tumors," Annals of Oncology, 2005, vol. 16, pp. 1688-1694.
Motzer et al., "Survival and Prognostic Stratification of 670 patients With Advanced Renal Cell Carcinoma", J. Clin. Oncol., 17(8):pp. 2530-2540 (1999).
Mross et al., "Drug-drug interaction pharmacokinetic study with the Raf kinase inhibitor (RKI) BAY 43-9006 administered in combination with irinotecan (CPT-11) in patients with solid tumors," International Journal of Clinical Pharmacology and Therapeutics, 2003, vol. 41, No. 12, pp. 618-619.
Mross et al., "Results from an in vitro and a clinical/pharmacological phase I study with the combination irinotecan and sorafenib" European Journal of Cancer 43, pp. 55-63 (2007).
Murata et al, "Facile Synthesis of New Pyrrolo[3,4-d]pyrimidine-2,4-diones," Chemical and Pharmaceutical Bulletin, vol. 22, No. 5, 1974, pp. 1212-1213.
Murphy et al., "BAY 43-9006 controls tumor growth through inhibition of vascular development," 96$^{th}$ Annual Meeting, Anaheim/Orange County, CA, Apr. 16-20, 2005, abstract No. 2985.
Muthumani et al., "Suppression of HIV-1 viral replication and cellular pathogensis by a novel p38/JNK kinase inhibitor," AIDS Lippincott Williams & Wilkins. 2004: vol. 18, pp. 739-748.
National Cancer Institute, "Carboplatin and Paclitaxel With or Without Somfenib in Treating Patients With Unresectable Stage III or Stage IV Melanoma", 7 pages NCT00110019, clinicaltrials.gov. (2005).
National Cancer Institute, "Paclitaxel, Carboplatin, and Radiation Therapy in Treating Patients Who Are Undergoing Surgery for Stage III Non-Small Cell Lung Cancer," 5 pages, NCT00096226, (2005).
National Cancer institute, "Sorafenib With or Without Paclitaxel and Carboplatin in Treating Patients With Recurrent Ovarian Cancer, Primary Peritoneal Cancer, or Fallopian Tube Cancer," 5 pages, NCT00096200, (2005).
National Cancer institute. Clinical Trials (PDQ®), "Phase II Randomized Study of ISIS 5132 or ISIS 3521 in Women with Previously Treated Metastatic Breast Cancer," 3 pages, www.cancer.gov website (1998).
National Cancer institute, Clinical Trials (PDQ®), "Phase II Randomized Study of ISIS 3521 and ISIS, 5132 for Locally Advanced or Metastatic Colorectal Cancer," 3 pages, www.cancer.gov website (1998).
National Cancer institute, Clinical Trials (PDQ®), "Phase II Randomized Study of Sis and ISIS 5132 in Patients with Hormone Refractory Prostate Cancer," 3 pages, www.cancer.gov website (1998).
National. Cancer institute, Clinical Trials (PDQ®), "Phase II Study of ISIS 5132 in Patients with Advanced Pancreatic Cancer," 3 pages, www.cancer.gov website (1999).
National Institutes of Health Clinical Center, "BAY 43-9006 (Sorafenib) to Treat Relapsed Non-Small Cell Lung Cancer", 4 pages, NCT00098254, clinicaltrials.gov (2005).
Naumann et al., "Raf protein serine/threonine kinases" in: Protein Phosphorylation, VCH Verlagsgesellschaft mbH Chapter 7, pp. 203-236 (1996).
Naumann et al.. "The Role of Raf Kinases in Development and Growth of Tumors" Recent Results in Cancer Cancer Research. vol. 143, pp. 237-244 (1997).

Nemunaitis et al., "Phase I Evaluation of ISIS 3521, an Antisense Oligodeoxynucleotide to Protein Kinase C-Alpha, in Patients with Advanced Cancer" Journal of Clinical Oncology, vol. 17, No. 11, pp. 3586-3595 (Nov. 1999).
Neufeld et al, Vascular endothelial growth factor (VEGF) and its receptors, The FASEB Journal, 13: 9-22 (Jan. 1999).
"Nexavar Receives FDA Fast Track Designation for Skin Cancer" 4 pages, (Jul. 21, 2006) http://www.medicalnewstoday.com/articles/47793.php (last visited on Jun. 16, 2008).
Nicholson, K. M. et al,: "the protein kinase B/Akt signalling pathway in human malignancy," Cellular Signalling 14, 2004, pp. 381-395.
Nickel et al., "Carboxylic acid analogues of suramin, potential filaricides," Indian Journal of Chemistry, Feb. 1991, vol. 30B, pp. 182-187.
Nilsson et al., "Vascular Endothelial Growth Factor (VEGF) Pathway," Journal of Thoracic Oncology, 1(8): 768-770 (Oct. 2006).
Noble et al., "Protein Kinase Inhibitors: Insights into Drug Design From Structure," Science, (2004), vol. 303, pp. 1800-1805.
O'Dwyer et al., "c-raf-1 Depletion and Tumor Responses in Patients Treated with the c-raf-1 Antisense Oligodeoxynucleotide ISIS 5132 (CCGP 69846A)," Clinical Cancer Research vol. 5, pp. 3977-3982 (Dec. 1999).
Oka et al., Constitutive Activation of Mitogen-activated Protein (MAP) Kinases in Human Rental Cell Carcinoma,"" Cancer Research 55, pp. 4182-4187, (Sep. 15, 1995).
Gollob et 211., "Phase II trial of sorafenib (BAY 43-9006) in combination with interferon alpha 2b in patients with metastatic renal cell carcinoma," European Journal of Cancer, 2005, vol. 3, No. 2, pp. 226227. abstract No. 795.
Osella-Abate et al., "VEGF-165 serum levels and tyrosinase expression in melanoma patients: correlation with the clinical course," Melanoma Research, 12: 325-334 (Aug. 2002).
Oza et al., "Phase II study of CGP 69846A (ISIS 5132) in recturent epithelial ovarian cancer: an NCIC clinical trials group study (NCIC IND .116)," PubMed Abstract 12694666, Gynecol. Oncol. 2003 Apr: 89(1):129-133.
Ozols, "New Developments With Carboplatin in the Treatment of Ovarian Cancer." *Seminars in Oncology*, vol. 19, No. 1, Supplement 2, Feb. 1992, pp. 85-89.
Panka et al., "BAY 43-9006 induces apoptosis in melanoma cell lines," 96$^{th}$ Annual Meeting, Anaheim/Orange County, CA, April 16-20, 2005, abstract No. 5328.
Panteva et al., "Hepatitis viruses and the MAPK pathway: is this a survival strategy?" Virus Research, 2003, vol. 92: 131-140.
Paquette, Table of Contents for The Encyclopedia of Reagents for Organic Synthesis, John Wiley, New York, 1994 Table of Contents.
Paviović-Lažetićet al., "Bioinformatics analysis of SARS coronavirus genome polymorphism," May 5, 2004, BMC Bioinformatics, vol. 5:65, 14 pages.
Pederson et al., "Early changes in serum IL-6 and VEGF levels predict clinical outcome following first-line therapy in aggressive non-Hodgkin's lymphoma," Ann. Hematol., 84:510-516 (2005).
Peters, HD., "Sorafenib bei soliden Turnoren," Focus Onkologie, 2007, Auflage 12000, 6 pages.
Robert et al., "Phase I trial of sorafenib (BAY 43-9006) in combination with interferon alpha-2a in patients with unresectable and/or metastatic renal cell carcinoma and malignant melanoma," European Journal of Cancer, 2005, vol. 3, No. 2, p. 254, Abstract 883.
Hu et al., "Soluble Vascular Endothelial Growth Factor Receptor 1, and Not Receptor 2, is an Independent Prognostic Factor in Acute Myeloid Leukemia and Myelodysplastic Syndromes," Cancer 2004, vol. 100, No. 9, pp. 1884-1891.
Raez et al.,"New developments in chemotherapy for advanced non-small cell lung cancer," Current Opin. Oncol., vol. 18, 2006, pp. 156-161.
Rahmani et al., "Apoptosis Induced by the Kinase Inhibitor BAY 43-9006 in Human Leukemia Cells Involves Down-regulation of Mcl-1 through Inhibition of Translation," J. Biol. Chem. 280(42):35217-35227 (2005).
Rak et al., "Oncogenes and Angiogenesis: Signaling Three-Dimensional Tumor Growth," Journal of investigative Dermatology Symposium Proceedings (2000) 5, 24-33.

(56) References Cited

OTHER PUBLICATIONS

Rak et al., "Oncogenes and Tumor Angiogenesis: Differential Modes of Vascular Endothelial Growth Factor Up-Regulation in ras -transformed Epithelial Cells and Fibroblasts," Cancer Research 60, pp. 490-498, (Jan. 15, 2000).
Rak et al., "Oncogenes as inducers of tumor angiogenesis," Cancer and Metastasis Reviews 14: 263-277, 1995.
Sturm-Ramirez et al,. "Reemerging H5N1 Influenza Viruses in Hong Kong in 2002 Are Highly Pathogenic to Ducks," Journal of Virology, 2004-2005, 78(9):4892-4901.
Raposo et al., "Catalysis of Nucleophilic Addition of Pyrrolidine to 2-(5$H$)-Furanone through Chromenone Cleft-Type Receptors," Tetrahedron Letters Vol, 37, No, 38, pp. 6947-6950, 1996.
Ratain et al., "Phase II Placebo-Controlled Randomized Discontinuation Trial of Sorafenib in Patients with Metastatic Renal Cell Carcinoma," Journal of Clinical Oncology vol. 24 No. 16, pp. 2505-2512 (Jun. 1, 2006).
Ravi et al., "Activated Raf-1 Causes Growth Arrest in Human Small Cell Lung Cancer Cells," J. Clin. Invest., vol. 101, No. 1, pp. 153-159 (1998).
Reddy et al., "Sorafenib: recent update on activity as a single agent and in combination with interferon-alpha2 in patients with advanced-stage renal cell carcinoma," Clin. Genitourin. Cancer 4:246-248 (2006) abstract.
Redman et al., "p38 Kinase Inhibitors for the Treatment of Arthritis and Osteoporosis: Thienyl, Furyl, and Pyrrolyt Ureas," iBioorganic & Medicinal Chemistry Letters 11 (2001) 9-12.
Regan et al., "Pyrazole Urea-Based inhibitors of p38 MAP kinase: From Lead Compound to Clinical Candidate," J. Med. Chem. 45:2994-3008, 2002.
Richly et al., "A phase I clinical and pharmacokinetic study of the Raf kinase inhibitor (RKI) BAY 43-9006 administered in combination with doxorubicin in patients with solid tumors," International Journal of Clinical Pharmacology and Therapeutics, 2003, vol. 41, No. 12, pp. 620-621.
Richly et al., "Results of a Phase I trial of sorafenib (BAY 43-9006) in combination with doxorubicin in patients with refractory solid tumors," Annals of Oncology, 2006, 17, pp. 866-873.
Richly et al., "Results of a phase I trial of BAY 43-9006 in combination with doxorubicin in patients with primary hepatic cancer," International Journal of Clinical Pharmacology and Therapeutics, 2004, vol. 42, No. 11, pp. 650-651.
Ridley et al., "Actions of IL-1 are Selectively Controlled by p38 Mitogen-Activated Protein Kinase, Regulation of Prostaglandin H Synthase Metalloproteinases, and IL-6 at Different Levels," The American Association of Immunologists, 1997, J. Immunol. vol. 158, pp. 3165-3173.
Rini and Small "Biology and Clinical Development of Vascular Endothelial Growth Factor-Targeted Therapy in Renal Cell Carcinoma," Journal of Clinical Oncology, 23(5): 1028-1043 (Feb. 10, 2005).
Robak et al., "Vascular endothelial growth factor and its sotuble receptors VEGFR-1 and VEFR-2 in the serum of patients with systemic lupus erythematosus," Mediators of Inflammation 12(5):293-298 (Oct. 2003).
Robertson et al. "HIV-1 Nomenclature Proposal," Science, Apr. 7, 2000, pp. 55-57, vol. 288.
Robinson et al., "Enhanced Radiosensitization with Gemcitabine in Mismatch Repair-Deficient HCT116 Cells," Cancer Research 63, 6935-6941 (Oct. 15, 2003).
Robke et al., "Conversion of Aminopyridines into %V-Oxides by Caro's Acid Anion (Peroxymonosulfate)." J. Chem. Research (S), 1993, pp. 412-413.
Roche, E. B., "Structural Aspects of Selective Distribution," Chapter 3, in: Design of Biopharmaceutical Properties Through Prodrugs and Analogs, American Pharmaceutical Association, Washington, D.C., 1977, pp. 27-46.

Rodriguez et al., "A sensitive fluorometric enzyme-linked immunosorbent assay that measures vascular endothelial growth factor$_{165}$ in human plasma," Journal of Immunological Methods, 219(1-2): 45-55 (Oct. 1998).
Roman et al., "Human Papillomaviruses: Are We Ready to Type?" Clinical Microbiology Reviews. Apr. 1989: vol. 2, pp. 166-190.
Rowinsky et al., "Sequences of Taxol and Cisplatin: A Phase I and Pharmacologic ' dy," Journal of Clinical Oncology, vol. 9, No. 9, Sep. 1991, pp. 1692-1703.
Rowinsky et al., "Taxol: The First of the Taxanes, an Important New Class of Antitumor Agents," *Seminars in Oncology*, vol. 19, No. 6, Dec. 1992, pp. 646-662.
Rubin, Lewis J., "Primary Pulmonary Hypertension," New England Journal of Medicine, vol. 336, No. 2, pp. 111-117 (1997).
Rudin et al., "Phase I Trial of ISIS 5132, an Antisense Oligonucleotide Inhibitor of c-*raf* -1, Administered by 24-hour Weekly Infusion to Patients with Advanced Cancer" Clinical Cancer Research vol. 7, pp. 1214-1220 (May 2001).
Russo et al., "Sintesi Di Derivati 2,6-SostiMiti Del 5H-1,3,4 Tiadiazolo[3,2 a ]s-Triazina,7-Dione," II Farmaco, Ed.Sci. (1978), 33(12), 972-983.
Rydén et al., "Tumor specific VEGF-A and VEGFR2/KDR protein are co-expressed in breast cancer," Breast Cancer Research and Treatment, 82(3):147-154 (Dec. 2003).
Salvatore et al., "BRAF Is a Therapeutic Target in Aggressive Thyroid Carcinoma," Clin. Cancer Res. pp. 16234629; 12(5) (Mar. 1, 2006).
Sarkar et al., "Inodole-3-Carbinol and Prostate Cancer," Journal of Nutrition 13-4, 2004, pp. 3493S-3498S.
Serajuddin, "Solid Dispersion of Poorly Water-Soluble Drugs: Early Promises Subsequent Problems, and Recent Breakthroughs," Journal of Pharmaceutical Sciences vol. 88, No. 10, pp. 1058-1066 (Oct. 1999).
Shaked et al., "Cellular and Molecular Surrogate Markers to Monitor Targeted and Non-Targeted Antiangiogenic Drug Activity and Determine Optimal Biologic Dose," Current Cancer Drug Targets, 5: 551-559 (Nov. 2005).
Shelton et al., "Effects of the RAF/MEK/ERK and PI3K/AKT signal transduction pathways on the abrogation of cytokine-dependence and prevention of apoptosis in hematopoietic cells," Oncogene, vol. 22, No. 16, Apr. 2003; pp. 2478-2492.
Shi et al., "Constitutive and Inducible Interleukin 8 Expression by Hypoxia and Acidosis Renders Human Pancreatic Cancer Cells More Tumorigenic and Metastatic," *Clinical Cancer Research*, 1999, vol. 5, pp. 3711-3721.
Shimanuki et al., "Role of Serum Vascular Endothelial Growth Factor in the Prediction of Angiogenesis and Prognosis for Non-small Cell Lung Cancer," Lung, 183: 29-42 (2005).
Simone, Joseph, V., "Part XiIV. Oncology," in: Cecil Textbook of Medicine, 20th Edition, Vol, 1, 2-3- 1997. W.B. Saunders Company, pp. 1004-1010.
Sinkula et al., "Rationale for Design of Biologically Reversible Drug Derivatives: Prodrugs," Journal of Pharmaceutical Sciences, vol. 64, No. 2, Feb. 1975, pp. 181-210.
Sin et al., "Phase I study of oral raf-1 kinase inhibitor BAY 43-9006 with gemcitabine in patients with advanced solid tumors," Abstract No. 828, Proc. Am. Soc. Clin. Oncol., 2003, vol. 22, p. 207.
Sin et al., "Phase I Trial of Sorafenib and Gemcitabine in Advanced Solid Tumors with an Expanded Cohort in Advanced Pancreatic Cancer," Clin. Cancer Res. 12(1):144-151 (2006).
Smith et al., "Discovery of Heterocyclic Ureas as a New Class of Raf Kinase Inhibitors: Identification of a Second Generation Lead by a Combinatorial Chemistry Approach," Bioorganic & Medicinal Chemistry Letters, 2001, vol. 11, pp. 2775-2778.
Smith et al., (Abstract) "Recent. Advances in the Research and Development of RAF Kinase Inhibitors," Current Topics in Medicinal Chemistry 6(11):1071-1089 (2006).
Smyth. R.M. et al., "Anchimeric Assistance in the Specific; Acid-catalysed Hydration of Benzonitriles" J. Chem. Soc. Perkin Trans. 2 1993 pp. 2171-2174.
Song, Huai-Dong et al., "Cross-host evolution of severe acute respiratory syndrome coronavirus in palm civet and human," Proc. Nati. Acad. Sci. USA 102(7):2430-2435 (2005).

(56) References Cited

OTHER PUBLICATIONS

Sorban et al "BAY-43-9006," Drugs of the Future, 2002, vol. 27, No. 12, pp. 1141-1147.

van Spronsen et al., "Novel treatment strategies in clear-cell metastatic renal cell carcinoma," Anti-Cancer Drugs, 2005, Vol, 16, pp. 709-717.

Stadler et al., "A Randomized Phase II Trial of the Antiangiogenic Agent S1J5416 in Hormone-Refractory Prostate Cancer," Clinical Cancer Research, 10: 3365-3370 (May 15, 2004).

Stahl et al., "Deregulated Akt3 Activity Promotes Development of Malignant Melanoma," Cancer Research, Vol, 64, No, 19; Oct. 2004; pp, 7002-7010.

Stavchansky et al., "Evaluation of the Bioavailability of a Solid Dispersion of Phenytoin in Polyethylene Glycol 6000 and a Commercial Phenytoin Sodium Capsule in the Dog," Journal of Pharmaceutical Sciences, Vol, 73 , No. 6, Jun. 1984, pp. 733-736.

Krontiris, "Chapter 71. Molecular and Cellular Biology of Cancer," and Capizzi, "Chapter 72, Principles of Treatment of Cancer," in: Internal Medicine, 4th Edition, Stein, Jay H., MD, Ed., Mosby, 1994, pp. 699-715.

Sternberg et al., "Conspiracy Theory: RAS and RAF Do Not Act Alone" Cell, vol. 95, pp. 447-450 (Nov. 13, 1998).

Stella et al., "Prodrugs and Site-Specific Drug Delivery," Journal of Medicinal Chemistry, vol. 2 No. 12, Dec. 1980, pp. 1275-1282.

Stella et al., "Prodrugs as therapeutics," Ep. Opin. Ther. Patents 14(31: 277-280 (2004).

Stella et al., "Prodrugs. Do They Have Advantages in Clinical Practice?" Drugs, vol. 29, 1985, pp. 455-473.

Stevenson et al., "Phase I Clinical/Pharmacokinetic and Pharmacodynamic Trial of the c-*raf* -1 Antisense Oligonucleotide ISIS 5132 (CGP 69846A)," The Journal of Clinical Oncology, vol. 17, No7: pp. 2227-2236 (Jul. 1999).

Stöckl et al,, "Integrity of c-Raf-1/MEK signal transduction cascade is essential for hepatitis B virus gene expression," Oncogene. Nature Publishing Group, 2003: vol. 22, pp. 2604-2610.

Stokoe et al., "Activation of c-Raf-1 by Ras and Src through different mechanisms: activation *in vivo* and *in vitro*," The Embo Journal, vol. 16 No. 9 pp. 2384-2396 (1997).

Storm et al., "*raf* Oncogenes in Carcinogenesis" Critical Reviews in Oncogenesis, vol. 2, Issue 1, pp. 1-8 (1990).

Strumberg, D. "Preclinical and Clinical Development of the Oral Muitikinase Inhibitor Sorafenib in Cancer Treatment," Drugs of Today, 41(12): 773-784 (2005).

Strumberg et al., "Phase I Clinical and Pharmacokinetic Shady of the Novel Raf Kinase and Vascular Endothelial Growth Factor Receptor inhibitor BAY 43-9006 in Patients With Advanced Refractory Solid Tumors," Journal of Clinical Oncology, Feb. 10, 2005, vol. 23, No. 5, pp. 965-972.

Strumberg et al., "Phase I Clinical, Pharmacokinetic and Pharmacodynamic Study of the Raf Kinase inhibitor BAY 43-9006 in Patients with Locally Advanced or Metastatic Cancer," Proc. Am. Soc. Chin. Oncol. 20: 2001 (abstr 330).

Strumberg et al., "Results of phase I pharmacokinetic and pharmacodynamic studies of the Raf kinase inhibitor BAY 43-9006 in patients with solid tumors." *International Journal of Clinical Pharmacology and Therapeutics*, 2002, vol. 40, No. 12, pp. 580-581.

Strumberg et al., "Sorafenib Neue Therapieoption in der Onkologie," Krankenhauspharmazie, 2007, vol. 28, pp. 93-97, pp. 1/5, 2/5, 3/5 and 4/5.

Suzuki et al., "The role of p38 mitogen activated protein kinase in IL-6 and IL-8 production from the TNF-α- or IL-β-stimulate rheumatoid synovial fibroblasts," FEBS Letters (2000), vol. 465, pp. 23-27.

Swarbrick et al., "Contents, pp. xvii-xviii in: Encyclopedia of Pharmceutical Technology." 2nd Edition, Marcel Dekker. Inc. 2002.

Swart, Guido W.M., "International Melanoma Research Congress—Foundation for Melanoma Research," IDRUGS: The Investigational Drugs Journal, Aug. 2003; vol. 6, No. 8, pp. 752-754.

Tabellini et al., "Novel 2'-substituted, 3'-deoxy-phosphatidyl-myo-inositiol analogues reduce drug resistance in human leukaemia cell lines with an activated phosphoinositide 3-kinase/Akt pathway," British Journal of Haematology, 126, 20C'4, pp. 574-582.

Takimoto et al.,"Safetly and anti tumor activity of sorafenib (Nexavar®) in combination with other anti- cancer agents: a review of clinical trials," Cancer Chemotherapy and Pharmacology (2008) 61:535-548.

Tamm e "Hypoxia-Induced Interleukin-6 and interleukin-8 Production Is Mediated by Platelet Activation Factor and Platelet-Derived Factor in Primary Human Lung Cells," Am. J. Respir. Cell Mol. Biol. vol. 19, pp. 653-661, (1998).

Tanaka et al., "Current status and perspective of antiangiogenic therapy for cancer: hepatocellular carcinoma," Int. J. Chin. Oncol. (2006) 11:82-89 (2006).

Tang et al., "Inhaled nitric oxide attenuates pulmonary hypertension and improves lung growth in infant rats after neonatal treatment with a VEGF receptor inhibitor." Am. J. Physiol. Lung Cell, Mol. Physiol. 287:L344-L351 (2004).

Tarzia et al., "Synthesis and anti-inflamatory properties of some pyrrolo(1H,3H) [3,4-d]ilpyrimidin-2-ones and pyrrolo=(1H,6H)[3,4-d]pyrimidin-2-ones," Chemical Abstracts, vol. 91, 1979. 91:74558p.

Teknos et al., "Elevated Serum Vascular Endothelial Growth Factor and Decreased Survival in Advanced Laryngeal Carcinoma," Head & Neck, 24: 1004-1011 (Nov. 2002).

Thaimattam et al, "3D-QSAR CoMFA, CoMSIA studies on substituted ureas as Raf-1 kinase inhibitors and its confirmation With structine-based studies," *Bioorganic & Medicinal Chemistry*, 2004, vol. 12, pp. 6415-6425.

Thelen et al., "VEGF-D promotes tumor growth and lymphatic spread in a mouse model of hepatocellular carcinoma" Int. J. Cancer 122, 2471-2481 (2008) © 2008 Wiley-Liss, Inc.

Thompson et al., "Recent progress in targeting the Raf/MEK/ERK pathway with inhibitors iia cancer drug discovery," Curr. Opin. Pharmacol., Aug. 2005, vol. 5, No. 4, pp. 350-356.

'Fong et M., "Pharmacodynamic Monitoring of BAY 43-9006 (Sorafenib) in Phase I Clinical Trials Involving Solid Tumor and AML/MDS Patients, Using Flow Cytometry to Monitor Activation of the ERK Pathway in Peripheral Blood Cells," Cytometry Part B (Clinical Cytometry) 70B: 107-114 (2006).

Trost et al., "Contents," Vols. 1-9, 36 pages in: Comprehensive Organic Synthesis: Selectivity, Strategy & Efficiency in Modern Organic Chemistry, Pergamon Press, Oxford, UK. 1991.

Gupta-Abramson et al., "Phase II Trial of Sorafenib in Advanced Thyroid Cancer" Journal of Clinical Oncology vol. 26, No. 29, pp. 4714-4719 (Oct. 10, 2008).

Veronese et al., "Mechanisms of Hypertension Associated with BAY 43-9006," Journal of Clinical Oncology, 2006, vol. 24, No. 9, pp. 1363-1369.

Vivanco et al., "The Phosphatidylinositol 3-Kinase-AKT Pathway in Human Cancer," Nature Reviews cancer, vol. 2, Jul. 2002. pp. 489-501.

Vlahos et al.. "A Specific Inhibitor of Phosphatidylinositol 3-Kinase, 2-(4-Morpholiny1)-8-phenyl-4H-1- benzopyran-4-one (LY294002)" *The Journal of Biological Chemistry*, vol. 269, No. 7. 1994, pp. 5241-5248.

Wakelee et al., "Targeting Angiogenesis with Vascular Endothelial Growth Factor Receptor SmallMolecular Inhibitors: Novel Agents with Potential in Lung Cancer," Clinical Lung Cancer, 7(Suppl 1): S31-S38 (Sept 2005).

Wald et al., "Involvement of the CXCL12/CXCR4 pathway in the advanced liver disease that is associated with hepatitis C virus or hepatitis B virus," Eur. J. Immunol., vol. 34, p. 1164-1174 (2004).

Wan et al., "Mechanism of Activation of the RAF-ERK Signaling Pathway y Oncogenic Mutations of B-RAF," *Cell*, Mar. 19, 2004, vol. 116, pp. 855-867.

Weekly Epidemiological Record, "Influenza," World Health Organization. Apr. 1999; vol. 14, pp. 111-112.

Wermuth, C. G., "Designing Prodrugs and Bioprecursors Ii: Bioprecursor Prodrugs," in: The Practice of Medicinal Chemistry, Academic Press Limited 1996,pp. 697-715.

White et al., "Heterocyclic Ureas: Inhibitors of Acyl-CoA:Cholesterol $O$ -Acyltransferase as Hypocholesterolemic Agents," J. Med. Chem. 1996, 39, pp. 4382-4395.

(56) References Cited

OTHER PUBLICATIONS

Wierzbowska et al., "Circulating VEGF and its soluble receptors sVEGER-1 and sVEGER 2 in patients with acute leukemia," EUR. Cytokine Netw., 14(3): 149-153 (Sep. 2003).

Wilhelm et al.,"A Novel Raf Kinase Inhibitor Blocks the Rahiviekierk Pathway in Tumor Cells," Poster, 92nd Annual Meeting of the American Association for Cancer Research, Mar. 24-28, 2001, New Orleans, LA USA, 1 page.

Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research, Oct. 1, 2004, vol. 64, pp, 7099-7109.

Wilh elm al., "BAY 43-9006: Preclinical Data," *Curr Pharm Des*, 2002, vol. 8, No. 25, pp. 2255- 2257.

Wilhelm et al., "Discovery and development of sorafenib: a muhlkinase inhibitor for treating cancer," Nature Reviews, Drug Discovery, 2006, vol. 5, pp. 835-844.

Wilhelm et al., "Preclinical overview of sorafenib, a multikinase inhibitor that targets both Raf and VEGF and PDGF receptor tyrosine kinase signaling," Mol. Cancer Ther., 2008, vol. 7, No. 10, pp. 3129-3140.

Wilkinson Geoffrey, "Contents," 7 pages in: Comprehensive Organometallic Chemistry. The Synthesis, Reactions, and Structures of Organometallic Compounds, Pergamon Press, Oxford, U.K. 1982: vol. 1-3.

Wilson et al., "The structural basis for the specificity of pyriditaylimidazole inhibitors of p38 MAP kinase," Chemistry & Biology, 1997, Vol, 4, No. 6, pp. 423-431.

Stollorz, "Die Krebsformel, die der Zufall fand," Frankfurter Allgemeine Sonntagszeitung, Jul. 2, 2006, NR 26,pp. 68-69.

Wissner et al., "Analogues of Platelet Activating Factor. 7. Bis-Aryl Amide and Bis-Aryl Urea Receptor Antagonists of PAF," *J. Med. Chem.*, 1992, vol. 35, pp. 4779-4789.

Wojnowski et al., "Endothelial apoptosis in Braf-deficient mice," Nature Genetics vol. 16, pp. 293-297 (Jul. 1997).

Onyx Pharmaceuticals, Inc,,"Novel RAF Kinase inhibitor Bay 43-9006 Shows Early Signs of Tolerability and Activity in Phase 1B Combination Trials Reported at ASCO," 1 page, (Press Release: Jun. 2, 2003).

Wright et al., "Bovine Immunodeficiency Virus Expression *in Vitro* is Reduced in the Presence of β-Chemokines, MIP-1α, MIP-1β and RANTES." Veterinary Research Communications. 2002: vol. 26, pp. 239-250.

Wright et al., "Clinical Trials Referral Resource. Current Clinical Trials of BAY 43-9006, Part 1," Oncology, Apr. 2005, vol. 19, No. 4: pp. 499-502.

Wu et al., "Plasma vascular endothelial growth factor is useful in assessing progression of breast cancer post surgery and during adjuvant treatment," International Journal of Oncology, 20: 509-516 (2002).

Xu et al., "Hypoxia-induced Elevation in Interleukin-8 Expression by Human Ovarian Carcinoma Cells," Cancer Research, 1999, Vol, 59, pp. 5822-5829.

He et al., "Oral Formulation of a Novel Antiviral Agent, PG301029, in a Mixture of Gelucire 44/14 and DMA (2:1, wt/wt)," AAPS PharmSciTech 2005; vol. 6 (1) Article 1, 5 pages, (http://www.aapsharmscitech.org).

Yamaguchi et al., "Expression of Vascular Endothelial Growth Factor in Human Hepatocellular Carcinoma," Hepatology, 28(1) pp. 68-77 (1998).

Yang et al. "Akt/Protein Kinase B Signaling inhibitor-2, a Selective Small Molecule inhibitor of a Akt Signaling with Antitumor Activity in Cancer Cells Overexpressing Akt," Cancer Research, 64, Jul. 1, 2004, pp. 4394-4399.

Yang et al., "Antiviral chemotherapy control of poxvipoxvirus infections through inhibition of cellular signal transduction," The Journal of Clinical Investigation, 2005: 115(2):pp, 379-387.

Yeh et al., "Characterization of severe acute respiratory syndrome coronavirus genomes in Taiwan: Molecular epidemiology and genome evolution," Proc. Natl. Acad. Sci, USA 2004-02-24, 101(8):2542-2547.

Yu et al.,"The role of Mc1-1 downregulation in the proapcptotic activity of the multikinase inhibitor' BAy 43-9006," Oncogene 24:6861-6869 (2005).

Zachos et al., "Herpes Simplex Virus Type 1 infection Stimulates p38/c-Jun N-terminal Mitogen-activated Protein Kinase Pathways and activates Transcription Factor Ap-1," Journal of Biological Chemistry, The American Society for Biochemistry and :Molecular Biology, Inc. 1999: vol. 274, pp. 5097-5103.

Zangari et al., "Phase II Study of SU5416, a Small Molecule Vascular Endothelial Growth Factor Tyrosine Kinase Receptor Inhibitor, in Patients with Refractory Multiple Myeloma," Clinical Cancer Research, 10: 88-95 (Jan 1, 2004).

Norden-Zfoni, Anat "Blood-Based Biomarkers of SU11248 Activity and Clinical Outcome in Patients with Metastatic Imatinib-Resistant Gastrointestinal Stromal Tumor," Clin. Cancer, Res. 2007; 13(9):2643-2650 May 1, 2007.

Zhao et al,, "Moderate mutation rate in the SARS coronavirus genome and its implications," BMC Evolutionary Biology, 2004, 4:21, 9 pages.

Zhu et al., "From the Cyclooxygenase-2 Inhibitor Celecoxib to a Novel Class of 3- Phosphoinositide-Dependent Protein Kinase -1 Inhibitors," Cancer Research 64, Jun. 15, 2004, pp. 4309-4318.

Carter et al., "Anti-tumor Efficacy of the Orally Active RAF Kinase Inhibitor Bay 43-90006 in Human Tumor Xenograft Model," #4954, Proceedings of the American Association for Cancer Res,, 2001, vol. 42, p. 923.

Riedl et al.,#4956"Potent *Raf* Kinase Inhibitors from the Diphenylurea Class: Structure Activity Relationships," Proceedings of the American Association for Cancer Research, vol. 42, Mar. 2001 (2001-2003), p. 923, 92nd Annual Meeting of the American Association for Cancer Research; New Orleans, LA, USA; Mar. 24-28, 2001.

Strumberg et al., abstract No. #2921 "Phase 1 and Pharmacokinetic Study of the Raf Kinase Inhibitor Bay 43-9006 in Patients with Locally Advanced or Metastic Cancer," Proceedings of the American Association for Cancer Research, vol. 42. Mar. 2001 (2001-2003), p. 543, 92nd Annual Meeting of the American Association for Cancer Research;New Orleans, LA, USA; Mar. 24-28, 2001.

Abstract of DE 3305866 A1, Aug. 23, 1984, BASF AG et al.

Abstract of EP 16371 (1980), 1 page, Hoffmann-La Roche AG.

Abstract of EP 16371, Oct. 1, 1980, 1 page.

Abstract of EP 116932, Aug. 29, 1984, 2 pages.

Abstract of EP 116932, (1984), 2 pages. BASF AG.

Abstract of EP 0202538, (1986), 3 pages.

Abstract of EP 0202538 A1, Growth Promoting Agents Nov. 26, 1986, 4 pages, Bayer AG.

Abstract of EP 0676395A2, (1995), 3 pages, Hoechst AG.

Abstract of EP 676395, (U.S. equivalent 5,698,581), Dec. 18. 1997 1 page.

Patent Abstracts of Japan 02-022650, Jan. 25, 1990, 2 pages, Konica Corp.

esp@cenet Abstracts of Japan 02-022650, Jan. 25, 1990, 1 page.

Patent Abstracts of Japan 02-023337, Jan. 25, 1990, 2 pages. Konica Corp.

Patent Abstracts of Japan 63-214752, Sep. 7, 1988, 2 pages, family member of JP 6-07512 B4, Fuji Photo Film Co. Ltd.

Abstract of IP 55162772 A2, Preparation of Substituted Acetic Acid Derivatives. Shiongi & Co., Ltd. Dec. 1980, 1 page.

Esp@cenet Abstract of WO 9822103, May 28, 1998, Philip Hedge et al.

Abstract of WO 9822098 A2, QLT Phototherapeutics Inc. et al., May 28, 1998, 1 page.

Abstract of WO 9822103 A1, Zeneca Limited, published May 28, 1998, 1 page.

Abstract of WO 9852559 A1, Bayer Corp. et at, published Nov. 26, 1998, 1 page.

Abstract of WO 9852562 A1, Verkaik. MSE, et al., published Nov. 26, 1998, 1 page.

(56) References Cited

OTHER PUBLICATIONS

Abstract of WO 9900357 A1, Vertex Pharm. Inc., published Jan. 7, 1999. 1 page.
Abstract of WO 9900364 A1, Pharmacia Upjohn S.P.A. et al., published Jan. 7, 1999, 1 page.
Abstract of WO 9932098 A2, Janssen Pharm NV, published Jul. 1, 1999, 1 page.
Abstract of WO 9932106 A1, Bayer Corp., published Jul. 1, 1999, 1 page.
Abstract of WO 9932148 A1 Beth Israel Deaconess Medical Center et al., pub. Jul. 1, 1999. 1 page.
Abstract of WO 9932436 A1, Bayer Corp., published Jul. 1, 1999, 1 page.
Abstract of WO 9932455 A1, Bayer Corp., published Jul. 1, 1999, 1 page.
Abstract of WO 9932457 A1, Hoechst Marion Roussel Deutschland GmbH et al., published Jul. 1, 1999, 1 Page.
Caplus 72:79046, Abstract of CH 439557, "Tuberculostatic and cancerostatic polybasic ureas," Dr. A. Wander, Oct. 15, 1969, 6 pages.
Caplus 84:180049, Abstract JP 56029871, "Substituted acetic acid derivatives," Hamada, Yoshinori et al., Jul. 10, 1981, 1 page.
Caplus 84:43857, Abstract JP 58021626, "Alkanoic acid derivatives containing a pyridine ring," Maeda, Ryozo et al., May 2, 1983, 1 page.
Caplus 86:72448, Abstract JP 57053785, "Pyridine derivatives," Maeda, Ryozo et al., Nov. 15, 1982, 1 page.
Caplus 87:62295, "The metabolism and toxicity of halogenated carbanilides. Biliary metabolites of 3,4,4'-trichlorocarbanilide and 3-triftuoromethyl-4,4'-dichlorocarbanilide in the rat," Chemical Life Science, pp. 157-66, 1977, 1 page.
Caplus 98:78152, Abstract of JP 57185219, "Antitumor benzophenone derivatives," Noveamber 15, 1982, 1. page, Chugai Pharmaceutical Co., Ltd.
Caplus 113:106314, Abstract of JP 2022650, "Silver halide color photographic material containing a cyan coupler of 2-ureido-phenol type to improve dye developability and remove lecuo cyan dye," Noboru Mizukura et al. Jan. 25, 1990, 1 page.
Caplus 113:142130, Abstract of JP 2023337, "Silver halide photographic material containing phenolic cyan coupler a colorless cyan coupler," Toshihiko Yagi et al., Jan. 25, 1990, 1 page.
Caplus 125:245169, "Production of murine monoclonal antibodies against sulcofuron and flucofuron by in vitro immunization," G. A. Bonwick et al., J. immunol. Methods, 196(2), pp. 163-173, 1996, 1 page.
Caplus 126:166148, "inthibitors of coenzyme A-independent transacylase induce apoptosis in human HL-60 cells," James D. Winkler et al., J. Pharmacol. Exp. Ther. 279(2), pp. 956-966, 1996, 2 pages.
Dearden et al.,"Quantitative structure-biodegradability studies: an investigation of the MITI aromatic compound data-base," in: Biodegradability Prediction, Edited by Willie J.G.M. Peijnenburg et al., NATO ASI Series, 2. Environment—vol. 23, pp. 93-104, 1996; Chem Abst No. 127:273945.
Caplus 127:293717, "Optical properties of segmented oligourethane with azomethine terminal fragments," National Academy of Science of Ukraine, M. V. Kurik et al., pp. 2038-2041, 1996, 2 pages.
Caplus 127:34137f, "Preparation of quinoline and quinazoline derivatives inhibiting platelet-derived growth factor receptor autophosphorylation," Kazuo Kubo et al., May 15, 1997, WO 97/17329.
Caplus 131:58658k, "Inhibition of raf kinase using symmetrical and unsymmetrical substituted diphenyi ureas," Miller, Scott, et al Jul. 1, 1999, WO 99 32,436.
Caplus 131:73649b, "Preparation of pyrazolyi aryl ureas and related compounds as p38 kinase inhibitors," Jacques Dumas et al., Jul. 1, 1999, WO 99/32110.
Caplus 131:87909y, "Inhibition of p38 kinase activity using -in substituted heterocyclic ureas," Jacques Dumas et al., Jul. 1, 1999, WO 99/32111.

Caplus 146:265643 Abstract of Strumberg et al., "Sorafenib—A novel opportunity in oncology," Arzneimitteltherapie 25(1):2-6 (2007) abstract, 1 page.
Kujundzic et al., "Synthesis of 8-methyl-1,2,3,4-tetrahydropyrido[3,4-d] pyrimidine-24-diones," Croat. Chem. Acta (1991) 64(4).599-606, Chemical Abstracts vol. 116, No. 21, May 25, 1992, (pp. 741-742) No. 116:214456.
Badran et al., "Novel piperazinyi-substituted pyrimidines as antihypertensive and vasodilators," Revue Roumaine de Chimie (1992). 37(2).238-288, Chemical Abstracts vol. 117.251318.
"Beilstein number" Collection, 28 pp. (1997).
"Beilstein number" Collection. 4 pp. (1997).
Derwent Work Patents Index Search, pp. 20-26. (1997).
Dumas, J. "CAS Substructure," May 6, 1997,pp, 1-29.
Scott, Bill, "Substructure (Patent Families)," Aug. 11, 1997. pp. 1-19.
Scott Bil "Substructure #2," Nov. 25, 1997, pp. 1-3.
Scott, Bill, "Substructure Search," Dec. 2, 1997, pp. 1-49.
Substructure Search. pp. 1-29. (1997).
Wild, Hanno, "Substructure #1," search, pp. 1-150, 1996.
A "Notice of References Cited" from the USPTO for U.S. Appl. No. 08/995,749, filed Dec. 22, 1997, Inhibition of P38 Kinase Iising Symmetrical and Unsymmetrical Diphenyl Ureas, 2 pages.
A "Notice of References Cited" from the USPTO for U.S. Appl. No. 09/083,399, filed May 22, 1998, Patent 6187799 issued Feb. 13, 2001, Inhibition of Raf Kinase Activity Using Aryl Ureas, 1 page.
A "Notice of References Cited" from the USPTO for U.S. Appl. No. 09/425,228, filed Oct. 22, 1999, Omega-Carboxyaryl Substituted Diphenyl Ureas As Raf Kinase Inhibitors, 3 pages.
A "Notice of References Cited" from the USPTO for U.S. Appl. No. 09/425,229, filed Oct. 22, 1999, Omega-Carboxy Aryl Substituted Diphenyl Ureas As p38 Kinase Inhibitors, 1 page.
A "Notice of References Cited" from the USPTO for U.S. Appl. No. 09/458,015, filed Dec. 10, 1999, Inhibition of p38 Kinase Using Symmetrical and Unsymmetrical Diphenyl Ureas, 1 page.
A "Notice of References Cited" from the USPTO for U.S. Appl. No. 09/472,232, filed Dec. 27, 1999, Patent 7329670 issued Feb. 12, 2008, Inhibition of Raf Kinase Using Aryl and Heteroaryl Substituted Heterocyclic Ureas, 1 page.
A "Notice of References Cited" from the USPTO for U.S. Appl. No. 09/773,604, filed Feb. 21, 1999, Publication No. US 2001-0034447-A1, Publication Date Oct. 25, 2001 Omega-carboxyaryl Substituted Diphenyl Ureas as Raf Kinase inhibitors, 1 page.
A "Notice of References Cited" from the USPTO for U.S. Appl. No. 09/773,659, filed Feb. 2, 2001, Publication No. US 2001-0011135 A1, Publication Date: Aug. 2, 2001, Omega-carboxyaryl Substituted Diphenyl Ureas As Raf Kinase Inhibitors, 1 page.
A "Notice of References Cited" from the USPTO for U.S. Appl. No. 09/773,672, filed Feb. 2, 2001, Publication No. US 2001-0016659 A1, Publication Date: Aug. 23, 2001, Omega-carboxyatyl substituted Diphenyl Ureas As Raf Kinase Inhibitors, 1 page.
A "Notice of References Cited" from the USPTO for U.S. Appl. No. 09/773,675, filed Feb. 2, 2001, Publication No.: US 2001-0011136-A1 , Publication Date: Aug. 2, 2001, Omega-Carboxyaryl Substituted Diphenyl Ureas as Raf Kinase Inhibitors, 1 page.
A "Notice of References Cited" from the USPTO for U.S. Appl. No. 09/776,935 filed Dec. 22, 1998, Inhibition of p38 Kinase Using Aryl and Heteroaryl Substituted Heterocyclic Ureas, 1 page.
A "Notice of References Cited" from the USPTO for U.S. Appl. No. 09/776,936, filed Dec. 28, 1998, inhibition of Raf Kinase Using Symmetrical and Unsymmetrical Substituted Diphenyl Ureas, 1 page.
A "Notice of References Cited" from the USPTO for U.S. Appl. No. 09/777,920, filed Feb. 7, 2001, inhibition of RAF kinase using quinolyl, isoquinolyi or pyridyl ureas, 1 page.
A "Notice of References Cited" from the USPTO for U.S. Appl. No. 09/948,915, filed Sep. 10, 2001, Omega-Carboxyaryl Substituted Diphenyl Ureas As Raf Kinase Inhibitors, 1 page.
A "Notice of References Cited" from the USPTO for U.S. Appl. No. 10/042,226, filed of Jan. 11, 2002, Omega-Carboxyaryl Substituted Diphenyl Ureas As Raf Kinase Inhibitors, 1 page.
Co-pending U.S. Appl. No. 09/458,014, filed Dec. 10, 1999, Dumas et al.

(56) References Cited

OTHER PUBLICATIONS

Abandoned U.S. Appl. No. 09/776,935, filed Dec. 22, 1998, Dumas et al.
Co-pending U.S. Appl. No. 09/776,936, filed Dec. 22, 1998, Miller et al.
Issued U.S. Appl. No. 09/889,227, filed Jul. 12, 2000, Riedl et al., issued as 7351834, Apr. 1, 2008.
Co-pending application U.S. Appl. No. 09/993,647, filed Nov. 27, 2001, Riedl et al., published as 2003-0181442, Sep. 25, 2003.
Issued U.S. Appl. No. 10/060,396, filed Feb. 1, 2002, Miller et al., patent 7517880, issued Apr. 14, 2009, also published as 2004-0102636, May 27, 2004..
Issued U.S. Appl. No. 10/071,248, filed Feb. 11, 2002, Riedl et al., patent 7528255, issued May 5, 2009, also published as 2003-139605, Jul. 24, 2003.
Abandoned U.S. Appl. No. 10/086,417, filed Mar. 4, 2002, Riedl et al., published as 2003-0105091, Jun. 5, 2003.
Abandoned U.S. Appl. No. 10/125,369, filed Apr. 19, 2002, Dumas et al., published as 2003-0207914, Nov. 6, 2003.
Abandoned U.S. Appl. No. 10/308,187, filed Dec. 3, 2002, Carter et al., published as 2003-0232765, Dec. 18, 2003.
Abandoned U.S. Appl. No. 10/361,844, filed Feb. 11, 2003, Dumas et al., published as 2004-0023961, Feb. 5, 2004.
Abandoned U.S. Appl. No. 10/361,850, filed Feb. 11, 2003, Dumas et al., published as US 2003-0216396, Nov. 20, 2003.
Co-pending U.S. Appl. No. 10/361,859, filed Feb. 11, 2003, Dumas et al., published as 2003-0216446, Nov. 20, 2003.
Co-Pending U.S. Appl. No. 10/895,985, filed Jul. 22, 2004, Boyer et al., published as US 2005-0038080, Feb. 17, 2005.
Co-Pending U.S. Appl. No. 11/932,548, filed Oct. 1 2007, Dumas et al.,.
Co-Pending U.S. Appl. No. 121084,662, filed May 7, 2008, Sandier et al., published as 2010- 0035888, Feb. 11, 2010.
Co-Pending U.S. Appl. No. 12/086,454, filed Jun. 12, 2008, Weber et al.
Co-Pending U.S. Appl. No. 12/093,515, filed Nov. 13, 2008, Wilhelm et al.
Co-Pending U.S. Appl. No. 12/095,611, filed May 30, 2008, Smith et al.
Co-Pending U.S. Appl. No. 12/158,524, filed Jun. 20, 2008 Smith et al.
Co-Pending U.S. Appl. No. 12/294,979, filed Sep. 29, 2008, Wilhelm et al.
Co-Pending U.S Appl. No. 12/421,690, filed Apr. 10, 2009, Dumas et al.
Co-Pending U.S. Appl. No. 12/444,974, filed Apr. 9, 2009, Grunenberg et al.
Co-Pending U.S. Appl. No. 12/514,129, filed May 8, 2009, Grunenberg et al.
Co-Pending U.S. Appl. No. 12/514,715, filed May 13, 2009, Stiehl et al.
Co-Pending U.S. Appl. No. 12/520,618, filed Jun. 22, 2009, Smith et al.
Co-Pending U.S. Appl. No. 12/520,609, filed Jun. 22, 2009, Smith et al.
Co-pending U.S.Appl. No. 12/523,652, filed Jul. 17, 2009, Wilhelm et al.
Co-pending U.S. Appl. No. 12/523,697, filed Jul. 17, 2009, Wilhelm et al.
Co-Pending U.S. Appl. No. 12/628,735, filed Dec. 1, 2009, Dumas et al.
Co-Pending U.S. Appl. No. 12/692,845, filed Jan. 25, 2010, Dumas et al.
Co-Pending Application PCT/US09/61506, filed Oct. 21, 2009, Carol Pena.
International search report for :international Application No. PCT/US598/10375 dated Sep. 3, 1998, Inhibition of p38 Kinase Activity by Aryl Ureas, publication No. 98/52558, publication date Nov. 26, 1998, 1 page.
International search -po t for International Application No. PCT/U598110376 dated Jul. 30, 1998, Raf Kinase inhibitors, publication No. WO 98/52559, publication date Nov. 26, 1998, 1 page.
International search report for International Application No. PCT/US98/26078 dated Apr. 2, 1999, Inhibition of Raf Kinase Using Substituted Heterocyclic Ureas, publication No. WO 99/32106, publication date Jul. 1, 1999, 2 pages.
international search report for International Application No. PCT/US98/26079 dated Apr. 12, 1999, Inhibition of p38 Kinase Activity Using Aryl and Heteroaryl Substituted Heterocyclic Ureas, publication No. WO 99/32110, publication date Jul. 1, 1999, 1 page.
International search report for :international Application No. PCT/11598/26080 dated Apr. 12,1999, Inhibition of p38 Kinase Using Substituted Heterocyclic Ureas, publication No. WO 99/32111, publication date Jul. 1, 1999, 1 page.
International search report for International Application No. PCT/US98/26081 dated Apr. 2, 1999, Inhibition of Raf Kinase Using Symmetrical and Unsymmetrical Substituted Diphenyl Ureas, publication No. WO 99/32436, publication date Jul. 1, 1999, 1 page.
International search report for International Application No. PCT/US98/26082 dated 5/12/99, inhibition of Raf Kinase Using Aryl and Heteroaryl Substituted Heterocyclic Ureas, publication No. WO 99/32455, publication date Jul. 1, 1999, 1 page.
International search report for International Application No. PCT/US98/27265, dated Mar. 2, 1999, Inhibition of p38 kinase using symmetrical and unsymmetrical diphenyl ureas, publication No. WO 99/32463, publication date Jul. 1, 1999, 1 page.
International search report for international Application No. PCT/US00/00648 dated Jun. 29, 2000, Omega-Carboxyaryl Substituted Diphenyl Ureas as RAF Kinase Inhibitors, publication No. WO 00/42012 A1, publication date Jul. 1, 2000, 2 pages.
International search report for International Application No. PCT/US00/00768 dated May 16, 2000, Omega-Carboxy Aryl Substituted Diphenyl Ureas As p38 Kinase inhibitors, publication No. WO 00/41698 A1, publication date Jul. 20, 2000, 1 page.
International search report for International Application No. PCT/U502/12064 dated Sep. 20, 2002, Heteroaryl Ureas Containing Nitrogen Hetero-Atoms As p38 Kinase Inhibitors, publication No. 02/085859, publication date Oct. 31, 2002, 2 pages.
International search report for International Application No. PCT/S02/12006 dated Sep. 27, 2002, Inhibition of Raf Kinase Quinolyl, Isoquinobil or Pyridyl Ureas, publication No. 02/085857, publication date Oct. 31, 2002, 2 pages.
Supplemental search report from the EPO for European application EP 98963809.3 dated Mar. 30, 2001, inhibition of Raf Kinase Using Symmetrical and Unsymmetrical Substituted Diphenyl Ureas, publication No. 1049664, publication date Jul. 1, 1999, granted Mar. 16, 2005, 4 pages.
Supplemental search report from the EPO for European application EP 98963810.1 dated Dec. 21, 2000, Inhibition of Raf Kinase Using Aryl and Heteroaryl Substituted Heterocyclic Ureas, publication No. 1056725, publication date Jul. 1, 1999, granted Jun. 7, 2006, 4 pages.
Supplemental search report from the EPO for European application EP 98965981.8 dated Dec. 21, 2000, Inhibition of Raf Kinase Using Substituted Heterocyclic Ureas. publication No. 1047418, publication date Jul. 1, 1999, granted Jul. 27, 2005, 8 pages.
Supplemental search report from the EPO for European application EP 00903239.2 dated Aug. 7, 2002, Omega-Carboxyaryl Substituted Diphenyl Ureas As Raf Kinase Inhibitors, publication No. EP 1140840, published Jul. 20, 2000, granted Mar. 22, 2006, 6 pages.
Supplemental search report from the EPO for European application EP 00905597.1 dated Feb. 7, 2008, Omega-Carboxyaryl Substituted Diphenyl Ureas As p38 Kinase Inhibitors, publication No. EP 1158985, Jul. 20, 2000, 9 pages.
Beigore et al.. "Measurement of free and complexed soluble vascular endothelial growth factor receptor, Flt-1, in fluid samples: development and application of two new immunoassays," Clinical Science, 100: 567-575 (2001).
Beigore et al., "Plasma Levels of Vascular Endothelial Growth Factor (VEGF) and Its Receptor, Flt-1, in Haematological Cancers: A Comparison With Breast Cancer," American Journal of Hematology, 66:59-61 (2001).

(56) References Cited

OTHER PUBLICATIONS

Coskun et al., "Significance of serum vascular endothelial growth factor, insulin-like growth factor-I levels and nitric oxide activity in breast cancer patients," The Breast, 12, 104-110 (2003).
Kaya et al., "The prognostic significance of vascular endothelial growth factor levels in sera of non-small cell lung cancer patients," Respiratory Medicine, 98:632-636 (2004).
Kumar et al., "Soluble FLT-1 is Detectable in the Sera of Colorectal and Breast Cancer Patients," Anticancer Research, 22:1877-1880 (2002).
Pasieka et al., "Evaluation of the Levels of bFGF, VEGF, sICAM-1, and sVCAM-1 in Serum of Patients with Thyroid Cancer," Recent Results in Cancer Research, 162:189-194 (2003).
Pegram et al., "Combined Biological Therapy of Breast Cancer Using Monoclonal Antibodies Directed Against HER2/neu Protein and Vascular Endothelial Growth Factor," Seminars in Oncology, 29(Suppl. 11):29-37 (2002).
Poon et al., "Prognostic significance of serum vascular endothelial growth factor an endostatin in patients with hepatocellular carcinoma," British Journal of Surgery, 91:1354-1360 (2004).
Ria et al., "Serum levels of angiogenic cytokines decrease after antineoplastic radiotherapy," Cancer Letters, 216:103-107 (2004).
Secord et al., "The relationship between serum vascular endothelial growth factor, persistent disease, and survival at second-look laparotomy in ovarian cancer," Gynecologic Oncology, 94:74-79 (2004).
English abstract of JP 10-306078, Nov. 17, 1998, Patent Abstracts of Japan, 2 pages.
English abstract of JP 08-301841, Nov. 19, 1996, Patent Abstracts of Japan, 2 pages.
English abstract of JP 03-198049, Aug. 29, 1991, Patent Abstracts of Japan, 1 page.
English abstract of JP 03:144634, Jun. 20, 1991, Patent Abstracts of Japan, 1 page.
English abstract of JP 03-053247, Mar. 7, 1991, Patent Abstracts of Japan, 1 page.
English abstract of JP 02-150840, Jun. 6, 1990, Patent Abstracts of Japan, 1 page.
English abstract of JP 02-108048, Apr. 19, 1990, Patent Abstracts of Japan, 1 page.
English abstract of JP 02-105146, Apr. 4, 1990, Patent Abstracts of Japan, 1 page.
English abstract of JP 02-035450, Feb. 6, 1990, Patent Abstracts of Japan, 1 page.
English abstract of JP 01-200254 Aug. 11, 1989, Patent Abstracts of Japan, 1 page.
English abstract of JP 01-259360, Oct. 17, 1989, Patent Abstracts of Japan, 2 pages.
English abstract of JP 01-102461, Apr. 20, 1989, Patent Abstracts of Japan, 1 page.
English abstract of JP 06-120039, Apr. 28, 1994, Patent Abstracts of Japan, 1 page.
English abstract of JP 05-180862, Jul. 23, 1993, Patent Abstracts of Japan, 1 page.
English abstract of JP 05-163170, Jun. 29, 1993, Patent Abstracts of Japan, 1 page.
English abstract of JP 05-077375, Mar. 30, 1993, Patent Abstracts of Japan, 1 page.
English abstract of JP 05-076072, Mar. 26, 1993, Patent Abstracts of Japan, 2 pages.
English abstract of JP 53-086033, Jul. 29, 1978, Patent Abstracts of Japan, 1 page.
English abstract of JP 54-032468, Sep. 3, 1979, Patent Abstracts of Japan, 1 page.
English abstract of JP 55-098152, Jul. 25, 1980, Patent Abstracts of Japan, 1 page.
English abstract of JP 64-009455 Jan. 12, 1989, Patent Abstracts of Japan, 1 page.
English abstract of JP 02-023337, Mar. 9, 1979, Patent Abstracts of Japan, 2 pages.
English abstract of EPA 0379915/EP-A1, Aug. 1, 1990, 2 pages.
English abstract of DD 253997 A, Feb. 10, 1988, 1 page.
English abstract of DE511468, European Patent Office, 2 pages; Oct. 16, 1930.
Co-Pending U.S. App. No. 12/619,913, filed Nov. 17, 2009, Ranges et al.
Abstract of EP 4931 A (Equivalent 4,240,820), Bayer AG, 1 page (Dec. 23, 1980).
Abstract of EP 0405233A1, Tetsuo Sekiya et al., 1 page (Jan. 2, 1991).
esp@cenet Abstract of Japan 02-023337, 1 page (Jan. 25, 1990).
English abstract of JP 50-149668 A and JP 56-29871 B, Derwent World Patents Index, Dialog File No. 351, Ace. No. 1488399, 3 pages, (Nov. 29, 1975).
Toi et al', "Inhibition of vascular endothelial growth-factor induced cell-growth by an angiogenesis inhibitor agm-1470 in capillary endothelial-cells," Oncol. Rep. Mar. 1994 ; 1(2) :423-426.
Kim et al. "Sorafenib inhibits the angiogenesis and growth of orthotopic anaplastic thyroid carcinoma xenografts in nude mice" *Molecular Cancer Therapeutics* 2007;6(6), Jun. 2007, pp. 1784-92.
Smith et al. "Vascular Endothelial Growth Factor Receptors VEGFR-2 and VEGFR-3 Are Localized Primarily to the Vasculature in Human Primary Solid Cancers." Clin Cancer Res; 16(14) Jul. 15, 2010, pp. 3548-3561.
National Cancer Institute Bulletin: "Angiogenesis inhibitors." Published: Oct. 7, 2011.
Escudier et al. "Sorafenib in Advanced Clear-Cell Renal-Cell Carcinoma." New England Journal of Medicine, 2007 Jul 12;357(2):203.
Clinicaltrials.Gov # NCT00073307 "Study of BAY43-9006 in patients with unresectable and/or metastatic renal cancer." Nov. 8, 2012.
Bayer Corporation et al., "Trial of BAY 43-9006 in Patients with Relapsed or Refractory Advanced Non-Small Cell Lung Carcinoma", NCT0010413, clinicaltrials.gov, 3 pages, (2005).
Iwadate et al., MEDLINE/NLM, NLM8336809 "Intra-arterial ACNU, CDDP chemotherapy for brain metastases from lung cancer: comparison of cases with and without intra-arterial mannitol infusion," 1 page, abstract, (1993).
Abstract of EP 4931 A (Equivalent 4,240,820), Bayer AG, 1 page, (1980).
Abstract of EP 0405233A1, Mitsubishi Kasei Corp., 2 pages, (1991).
Abstract of EP 0405233A1, Tetsuo Sekiya et al., 1 page, (1991).
esp@cenet Abstract of Japan 02-023337, 1 page, (1990).
English abstract of JP 50-149668 A and JP 56-29871 B, Derwent World Patents Index, Dialog File No. 351, Acc. No. 1488399, 3 pages, (1975).

ARYL UREAS WITH ANGIOGENESIS INHIBITING ACTIVITY

This application is a continuation of U.S. application Ser. No. 12/888,887, filed Sep. 23, 2010, now U.S. Pat. No. 8,242,147, which is a continuation of application Ser. No. 10/361,858, filed Feb. 11, 2003, now U.S. Pat. No. 7,838,541, which claims the benefit of U.S. provisional application No. 60/354,950, filed Feb. 11, 2002 and are incorporated by reference herein.

FIELD OF THE INVENTION

This invention relates to methods of treating diseases mediated by the VEGF induced signal transduction pathway characterized by abnormal angiogenesis or hyperpermeability processes.

BACKGROUND OF THE INVENTION

Vasculogenesis involves the de nova formation of blood vessels from endothelial cell precursors or angioblasts. The first vascular structures in the embryo are formed by vasculogenesis. Angiogenesis involves the development of capillaries from existing blood vessels, and is the principle mechanism by which organs, such as the brain and the kidney are vascularized. While vasculogenesis is restricted to embryonic development, angiogenesis can occur in the adult, for example during pregnancy, the female cycle, or wound healing.

One major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are highly specific for vascular endothelial cells (for reviews, see: Farrara et al. *Endocr. Rev.* 1992, 13, 18; Neufield et al. *FASEB J.* 1999, 13, 9).

VEGF expression is induced by hypoxia (Shweiki et al. *Nature* 1992, 359, 843), as well as by a variety of cytokines and growth factors, such as interleukin-1, interleukin-6, epidermal growth factor and transforming growth factor-α and -β.

To date VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. Regulation of the VEGF-mediated signal transduction cascade will therefore provide a useful mode for control of abnormal angiogenesis and/or hyperpermeability processes.

Angiogenesis is regarded as an absolute prerequisite for growth of tumors beyond about 1-2 mm. Oxygen and nutrients may be supplied to cells in tumor smaller than this limit through diffusion. However, every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci.*, 1995, 92, 768). In addition, VEGF production in tumor regions where there is no angiogenesis may proceed through the ras signal transduction pathway (Grugel et al. *J. Biol. Chem.*, 1995, 270, 25915; Rak et al. *Cancer Res.* 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol.* 1995, 26, 86), gastrointestinal tract (Brown et al. *Cancer Res.* 1993, 53, 4727; Suzuki et al. *Cancer Res.* 1996, 56, 3004), kidney and bladder (Brown et al. *Am. J. Pathol.* 1993, 1431, 1255), ovary (Olson et al. *Cancer Res.* 1994, 54, 1255), and cervical (Guidi et al. *J. Nat'l Cancer Inst.* 1995, 87, 12137) carcinomas, as well as angiosacroma (Hashimoto et al. *Lab. Invest.* 1995, 73, 859) and several intracranial tumors (Plate et al. *Nature* 1992, 359, 845; Phillips et al. *Int. J Oncol.* 1993, 2, 913; Berkman et al, *J. Clin. Invest.*, 1993, 91, 153). Neutralizing monoclonal antibodies to KDR have been shown to be efficacious in blocking tumor angiogenesis (Kim et al. *Nature* 1993, 362, 841; Rockwell et al, *Mol. Cell. Differ.* 1995, 3, 315).

Over expression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, retinopathy of prematurity (Aiello et al, *New Engl. J. Med.* 1994, 331, 1480; Peer et al. *Lab. Invest.* 1995, 72, 638), and age-related macular degeneration (AMD; see, Lopez et al. *Invest. Opththalmol. Vis. Sci.* 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other fauns of arthritis of with degenerative joint disease (Koch et al. *J. Immunol.* 1994; 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

Because inhibition of KDR leads to inhibition of VEGF-mediated angiogenesis and permeabilization, KDR inhibitors will be useful in treatment of diseases characterized by abnormal angiogenesis and/or hyperpermeability processes, including the above listed diseases

SUMMARY OF THE INVENTION

The present invention provides a method for treating diseases in humans or other mammals which are mediated by the VEGF induced signal transduction pathway, including those characterized by abnormal angiogenesis or hyperpermiability processes. These methods comprise administering a compound of formula I below or a salt, prodrug or stereoisomer thereof to a human or other mammal with a disease characterized by abnormal angiogenesis or hyperpermiability processes.

The compounds of formula I, which include all stereoisomeric forms (both isolated and in mixtures) salts thereof and prodrugs thereof are collectively referred to herein as the "compounds of the invention."

Formula I is as follows:

A-NH—C(O)—NH—B wherein A is selected from the group consisting of (i) phenyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

(ii) naphthyl, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

(iii) 5 and 6 membered monocyclic heteroaryl groups, having 1-3 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro; and (iv) 8 to 10 membered bicyclic heteroaryl group in which the first ring is bonded to the NH of FIGURE I and contains 1-3 heteroatoms independently selected from the group consisting of O, N, and S, and the second ring is fused to the first ring using 3 to 4 carbon atoms. The bicyclic heteroaryl group is optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro.

B is selected from the group consisting of (i) phenyl, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro;

(ii) naphthyl, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro;

(iii) 5 and 6 membered monocyclic heteroaryl groups, having 1-3 heteroatoms independently selected from the group consisting of O, N and S, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro; and (iv) 8 to 10 membered bicyclic heteroaryl groups having 1-6 heteroatoms independently selected from the group consisting of O, N and S, optionally substituted with 1-3 substituents independently selected from the group consisting of -L-M, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro.

L is selected from the group consisting of:
(a) —$(CH_2)_m$—O—$(CH_2)_l$—,
(b) —$(CH_2)_m$—$(CH_2)_l$—,
(c) —$(CH_2)_m$C(O)—$(CH_2)_l$—,
(d) —$(CH_2)_m$—$NR^3$—$(CH_2)_l$—,
(e) —$(CH_2)_m$—$NR^3$C(O)—$(CH_2)_l$—,
(f) —$(CH_2)_m$—S—$(CH_2)_l$—,
(g) —$(CH_2)_m$—C(O)$NR^3$—$(CH_2)_l$—,
(h) —$(CH_2)_m$—$CF_2$—$(CH_2)_l$—,
(i) —$(CH_2)_m$—$CCl_2$—$(CH_2)_l$—,
(j) —$(CH_2)_m$—CHF—$(CH_2)_l$—,
(k) —$(CH_2)_m$—CH(OH)—$(CH_2)_l$—;
(l) —$(CH_2)_m$—C≡C—$(CH_2)_l$—;
(m) —$(CH_2)_m$—C=C—$(CH_2)_l$—; and
(n) a single bond, where m and l are 0;
(o) —$(CH_2)_m$—$CR^4R^5$—$(CH_2)_l$—;

The variables m and l are integers independently selected from 0-4.

M is selected from the group consisting of:

(i) phenyl, optionally substituted with 1-3 substituents independently selected from the group consisting of $R^1$, $OR^1$, $NR^1R^2$, $S(O)_sR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro;

(ii) naphthyl, optionally substituted with 1-3 substituents independently selected from the group consisting of $R^1$, $OR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro;

(iii) 5 and 6 membered monocyclic heteroaryl groups, having 1-3 heteroatoms independently selected from the group consisting of O, N and S, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro and also oxides (e.g. =O, —O⁻ or —OH); and (iv) 5 to 10 membered bicyclic heteroaryl groups, having 1-6 heteroatoms independently selected from the group consisting of O, N and S, optionally substituted with 1-3 substituents independently selected from the group consisting of $R^1$, $OR^1$, $NR^1R^2$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro and also oxides (e.g. =O, —O⁻ or —OH).

(v) saturated and partially saturated $C_3$-$C_6$ monocyclic carbocyclic moiety optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and, nitro;

(vi) saturated and partially saturated $C_8$-$C_{10}$ bicyclic carbocyclic moiety, optionally substituted with 1-3 substituents independently selected from the group consisting of $R^1$, $OR^1$, $NR^1R^2$, $S(O)_qR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro;

(vii) saturated and partially saturated 5 and 6 membered monocyclic heterocyclic moiety, having 1-3 heteroatoms independently selected from the group consisting of O, N and S, optionally substituted with 1-3 substituents independently selected from the group consisting of $R^1$, $OR^1$, $NR^1R^2$, $S(O)_q R^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro, and also oxides (e.g. =O, —O⁻ or —OH); and (viii) saturated and partially saturated 8 to 10 membered bicyclic heterocyclic moiety, having 1-6 heteroatoms independently selected from the group consisting of O, N and S, optionally substituted with 1-3 substituents independently selected from the group consisting of $R^1$, $OR^1$, $NR^1R^2$, $S(O)_q$ $R^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano and nitro, and also oxides (e.g. =O, —O⁻ or —OH).

Each $R^1$-$R^5$ are independently selected from the group consisting of:
(a) hydrogen,
(b) $C_1$-$C_6$ alkyl, preferably, $C_1$-$C_5$ linear, branched, or cyclic alkyl, wherein said alkyl is optionally substituted with halogen up to per-halo;
(c) phenyl;
(d) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S;
(e) $C_1$-$C_3$ alkyl-phenyl wherein said alkyl moiety is optionally substituted with halogen up to per-halo; and
(f) $C_1$-$C_3$ alkyl-heteroaryl having 1-4 heteroatoms selected from the group consisting of O, N and S, wherein said heteroaryl group is a 5-6 membered monocyclic heteroaryl or a 8-10 membered bicyclic heteroaryl, and wherein said alkyl moiety is optionally substituted with halogen up to per-halo.

Each $R^1$-$R^5$, when not hydrogen is optionally substituted with 1-3 substituents independently selected from the group consisting of $C_1$-$C_5$ linear branched or cyclic alkyl, wherein said alkyl is optionally substituted with halogen up to per-halo, $C_1$-$C_3$ alkoxy, wherein said alkoxy is optionally substituted with halogen up to per-halo, hydroxy, amino, $C_1$-$C_3$ alkylamino, $C_2$-$C_6$ dialkylamino, halogen, cyano, and nitro;

Each variable q is independently selected from 0, 1, or 2.

Suitable substituted and unsubstituted heteroaryl groups for the compounds of this invention, such as those for A, B and M of formula I, include, but are not limited to the following monocyclic heteroaryl groups:

2- and 3-furyl, 2- and 3-thienyl, 2- and 4-triazinyl, 1-, 2- and 3-pyrrolyl, 1-, 2-, 4- and 5-imidazolyl, 1-, 3-, 4- and 5-pyrazolyl, 2-, 4- and 5-oxazolyl, 3-, 4- and 5-isoxazolyl, 2-, 4- and 5-thiazolyl, 3-, 4- and 5-isothiazolyl, 2-, 3- and 4-pyridyl, 2-, 4-, 5- and 6-pyrimidinyl, 1,2,3-triazol-1-, -4- and -5-yl, 1,2,4-triazol-1-, -3- and -5-yl, 1- and 5-tetrazolyl, 1,2,3-oxadiazol-4- and -5-yl, 1,2,4-oxadiazol-3- and -5-yl, 1,3,4-thiadiazol-2- and -5-yl, 1,2,4-oxadiazol-3- and -5-yl, 1,3,4-thiadiazol-2- and -5-yl, 1,3,4-thiadiazol-3- and -5-yl, 1,2,3-thiadiazol-4- and -5-yl, 2-, 3-, 4-, 5- and 6-2H-thiopyranyl, 2-, 3- and 4-4H-thiopyranyl, 3- and 4-pyridazinyl, 2-,3-pyrazinyl, and bicyclic heteroaryl groups such as:

Benzofuryl, benzothienyl, indolyl, benzimidazolyl, benzopyrazolyl, benzoxazolyl, benzisoxazolyl, benzothiazolyl, benzisothiazolyl, benz-1,3-oxadiazolyl, quinolinyl, isoquinolinyl, quinazolinyl, tetrahydroquinolinyl, tetrahydroisoquinolinyl, dihydrobenzofuryl, pyrazolo[3,4-b]pyrimidinyl, purinyl, benzodiazine, pterindinyl, pyrrolo[2,3-b]pyridinyl, pyrazolo[3,4-b]pyridinyl, oxazo[4,5-b]pyridinyl, imidazo[4,5-b]pyridinyl, cyclopentenopyridine, cyclohexanopyridine, cyclopentanopyrimidine, cyclohexanopyrimidine, cyclcopentanopyrazine, cyclohexanopyrazine, cyclopentanopyridiazine, cyclohexanopyridazine, cyclopentanoimidazole, cyclohexanoimidazole, cyclopentanothiophene and cyclohexanothiophene.

Suitable aryl groups which do not contain heteroatoms include, for example, phenyl and 1- and 2-naphthyl, tetrahydronaphthyl, indanyl, indenyl, benzocyclobutanyl, benzocycloheptanyl and benzocycloheptenyl.

Suitable linear alkyl groups and alkyl portions of groups, e.g., alkoxy, alkylphenyl and alkylheteroaryl etc. throughout include methyl, ethyl, propyl, butyl, pentyl, etc. Suitable branched alkyl groups include all branched isomers such as isopropyl, isobutyl, sec-butyl, tert-butyl, etc.

Suitable halogen groups include F, Cl, Br, and/or I, from one to per-substitution (i.e. all H atoms on a group replaced by a halogen atom) being possible where an alkyl group is substituted by halogen, mixed substitution of halogen atom types also being possible on a given moiety. Preferred halogens are Cl, Br and F.

The term "up to perhalo substituted linear and branched alkyl," includes alkyl groups having one alkyl hydrogen replaced with halogen, alkyl groups wherein all hydrogens are replaced with halogen, alkyl groups wherein more than one but less than all hydrogens are replaced by halogen and alkyl groups having alkyl hydrogens replaced by halogen and other substituents.

The term "cycloalkyl", as used herein, refers to cyclic structures having 3-8 members in the ring such as cyclopropyl, cyclobutyl and cyclopentyl and cyclic structures having 3-8 members with alkyl substituents such that, for example, "$C_3$ cycloalkyl" includes methyl substituted cyclopropyl groups.

The term "saturated carbocyclic moieties" defines only the cyclic structure, i.e. cyclopentyl, cyclohexyl, etc. Any alkyl substitution on these cyclic structures is specifically identified.

Saturated monocyclic and bicyclic carbocyclic moieties include cyclopropyl, cyclobutyl, cyclopentyl, cyclohexyl, and decahydronapthalene.

Partially saturated monocyclic and bicyclic carbocyclic moieties include cyclopentenyl, cyclohexenyl, cyclohexadienyl and tetrahydronaphthalene.

Saturated monocyclic and bicyclic heterocyclic moieties include tetrahydropyranyl, tetrahydrofuranyl, 1,3-dioxolane, 1,4-dioxanyl, morpholinyl, thiomorpholinyl, piperazinyl, piperidinyl, piperidinonyl, tetrahydropyrimidonyl, pentamethylene sulfide and tetramethylene sulfide.

Partially saturated monocyclic and bicyclic heterocyclic moieties include dihydropyranyl, dihydrofuranyl, dihydrothienyl, dihydropiperidinyl, and dihydropyrimidonyl.

A subclass of compounds of this invention is defined by formula I, wherein A B and M are selected from phenyl, naphthyl, furyl, isoindolinyl, oxadiazolyl, oxazolyl, isooxazolyl, pyrazolyl, pyridinyl, pyrimidinyl, pyrrolyl, quinolinyl, tetrazolyl, thiadiazolyl, thiazolyl and thienyl and are optionally substituted as defined above.

Preferred substituents for B include methyl, trifluoromethyl, ethyl, n-propyl, n-butyl, n-pentyl, isopropyl, isobutyl, sec-butyl, tert-butyl, cyclopropyl, cyclobutyl, cyclopentyl, methoxy, ethoxy, propoxy, Cl, Br and F, cyano, nitro, hydroxy, amino, methylamino, dimethylamino, ethylamino and diethylamino as well as the structure -L-M.

Preferred substituents for A and M include methyl, trifluoromethyl, ethyl, n-propyl, n-butyl, n-pentyl, isopropyl, textbutyl, sec-butyl, isobutyl, cyclopropyl, cyclobutyl, cyclopentyl, methoxy, ethoxy, propoxy, Cl, Br and F, cyano, nitro, hydroxy, amino, methylamino, dimethylamino, ethylamino and diethylamino and further include:

phenyl, pyridinyl, pyrimidinyl, chlorophenyl, dichlorophenyl, bromophenyl, dibromophenyl, chloropyridinyl, bromopyridinyl, dichloropyridinyl, dibromopyridinyl methylphenyl, methylpyridinyl quinolinyl, isoquinolinyl, isoindolinyl, pyrazinyl, pyridazinyl, pyrrolyl, imidazolinyl, thienyl, furyl, isoxazolinyl, isothiazolinyl, benzopyridinyl, benzothiazolyl, $C_1$-$C_5$ acyl;
NH($C_1$-$C_5$ alkyl, phenyl or pyridinyl), such as aminophenyl;
N($C_1$-$C_5$ alkyl)($C_1$-$C_5$ alkyl, phenyl or pyridinyl), such as diethylamino and dimethyl amino;
S(O)$_q$ ($C_1$-$C_5$ alkyl); such as methanesulfonyl;
S(O)$_q$H;
SO$_2$NH$_2$;
SO$_2$NH($C_1$-$C_5$ alkyl);
SO$_2$N($C_1$-$C_5$ alkyl)($C_1$-$C_5$ alkyl);
NHSO$_2$($C_1$-$C_5$ alkyl); N($C_1$-$C_3$ alkyl) SO$_2$($C_1$-$C_5$ alkyl);
CO($C_1$-$C_6$ alkyl or phenyl);
C(O)H;
C(O)O($C_1$-$C_6$ alkyl or phenyl), such as C(O)OCH$_3$, —C(O)OCH$_2$CH$_3$, —C(O)OCH$_2$CH$_2$CH$_3$;
C(O)OH;
C(O)NH$_2$ (carbamoyl);
C(O)NH($C_1$-$C_6$ alkyl or phenyl), such as N-methylethyl carbamoyl, N-methyl carbamoyl, N-ethylcarbamoyl, or N-dimethylamino ethyl carbamoyl;
C(O)N($C_1$-$C_6$ alkyl or phenyl)($C_1$-$C_6$ alkyl, phenyl or pyridinyl), such as N-dimethyl carbamoyl;
C(N($C_1$-$C_5$ alkyl)) ($C_1$-$C_5$ alkyl);
NHC(O)($C_1$-$C_6$ alkyl or phenyl) and
N($C_1$-$C_5$ alkyl,)C(O)($C_1$-$C_5$ alkyl).

Each of the above substituents is optionally partially or fully halogenated, such as difluoromethyl sulfonyl.

An embodiment of this invention includes the administration of compounds of this invention wherein in formula I, A, B and M follow one of the following of combinations:

A=phenyl, B=phenyl and M is phenyl, pyridinyl, quinolinyl, isoquinolinyl or not present,
A=phenyl, B=pyridinyl and M is phenyl, pyridinyl, quinolinyl, isoquinolinyl or not present,
A=phenyl, B=naphthyl and M is phenyl, pyridinyl, quinolinyl, isoquinolinyl or not present,
A=pyridinyl, B=phenyl and M is phenyl, pyridinyl, quinolinyl, isoquinolinyl or not present,
A=pyridinyl, B=pyridinyl and M is phenyl, pyridinyl, quinolinyl, isoquinolinyl or not present,
A=pyridinyl, B=naphthyl and M is phenyl, pyridinyl, quinolinyl, isoquinolinyl or not present,
A=isoquinalinyl, B=phenyl and M is phenyl, pyridinyl, quinolinyl, isoquinolinyl or not present,
A=isoquinolinyl, B=pyridinyl and M is phenyl, pyridinyl, quinolinyl, isoquinolinyl or not present,
A=isoquinolinyl, B=naphthyl and M is phenyl, pyridinyl, quinolinyl, isoquinolinyl or not present,
A=quinolinyl, B=phenyl and M is phenyl, pyridinyl, quinolinyl, isoquinolinyl or not present,
A=quinolinyl, B=pyridinyl and M is phenyl, pyridinyl, quinolinyl, isoquinolinyl or not present,
A=quinolinyl, B=naphthyl and M is phenyl, pyridinyl, quinolinyl, isoquinolinyl or not present.

The structure L of formula I is preferably —O—, a single bond, —S—, —NH—, —N(CH$_3$)—, —NHCH$_2$—, NC$_2$H$_4$—, —CH$_2$—, —C(O)—, —CH(OH)—, —NHC(O)N(CH$_3$)CH$_2$—, N(CH$_3$)C(O)N(CH$_3$)CH$_2$—, —CH$_2$C(O)N(CH$_3$)—, —C(O)N(CH$_3$)CH$_2$—, —NHC(O)—, —N(CH$_3$)C(O)—, —C(O)N(CH$_3$)—, —C(O)NH—, —CH$_2$O—, —CH$_2$S—, —CH$_2$N(CH$_3$)—, —OCR$_2$—, —CHF—, —CF$_2$—, —CCl$_2$—, —S—CH$_2$—, and —N(CH$_3$)CH$_2$—.

One of ordinary skill in the art will recognize that some of the compounds of Formula (I) can exist in different geometrical isomeric forms. A number of the compounds of Formula I possess asymmetric carbons and can therefore exist in racemic and optically active forms as well as in the form of racemic or non-racemic mixtures thereof, and in the form of diastereomers and diastereomeric mixtures. All of these compounds, including cis isomers, trans isomers, diastereomic mixtures, racemates, non-racemic mixtures of enantiomers, substantially pure, and pure enantiomers, are considered to be within the scope of the present invention and are collectively referred to when reference is made to compounds of this invention.

Methods of separation of enantiomeric and diastereomeric mixtures are well known to one skilled in the art. The optical isomers can be obtained by resolution of the racemic mixtures according to conventional processes, for example, by the formation of diastereoisomeric salts using an optically active acid or base. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical chemical differences by methods known to those skilled in the art, for example, by chromatography or fractional crystallization. The optically active bases or acids are liberated from the separated diastereomeric salts.

Another process for separation of optical isomers involves the use of a chiral chromatography column (e.g., chiral HPLC columns) optimally chosen to maximize the separation of the enantiomers. Suitable chiral HPLC columns are manufactured by Diacel, e.g., Chiracel OD and Chiracel OJ. The optically active compounds of Formula (I) can likewise be obtained by utilizing optically active starting materials.

The present invention encompasses any isolated racemic or optically active form of compounds described in Formula I which possess angiogenesis inhibitory activity. The term stereoisomer is understood to encompass diastereoisomers, enantiomers, geometric isomers, etc. Herein, substantially pure enantiomers is intended to mean that no more than 5% w/w of the corresponding opposite enantiomer is present.

Pharmaceutically acceptable salts of these compounds as well as commonly used prodrugs of these compounds are also within the scope of the invention.

Salts are especially the pharmaceutically acceptable salts of compounds of formula (I) or such as, for example, organic or inorganic acid addition salts of compounds of formula (I). Suitable inorganic acids include but are not limited to halogen acids (such as hydrochloric acid and hydrobromic acid), sulfuric acid, or phosphoric acid. Suitable organic acids include but are not limited to carboxylic, phosphonic, sulfonic, or sulfamic acids, with examples including acetic acid, propionic acid, octanoic acid, decanoic acid, trifluoroacetic acid, dodecanoic acid, glycolic acid, lactic acid, 2- or 3-hydroxybutyric acid, -γ-aminobutyric acid (GABA), gluconic acid, glucosemonocarboxylic acid, benzoic acid, salicylic acid, phenylacetic acid and mandelic acid, fumaric acid, succinic acid, adipic acid, pimelic acid, suberic acid, azeiaic acid, malic acid, tartaric acid, citric acid, glucaric acid, galactaric acid, amino acids (such as glutamic acid, aspartic acid, N-methylglycine, acetylaminoacetic acid, N-acetylasparagine or N-acetylcysteine), pyruvic acid, acetoacetic acid, methanesulfonic acid, tri-fluoromethane sulfonic acid, 4-toluene sulfonic acid, benzenesulfonic acid, 1-naphthalenesulfonic acid, 2-naphthalenesulfonic acid, phosphoserine, and 2- or 3-glycerophosphoric acid.

In addition, pharmaceutically acceptable salts include acid salts of inorganic bases, such as salts containing alkaline cations (e.g., Li$^+$ Na$^+$ or K$^+$), alkaline earth cations (e.g., Mg$^{+2}$, Ca$^{+2}$ or Ba$^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

The formation of prodrugs is well known in the art in order to enhance the properties of the parent compound; such properties include solubility, absorption, biostability and release time (see "*Pharmaceutical Dosage Form and Drug Delivery Systems*" (Sixth Edition), edited by Ansel et al., published by Williams & Wilkins, pages 27-29, (1995) which is hereby incorporated by reference). Commonly used prodrugs of the disclosed oxazolyl-phenyl-2,4-diamino-pyrimidine compounds are designed to take advantage of the major drug biotransformation reactions and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation and acetylation (see Goodman and Gilman's *The Pharmacological Basis of Therapeutics* (Ninth Edition), editor Molinoff et al., pub. by McGraw-Hill, pages 11-13, (1996), which is hereby incorporated by reference).

The invention also relates to methods for treating and preventing diseases, for example, angiogenesis disorders in mammals by administering a compound of this invention or a pharmaceutical composition comprising one or more compounds of this invention.

A compound according to the invention can be administered simultaneously with another angiogenesis inhibiting agent to a patient with such a disorder, in the same formulation or, more typically in separate formulations and, often, using different administration routes. Administration can also be sequentially, in any order.

A compound according to the invention can be administered in tandem with another angiogenesis inhibiting agent, wherein a compound according to the invention can be administered to a patient once or more per day for up to 28 consecutive days with the concurrent or intermittent administration of another angiogenesis inhibiting agent over the same total time period.

A compound according to the invention can be administered to a patient at an oral, intravenous, intramuscular, subcutaneous, or parenteral dosage which can range from about 0.1 to about 200 mg/kg of total body weight and the additional angiogenesis inhibiting agent can be administered to a patient at an intravenous, intramuscular, subcutaneous, or parenteral dosage which can range from about 0.1 mg to 200 mg/kg of patient body weight.

An embodiment of the present invention is a method for treating diseases in humans and/or other mammals which are mediated by the VEGF induced signal transduction pathway which comprises administering a compound of this invention to a human or other mammal.

Another embodiment of this invention is a method for treating diseases in humans and/or other mammals which are characterized by abnormal angiogenesis or hyperpermiability processes with a compound of this invention to a human or other mammal.

Another embodiment of this invention is a method for treating diseases in humans and/or other mammals which are characterized by abnormal angiogenesis or hyperpermiability processes, which are not raf-mediated, which comprises administering a compound of this invention to a human or other mammal.

Another embodiment of this invention is a method for treating diseases in humans and/or other mammals which are characterized by abnormal angiogenesis or hyperpermiability processes, which are not raf mediated or p38-mediated, which comprises administering a compound of this invention to a human or other mammal.

Another embodiment of this invention is a method for treating diseases in humans and/or other mammals which are characterized by abnormal angio genesis or hyperpeuniability processes, which are raf-mediated and/or p38 mediated, which comprises administering a compound of this invention to a human or other mammal.

Another embodiment of this invention is a method for treating one or more of the following conditions in humans and/or other mammals: tumor growth, retinopathy, including diabetic retinopathy, ischemic retinal-vein occlusion, retinopathy of prematurity and age related macular degeneration; rheumatoid arthritis, psoriasis, or bullous disorder associated with subepidermal blister formation, including bullous pemphigoid, erythema multiforme, or dermatitis herpetiformis, which comprises administering a compound of this invention to a human or other mammal with one or more of these conditions.

Another embodiment of this invention is a method for treating one or more of the following conditions in humans and/or other mammals: tumor growth, retinopathy, diabetic retinopathy, ischemic retinal-Vein occlusion, retinopathy of prematurity, age related macular degeneration; rheumatoid arthritis, psoriasis, bullous disorder associated with subepidermal blister formation, bullous pemphigoid, erythema multiform; and dermatitis herpetiformis in combination with another condition selected from the group consisting of:

rheumatic fever, bone resorption, postmenopausal osteoporosis, sepsis, gram negative sepsis, septic shock, endotoxic shock, toxic shock syndrome, systemic inflammatory response syndrome, inflammatory bowel disease (Crohn's disease and ulcerative colitis), Jarisch-Herxheimer reaction, asthma, adult respiratory distress syndrome, acute pulmonary fibrotic disease, pulmonary sarcoidosis, allergic respiratory disease, silicosis, coal worker's pneumoconiosis, alveolar injury, hepatic failure, liver disease during acute inflammation, severe alcoholic hepatitis, malaria (*Plasmodium falciparum* malaria and cerebral malaria), non-insulin-dependent diabetes mellitus (NIDDM), congestive heart failure, damage following heart disease, atherosclerosis, Alzheimer's disease, acute encephalitis, brain injury, multiple sclerosis (demyelation and oligiodendrocyte loss in multiple sclerosis), advanced cancer, lymphoid malignancy, pancreatitis, impaired wound healing in infection, inflammation and cancer, myelodysplastic syndromes, systemic lupus erythematosus, biliary cirrhosis, bowel necrosis, radiation injury/toxicity following administration of monoclonal antibodies, host-versus-graft reaction (ischemia reperfusion injury and allograft rejections of kidney, liver, heart, and skin), lung allograft rejection (obliterative bronchitis) or complications due to total hip replacement. This method comprises administering a compound of this invention to a human or other mammal with one of the above combinations of conditions.

Another embodiment of this invention is a method for treating one or more of the following conditions in humans and/or other mammals:

tumor growth, retinopathy, diabetic retinopathy, ischemic retinal-vein occlusion, retinopathy of prematurity, age related macular degeneration; rheumatoid arthritis, psoriasis, bullous disorder associated with subepidermal blister formation, bullous pemphigoid, erythema multiforme, and dermatitis herpetiformis, in combination with an infectious disease selected from the group consisting of:

tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia burgdorferi, Treponema pallidum*, cytomegalovirus, influenza virus, Theiler's encephalomyelitis virus, and the human immunodeficiency virus (HIV). These methods comprise administering a compound of this invention to a human or other mammal with a combination of one of the above infectious diseases and one of the above diseases characterized by abnormal angiogenesis or hyperpermiability processes.

This invention further relates to kits comprising separate doses of the two mentioned chemotherapeutic agents in separate containers. The combinations of angiogenesis inhibiting agents can also be formed in vivo, e.g., in a patient's body.

These angiogenesis inhibiting agents can be administered in the conventional formulations and regimens in which they are known for use alone.

Conditions within a human or other mammal which can be treated by administering a compound of this invention are those characterized by abnormal angiogenesis or hyperpermiability processes. Conditions to be treated include tumor growth, retinopathy, including diabetic retinopathy, ischemic retinal-vein occlusion, retinopathy of prematurity and age related macular degeneration; rheumatoid arthritis, psoriasis, or a bullous disorder associated with subepidermal blister formation, including bullous pemphigoid, erythema multiforme, and dermatitis herpetiformis.

Methods of interest include the treatment of combinations of the conditions above (tumor growth, retinopathy, diabetic retinopathy, ischemic retinal-vein occlusion, retinopathy of prematurity, age related macular degeneration; rheumatoid arthritis, psoriasis, bullous disorder associated with subepidermal blister formation, bullous pemphigoid, erythema multiforme, and dermatitis herpetiformis) and another condition selected from the group consisting of:

rheumatic fever, bone resorption, postmenopausal osteoperosis, sepsis, gram negative sepsis, septic shock, endotoxic shock, toxic shock syndrome, systemic inflammatory response syndrome, inflammatory bowel disease (Crohn's disease and ulcerative colitis), Jarisch-Herxheimer reaction, asthma, adult respiratory distress syndrome, acute pulmonary fibrotic disease, pulmonary sarcoidosis, allergic respiratory disease, silicosis, coal worker's pneumoconiosis, alveolar injury, hepatic failure, liver disease during acute inflammation, severe alcoholic hepatitis, malaria (*Plasmodium falciparum* malaria and cerebral malaria), non-insulin-dependent diabetes mellitus (NIDDM), congestive heart failure, damage following heart disease, atherosclerosis, Alzheimer's disease, acute encephalitis, brain injury, multiple sclerosis (demyelation and oligiodendrocyte loss in multiple sclerosis), advanced cancer, lymphoid malignancy, pancreatitis, impaired wound healing in infection, inflammation and cancer, myelodysplastic syndromes, systemic lupus erythematosus, biliary cirrhosis, bowel necrosis, radiation injury/toxicity following administration of monoclonal antibodies, host-versus-graft reaction (ischemia reperfusion injury and allograft rejections of kidney, liver, heart, and skin), lung allograft rejection (obliterative bronchitis) or complications due to total hip replacement.

Also provided is a method for treating combinations of the conditions above (tumor growth, retinopathy, diabetic retinopathy, ischemic retinal-vein occlusion, retinopathy of prematurity, age related macular degeneration; rheumatoid arthritis, psoriasis, bullous disorder associated with subepidermal blister formation, bullous pemphigoid, erythema multiforme, and dermatitis herpetiformis) and an infectious disease selected from the group consisting of:

tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia burgdorferi, Treponema pallidum*, cytomegalovirus, influenza virus, Theiler's encephalomyelitis virus, and the human immunodeficiency virus (HIV).

The compounds of this invention can be made according to conventional chemical methods, and/or as disclosed below, from starting materials which are either commercially available or producible according to routine, conventional chemical methods. General methods for the preparation of the compounds are given below, and the preparation of a suitable compound is specifically illustrated in the Examples.

Ureas of formula (I) can be prepared by a variety of simple methods known in the art. General approaches for the formation of those compounds can be found in "*Advanced Organic Chemistry*", by J. March, John Wiley and Sons, 1985 and in "*Comprehensive Organic Transformations*", by R. C. Larock, VCH Publishers, 1989), which are hereby incorporated by reference. Nevertheless, the following general preparative methods are presented to aid one of skill in the art in synthesizing these compounds, with more detailed examples being presented in the experimental section describing the working examples.

General Preparative Methods

Heterocyclic amines may be synthesized utilizing known methodology (Katritzky, et al. *Comprehensive Heterocyclic Chemistry*; Permagon Press: Oxford, UK (1984). March. *Advanced Organic Chemistry*, $3^{rd}$ Ed.; John. Wiley: New York (1985)). For example, as shown in Scheme 1,5-aminopyrazoles substituted at the N-1 position with either aryl or heteroaryl moieties may be synthesized by the reaction of an α-cyanoketone (2) with the appropriate aryl- or heteroaryl hydrazine (3, $R^2$=aryl or heteroaryl). Cyanoketone 2, in turn, is available from the reaction of acetamidate ion with an appropriate acyl derivative, such as an ester, an acid halide, or an acid anhydride. In cases where the $R^2$ moiety offers suitable anion stabilization, 2-aryl- and 2-heteroarylfurans may be synthesized from a Mitsunobu reaction of cyanoketone 2 with alcohol 5, followed by base catalyzed cyclization of enol ether 6 to give furylamine 7.

Scheme I. Selected General Methods for Heterocyclic Amine Synthesis

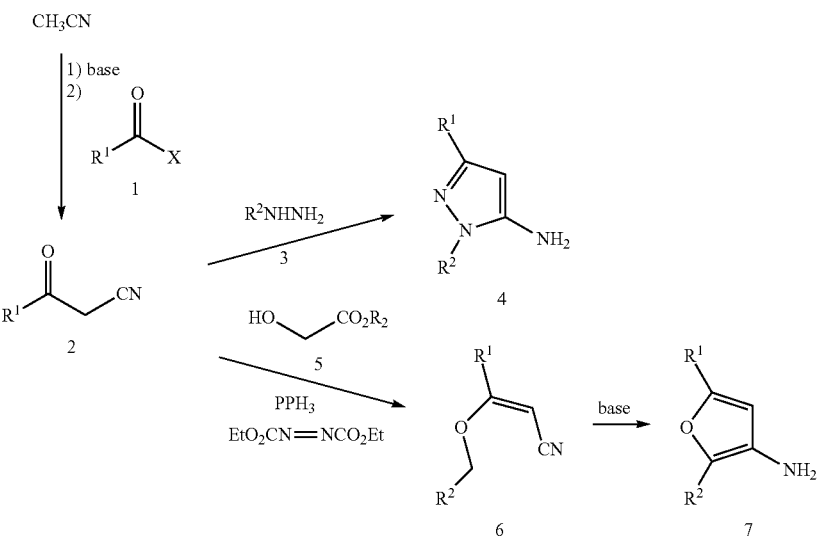

Substituted anilines may be generated using standard methods (March. *Advanced Organic Chemistry*, 3rd Ed.; John Wiley: New York (1985). Larock. *Comprehensive Organic Transformations*; VCH Publishers: New York (1989)). As shown in Scheme II, aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino- and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, 3rd Ed.; John Wiley: New York (1985). Larock. *Comprehensive Organic Transformations*; VCH Publishers: New York (1989)).

Scheme II Reduction of Nitroaryls to Aryl Amines

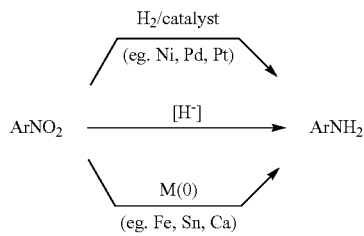

Nitroaryls are commonly formed by electrophilic aromatic nitration using $HNO_3$, or an alternative $NO_2^+$ source. Nitro aryls may be further elaborated prior to reduction. Thus, nitroaryls substituted with

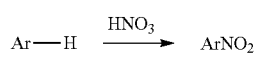

potential leaving groups (eg. F, Cl, Br, etc.) may undergo substitution reactions on treatment with nucleophiles, such as thiolate (exemplified in Scheme III) or phenoxide. Nitroaryls may also undergo Ullman-type coupling reactions (Scheme III).

Scheme III Selected Nucleophilic Aromatic Substitution using Nitroaryls

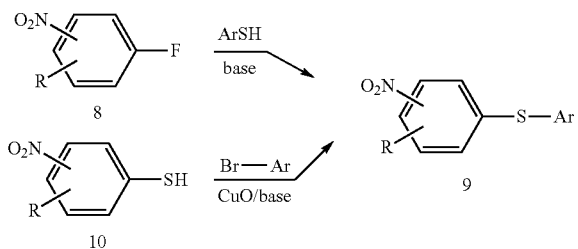

As shown in Scheme IV, urea formation may involve reaction of a heteroaryl isocyanate (12) with an aryl amine (11). The heteroaryl isocyanate may be synthesized from a heteroaryl amine by treatment with phosgene or a phosgene equivalent, such as trichloromethyl chloroformate (diphosgene), bis(trichloromethyl) carbonate (triphosgene), or N,N'-carbonyldiimidazole (CDT). The isocyanate may also be derived from a heterocyclic carboxylic acid derivative, such as an ester, an acid halide or an anhydride by a Curtius-type rearrangement. Thus, reaction of acid derivative 16 with an azide source, followed by rearrangement affords the isocyanate. The corresponding carboxylic acid (17) may also be subjected to Curtius-type rearrangements using diphenylphosphoryl azide (DPPA) or a similar reagent. A urea may also be generated from the reaction of an aryl isocyanate (15) with a heterocyclic amine.

Scheme IV Selected Methods of Urea Formation (Het = heterocycle)

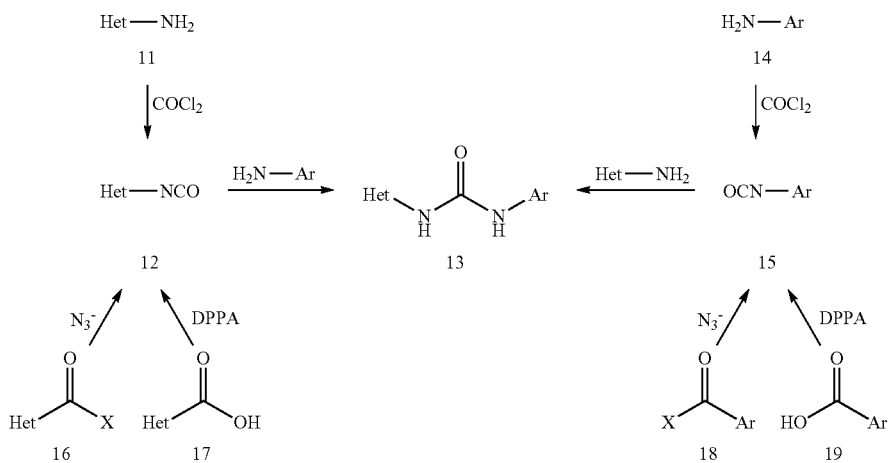

ureas may be further manipulated using methods familiar to those skilled in the art. For example, 2-aryl and 2-heteroarylthienyl ureas are available from the corresponding 2-halothienyl urea through transition metal mediated cross coupling reactions (exemplified with 2-bromothiophene 25, Scheme V). Thus, reaction of nitrile 20 with an α-thioacetate ester gives 5-substituted-3-amino-2-thiophenecarboxylate 21 (Ishizaki et al. JP 6025221). Decarboxylation of ester 21 may be achieved by protection of the amine, for example as the tert-butoxy (BOC) carbamate (22), followed by saponification and treatment with acid. When BOC protection is used, decarboxylation may be accompanied by deprotection giving the substituted 3-thiopheneammonium salt 23. Alternatively, ammonium salt 23 may be directly generated through saponification of ester 21 followed by treatment with acid. Following urea formation as described above, bromination affords penultimate halothiophene 25. Palladium mediated cross coupling of thiophene 25 with an appropriate tributyl- or trimethyltin ($R^2$=aryl or heteroaryl) then affords the desired 2-aryl- or 2-heteroarylthienyl urea.

Scheme V Synthesis and Interconversion of Ureas

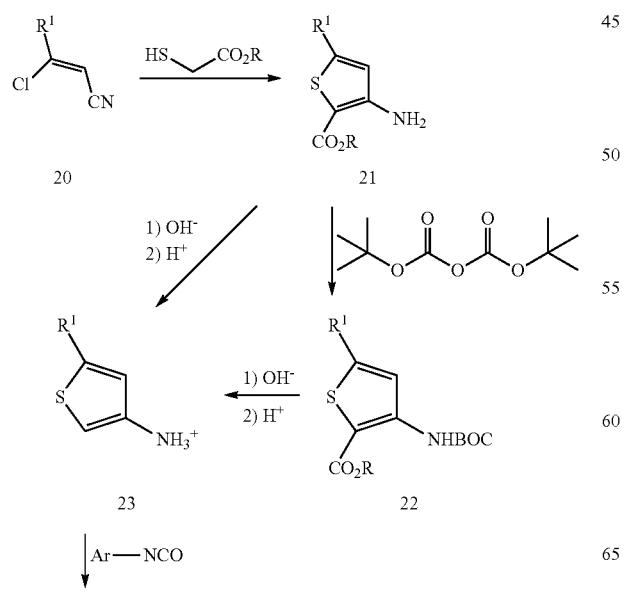

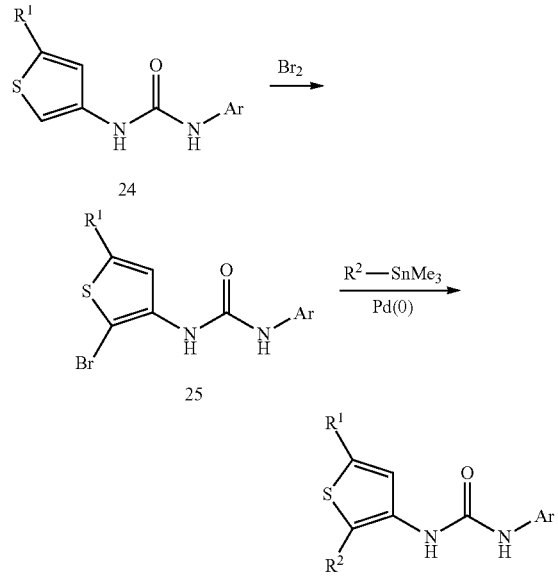

Finally, ureas may be further manipulated using methods familiar to those skilled in the art.

The compounds may be administered orally, topically, parenterally, by inhalation or spray or vaginally, sublingually, or rectally in dosage unit formulations.

The term 'administration by injection' includes intravenous, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, microcrystalline cellulose, carboxymethyl cellulose, hydroxypropylmethylcellulose or alginic acid; and binding agents, for example magnesium stearate, stearic acid or talc and lubricants/surfactants such as sodium lauryl sulfate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administrated transdermally using methods known to those skilled in the art (see, for example: Chien; "Transdermal Controlled Systemic Medications"; Marcel Dekker, Inc.; 1987. Lipp et al. WO94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or 1-0 unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene coplymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily vaginal dosage regimen will preferably be from 0.01 to 200 mg/Kg of total body weight. The daily rectal dosage regime will preferably be from 0.01 to 200 mg/Kg of total body weight. The daily topical dosage regime will preferably be from 0.1 to 200 mg administered between one to four times daily. The transdermal concentration will preferably be that required to maintain a daily dose of from 0.01 to 200 mg/Kg. The daily inhalation dosage regime will preferably be from 0.01 to 10 mg/Kg of total body weight. These dosages regimes can be achieved with multiple dosages within a single day or extended dosages, such as those given on a weekly or monthly basis.

It will be appreciated by those skilled in the art that the particular method of administration will depend on a variety of factors, all of which are considered routinely when administering therapeutics. It will also be appreciated by one skilled in the art that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy.

It will be further appreciated by one skilled in the art that the optimal course of treatment, i.e., the mode of treatment and the daily number of doses of a compound of this invention given for a defined number of days, can be ascertained by those skilled in the art using conventional treatment tests.

It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the condition undergoing therapy.

Specific preparations of the compounds of this invention are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Inhibition of RAF Kinase Activity using Substituted Heterocyclic Ureas" PCT Int, Appl., WO 99 32106, Dumas, J. et al., "Method for the Treatment of Neoplasm by Inhibition of raf Kinase using N-Heteroaryl-N'-(hetero)arylureas" PCT Int. Appl., WO 99 32106, Dumas, S. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedi, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698.

Methods for preparaing the compounds of this invention are also described in the following U.S. applications, some of which correspond to the PCT applications listed above.

Ser. No. 08/863,022, filed May 23, 1997;
Ser. No. 08/996,344, filed Dec. 22, 1997;
Ser. No. 08/996,343, filed Dec. 22, 1997;
Ser. No. 08/996,181, filed Dec. 22, 1997;
Ser. No. 08/995,749, filed Dec. 22, 1997;
Ser. No. 08/995,750, filed Dec. 22, 1997;
Ser. No. 08/995,751, filed Dec. 22, 1997;
Ser. No. 09/083,399, filed May 22, 1998;
Ser. No. 09/425,228, filed Oct. 22, 1999;
Ser. No. 09/777,920, filed Feb. 7, 2001.
Ser. No. 09/722,418 filed Nov. 28, 2000
Ser. No. 09/838,285, filed Apr. 20, 2001;
Ser. No. 09/838,286, filed Apr. 20, 2001;
Ser. No. 09/458,548, filed Jan. 12, 2001;
Ser. No. 09/948,915, filed Sep. 10, 2001, and
Ser. No. 60/334,609, filed Dec. 3, 2001.

The entire disclosure of all applications, patents and publications cited above 1.0 and below are hereby incorporated by reference.

The compounds of this invention are producible from known compounds (or from starting materials which, in turn, are producible from known compounds), e.g., through the general preparative methods shown below. The activity of a given compound to inhibit angiogenesis activity can be routinely assayed, e.g., according to procedures disclosed below.

Without further elaboration, it is believed that one skilled in the art can, using the preceding description, utilize the present invention to its fullest extent. The following examples are, therefore, to be construed as merely illustrative and not imitative of the remainder of the disclosure in any way whatsoever. The following examples are for illustrative purposes only and are not intended, nor should they be construed to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg.

All temperatures are reported uncorrected in degrees Celsius (° C.). Unless otherwise indicated, all parts and percentages are by weight.

Commercial grade reagents and solvents were used without further purification.

Thin-layer chromatography (TLC) was performed on Whatman® pre-coated glass-backed silica gel 60A F-254 250 μm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was' performed using 230-400 mesh EM Science® silica gel.

Melting points (mp) were determined using a Thomas-Hoover Melting point apparatus or a Mettler FP66 automated melting point apparatus and are uncorrected. Proton ($^1$H) nuclear magnetic resonance (NMR) spectra were measured with a General Electric GN-Omega 300 (300 MHz) spectrometer with either Me$_4$Si (δ 0.00) or residual protonated solvent (CHCl$_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent (CDCl$_3$ δ 77.0; MeOD-d$_3$; δ 49.0; DMSO-d$_6$ δ 39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment were obtained using a Kratos Concept 1-H spectrometer.

Chemical ionization mass spectra (CI-MS) were obtained using a Hewlett Packard MS-Engine (5989A) with methane as the reagent gas ($1 \times 10^{-4}$ torr to $2.5 \times 10^{-4}$ torr). The direct insertion desorption chemical ionization (DCI) probe (Vaccumetrics, Inc.) was ramped from 0-1.5 amps in 10 sec and held at 10 amps until all traces of the sample disappeared (~1-2 min). Spectra were scanned from 50-800 amu at 2 sec per scan. HPLC electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120-800 amu using a variable ion time according to the number of ions in the source.

Gas chromatography-ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV).

Elemental analyses were conducted by Robertson Microlit Labs, Madison N.J. All compounds displayed NMR spectra, LRMS and either elemental analysis or HRMS consistent with assigned structures.

LIST OF ABBREVIATIONS AND ACRONYMS

AcOH acetic acid
anh anhydrous
BOC tert-butoxycarbonyl
conc concentrated
dec decomposition
DMPU 1,3-dimethyl-3,4,5,6-tetrahydro-2(1H)-pyrimidinone
DMF N,N-dimethylformamide
DMSO dimethylsulfoxide
DPPA diphenylphosphoryl azide
EtOAc ethyl acetate
EtOH ethanol (100%)
Et$_2$O diethyl ether
Et$_3$N triethylamine
m-CPBA 3-chloroperoxybenzoic acid
MeOH methanol
pet. ether petroleum ether (boiling range 30-60° C.)
THF tetrahydrofuran
TFA trifluoroacetic acid
Tf trifluoromethanesulfonyl Example A N-[4-chloro-3-(trifluoromethyl)phenyl]-N-{4-[2-carbamoyl-(4-yridyloxy)]phenyl}urea Step 1: Preparation of 4-chloro-2-pyridinecarboxamide

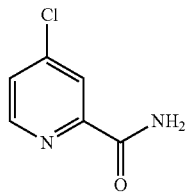

To a stirred mixture of methyl 4-chloro-2-pyridinecarboxylate hydrochloride (1.0 g, 4.81 mmol) dissolved in conc. aqueous ammonia (32 mL) was added ammonium chloride (96.2 mg, 1.8 mmol, 037 equiv.), and the heterogeneous reaction mixture was stirred at ambient temperature for 16 h. The reaction mixture was poured into EtOAc (500 mL) and water (300 mL). The organic layer was washed with water (2×300 mL) and a saturated NaCl solution (1×300 mL), dried (MgSO$_4$), concentrated in vacuo to give 4-chloro-2-pyridinecarboxamide as a beige solid (604.3 mg, 80.3%): TLC (50% EtOAc/hexane) R$_f$ 0.20; $^1$H-NMR (DMSO-d$_6$) δ 8.61 (d, J=5.4 Hz, 1H), 8.20 (broad s, 1H), 8.02 (d, J=1.8 Hz, 1H), 7.81 (broad s, 1H), 7.76 to 7.73 (m, 1H).

Step 2: Preparation of 4-(4-aminophenoxy)-2-pyridinecarboxamide

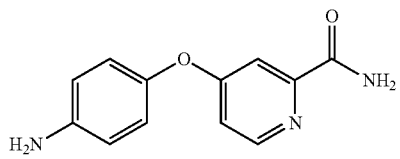 [SMILES: NC(=O)c1cc(Oc2ccc(N)cc2)ccn1]

To 4-aminophenol (418 mg, 3.83 mmol) in anh DMF (7.7 mL) was added potassium tert-butoxide (447 mg, 3.98 mmol, 1.04 equiv.) in one portion. The reaction mixture was stirred at room temperature for 2 h, and a solution of 4-chloro-2-pyridinecarboxamide (600 mg, 3.83 mmol, 1.0 equiv.) in anh DMF (4 mL) was then added. The reaction mixture was stirred at 80° C. for 3 days and poured into a mixture of EtOAc and a saturated NaCl solution. The organic layer was sequentially washed with a saturated NH$_4$Cl solution then a saturated NaCl solution, dried (MgSO$_4$), and concentrated under reduced pressure. The crude product was purified using MPLC chromatography (Biotage®; gradient from 100%

EtOAc to followed by 10% MeOH/50% EtOAc/40% hexane) to give the 4-chloro-5-trifluoromethylaniline as a brown solid (510 mg, 58%). $^1$H-NMR (DMSO-d$_6$) δ 8.43 (d, J=5.7 Hz, 1H), 8.07 (br s, 1H), 7.66 (br s, 1H), 7.31 (d, J=2.7 Hz, 1H), 7.07 (dd, J=5.7 Hz, 2.7 Hz, 1H), 6.85 (d, J=9.0 Hz, 2H), 6.62 (d, J=8.7 Hz, 2H), 5.17 (broad s, 2H); HPLC EI-MS m/z 230 ((M+H)$^+$.

Step 3: Preparation of N-[4-chloro-3-(trifluoromethyl)phenyl]-M-{4-[2-carbamoyl-(4-pyridyloxy)]phenyl}urea

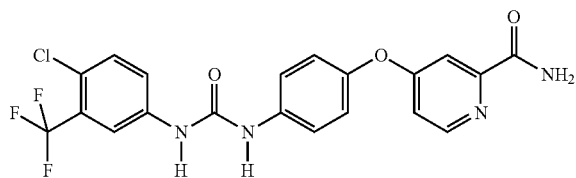 [SMILES: NC(=O)c1cc(Oc2ccc(NC(=O)Nc3ccc(Cl)c(C(F)(F)F)c3)cc2)ccn1]

A mixture of 4-chloro-5-trifluoromethylaniline (451 mg, 2.31 mmol, 1.1 equiv.) and 1,1'-carbonyl diimidazole (419 mg, 2.54 mmol, 1.2 equiv.) in anh dichloroethane (5.5 mL) was stirred under argon at 65° C. for 16 h. Once cooled to room temperature, a solution of 4-(4-aminophenoxy)-2-pyridinecarboxamide (480 mg, 2.09 mmol) in anh THF (4.0 mL) was added, and the reaction mixture was stirred at 60° C. for 4 h. The reaction mixture was poured into EtOAc, and the organic layer was washed with water (2×) and a saturated NaCl solution (1×), dried (MgSO$_4$), filtered, and evaporated in vacuo. Purification using MPLC chromatography (Biotage®; gradient from 100% EtOAc to 2% MeOH/EtOAc) gave N-[4-chloro-3-(trifluoromethyl)phenyl]-N'-{4-[2-carbamoyl-(4-pyridyloxy)]phenyl}urea as a white solid (770 mg, 82%): TLC (EtOAc) R$_f$ 0.11, 100% ethyl acetate $^1$H-NMR (DMSO-d$_6$) δ 9.21 (s, 1H), 8.99 (s, 1H), 8.50 (d, J=5.6 Hz, 1H), 8.11 (s, 1H), 8.10 (s, 1H), 7.69 (broad s, 1H), 7.64 (dd, J=8.2 Hz, 2.1 Hz, 1H), 7.61 (s, 1H), 7.59 (d, J=8.8 Hz, 2H), 7.39 (d, J=2.5 Hz, 1H), 7.15 (d, J=8.9 Hz, 2H), 7.14 (m, 1H); MS LC-MS (MH$^+$=451). Anal. calcd for C$_{20}$H$_{14}$ClF$_3$N$_4$O$_3$: C, 53.29% H, 3.13% N, 12.43%. Found: C, 53.33% H, 3.21% N, 12.60%.

Example B

N-[4-chloro-3-(trifluoromethyl)phenyl]-N'-{4-[2-N-methylcarbamoyl-4-pyridyloxy]phenyl}urea

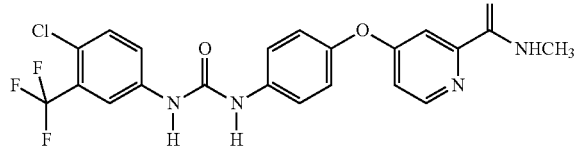

Step 1: 4-Chloro-N-methyl-2-pyridinecarboxamide is first synthesized from 4-chloropyridine-2-carbonyl chloride by adding 4-chloropyridine-2-carbonyl chloride HCl salt (7.0 g, 32.95 mmol) in portions to a mixture of a 2.0 M methylamine solution in THF (100 mL) and MeOH (20 mL) at 0° C. The resulting mixture is stored at 3° C. for 4 h, then concentrated under reduced pressure. The resulting nearly dry solids are suspended in EtOAc (100 mL) and filtered. The filtrate is washed with a saturated NaCl solution (2×100 mL), dried (Na$_2$SO$_4$) and concentrated under reduced pressure to provide 4-chloro-N-methyl-2-pyridinecarboxamide as a yellow, crystalline solid.

Step 2: A solution of 4-aminophenol (9.60 g, 88.0 mmol) in anh. DMF (150 mL) is treated with potassium tert-butoxide (10.29 g, 91.7 mmol), and the reddish-brown mixture is stirred at room temp. for 2 h. The contents are treated with 4-chloro-N-methyl-2-pyridinecarboxamide (15.0 g, 87.9 mmol) from Step 1 and K$_2$CO$_3$ (6.50 g, 47.0 mmol) and then heated at 80° C. for 8 h. The mixture is cooled to room temp. and separated between EtOAc (500 mL) and a saturated NaCl solution (500 mL). The aqueous phase is back-extracted with EtOAc (300 mL). The combined organic layers are washed with a saturated NaCl solution (4×1000 mL), dried (Na$_2$SO$_4$) and concentrated under reduced pressure. The resulting solids are dried under reduced pressure at 35° C. for 3 h to afford 4-(2-(N-methylcarbamoyl)-4-pyridyloxy)aniline as a light-brown solid. $^1$H-NMR (DMSO-d$_6$) δ 2.77 (d, J=4.8 Hz, 3H), 5.17 (br s, 2H), 6.64, 6.86 (AA'BB' quartet, J=8.4 Hz, 4H), 7.06 (dd, J=5.5, 2.5 Hz, 1H), 7.33 (d, J=2.5 Hz, 1H), 8.44 (d, J=5.5 Hz, 1H), 8.73 (br d, 1H); HPLC ES-MS m/z 244 ((M+H)$^+$).

Step 3: A solution of 4-chloro-3-(trifluoromethyl)phenyl isocyanate (14.60 g, 65.90 mmol) in CH$_2$Cl$_2$ (35 mL) is added dropwise to a suspension of 4-(2-(N-methylcarbamoyl)-4-pyridyloxy)aniline from Step 2; (16.0 g, 65.77 mmol) in CH$_2$Cl$_2$ (35 mL) at 0° C. The resulting mixture is stirred at room temp. for 22 h. The resulting yellow solids are removed by filtration, then washed with CH$_2$Cl$_2$ (2×30 mL) and dried under reduced pressure (approximately 1 mmHg) to afford N-(4-chloro-3-(trifluoromethyl)phenyl)-N'-(4-(2-(N-methylcarbamoyl)-4-pyridyloxy)phenyl)urea as an off-white solid: mp 207-209° C.; $^1$H-NMR (DMSO-d$_6$) δ 2.77 (d, J=4.8 Hz, 3H), 7.16 (m, 3H), 7.37 (d, J=2.5 Hz, 1H), 7.62 (m, 4H), 8.11 (d, J=2.5 Hz, 1H), 8.49 (d, J=5.5 Hz, 1H), 8.77 (br d, 1H), 8.99 (s, 1H), 9.21 (s, 1H); HPLC ES-MS m/z 465 ((M+H)$^+$).

Example C

N-[2-methoxy-5-(trifluoromethyl)phenyl]-N'-{4-[(2-N-methylcarbamoyl-4-pyridyloxy]phenyl}urea

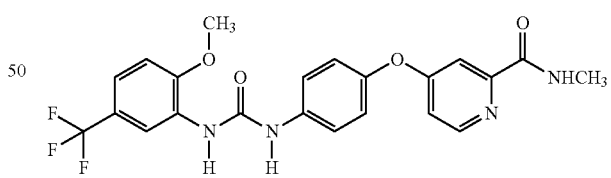

Step 1: 4-Chloro-N-methyl-2-pyridinecarboxamide is first synthesized from 4-chloropyridine-2-carbonyl chloride by adding 4-chloropyridine-2-carbonyl chloride HCl salt (7.0 g, 32.95 mmol) in portions to a mixture of a 2.0 M methylamine solution in THF (100 mL) and MeOH (20 mL) at 0° C. The resulting mixture is stored at 3° C. for 4 h, then concentrated under reduced pressure. The resulting nearly dry solids are suspended in EtOAc (100 mL) and filtered. The filtrate is washed with a saturated NaCl solution (2×100 mL), dried (Na$_2$SO$_4$) and concentrated under reduced pressure to provide 4-chloro-N-methyl-2-pyridinecarboxamide as a yellow, crystalline solid.

Step 2: A solution of 4-aminophenol (9.60 g, 88.0 mmol) in anh. DMF (150 mL) is treated with potassium tert-butoxide (10.29 g, 91.7 mmol), and the reddish-brown mixture is stirred at room temp. for 2 h. The contents are treated with 4-chloro-N-methyl-2-pyridinecarboxamide (15.0 g, 87.9 mmol) from Step 1 and $K_2CO_3$ (6.50 g, 47.0 mmol) and then heated at 80° C. for 8 h. The mixture is cooled to room temp. and separated between EtOAc (500 mL) and a saturated NaCl solution (500 mL). The aqueous phase is back-extracted with EtOAc (300 mL). The combined organic layers are washed with a saturated NaCl solution (4×1000 mL), dried ($Na_2SO_4$) and concentrated under reduced pressure. The resulting solids are dried under reduced pressure at 35° C. for 3 h to afford 4-(2-(N-methylcarbamoyl)-4-pyridyloxy)aniline as a light-brown solid. $^1$H-NMR (DMSO-$d_6$) δ 2.77 (d, J=4.8 Hz, 3H), 5.17 (br s, 2H), 6.64, 6.86 (AA'BB' quartet, J=8.4 Hz, 4H), 7.06 (dd, 2.5 Hz, 1H), 7.33 (d, J=2.5 Hz, 1H), 8.44 (d, J=5.5 Hz, 1H), 8.73 (br d, 1H); HPLC ES-MS m/z 244 ((M+H)$^+$).

Step 3: To a solution of 2-methoxy-5-(trifluoromethyl)aniline (0.15 g) in anh $CH_2Cl_2$ (15 mL) at 0° C. is added CDI (0.13 g). The resulting solution is allowed to warm to room temp. over 1 h, is stirred at room temp. for 16 h, then is treated with 4-(2-(N-methylcarbamoyl)-4-pyridyloxy)aniline (0.18 g) from Step 2. The resulting yellow solution is stirred at room temp. for 72 h, then is treated with $H_2O$ (125 mL). The resulting aqueous mixture is extracted with EtOAc (2×150 mL). The combined organics are washed with a saturated NaCl solution (100 mL), dried ($MgSO_4$) and concentrated under reduced pressure. The residue is triturated (90% EtOAc/10% hexane). The resulting white solids are collected by filtration and washed with EtOAc. The filtrate is concentrated under reduced pressure and the residual oil purified by column chromatography (gradient from 33% EtOAc/67% hexane to 50% EtOAc/50% hexane to 100% EtOAc) to give N-(2-methoxy-5-(trifluoromethyl)phenyl)-N'-(4-(2-(N-methylcarbamoyl)-4-pyridyloxy)phenyl)urea as a light tan solid: TLC (100% EtOAc) $R_f$ 0.62; $^1$H NMR (DMSO-$d_6$) δ 2.76 (d, J=4.8 Hz, 3H), 3.96 (s, 3H), 7.1-7.6 and 8.4-8.6 (m, 11H), 8.75 (d, J=4.8 Hz, 1H), 9.55 (s, 1H); FAB-MS m/z 461 ((M+H)$^+$).

Biological Examples

KDR (VEGFR2) Assay

The cytosolic kinase domain of KDR kinase was expressed as a 6H is fusion protein in Sf9 insect cells. The KDR kinase domain fusion protein was purified over a Ni++ chelating column. Ninety-six well ELISA plates Were coated with 5 μl HEPES buffer (20 mM poly(Glu4; Tyr1) (Sigma Chemical Co., St. Louis, Mo.) in 100 μk HEPES buffer (20 mM HEPES, pH 7.5, 150 mM Na Cl, 0.02% Thimerosal) at 4° overnight. Before use, the plate was washed with HEPES, NaCl buffer and the plates were blocked with 1% BSA, 0.1% Tween 20 in HEPES, NaCl buffer.

Test compounds were serially diluted in 100% DMSO form 4 mM to 0.12 μM in half-log dilutions. These dilutions were further diluted twenty fold in $H_2O$ to obtain compound solutions in 5% DMSO. Following loading of the assay plate with 85 μl of assay buffer (20 mM HEPES, pH 7.5, 100 mM KCl, 10 mM $MgCl_2$, 3 mM $MnCl_2$, 0.05% glycerol, 0.005% Triton X-100, 1 mM-mercaptoethanol, with or without 3.3 μM ATP), 5 μl of the diluted compounds were added to a final assay volume of 100 μl. Final concentrations were between 10 μM, and 0.3 mM in 0.25% DMSO. The assay was initiated by the addition of 10 μl (30 ng) of KDR kinase domain.

The assay was incubated with test compound or vehicle alone with gentle agitation at room temperature for 60 minutes. The wells were washed and phosphotyrosines (PY) were probed with an anti-phosphotyrosine (PY), mAb clone 4G10 (Upstate Biotechnology, Lake Placid, N.Y.). PY/anti-PY complexes were detected with an anti-mouse IgG/HRP conjugate Iamersham International plc, Buckinghamshire, England). Phosphotyrosine was quantitated by incubating with 100 μl 3,3',5,5' tetramethylbenzidine solution (Kirkegaard and Perry, TMB Microwell 1 Component peroxidase substrate). Color development was arrested by the addition of 100 μl % HCl-based stop solution (Kirkegaard and Perry, TMB 1 Component Stop Solution).

Optical densities were determined spectrophotometrically at 450 nm in a 96-well plate reader, SpectraMax 250 (Molecular Devices). Background (no ATP in assay) OD values were subtracted from all Ods and the percent inhibition was calculated according to the equation:

$$\% \text{ Inhibition} = \frac{(OD(\text{vehicle control}) - OD \text{ (with compound)}) \times 100}{OD \text{ (vehicle control)} - OD \text{ (no } ATP \text{ added)}}$$

The $IC_{50}$ values were determined with a least squares analysis program using compound concentration versus percent inhibition.

The following compounds were tested in the assay described above and were found to have either an $IC_{50}$ of less than 10 micromolar or showed greater than 30% inhibition at 1 micromolar. Compound names were generated using Nomenclator™ v 3.0 and may differ from those in the patent applications.

From WO 1999/32463:

| Entry No | Name |
| --- | --- |
| 73 | N-[5-(tert-butyl)-2-(3-thienyl)phenyl][(4-(4-pyridyloxy)phenyl)amino]carboxamide |
| 96 | {[4-(4-methoxyphenoxy)phenyl]amino}-N-[2-methoxy-5-(trifluoromethyl)phenyl]carboxamide |
| 99 | N-[2-methoxy-5-(trifluoromethyl)phenyl][(3-(4-pyridylthio)phenyl)amino]carboxamide |
| 100 | N-[2-methoxy-5-(trifluoromethyl)phenyl][(3-(4-pyridylthio)phenyl)amino]carboxamide |
| 101 | N-[2-methoxy-5-(trifluoromethyl)phenyl][(4-(4-pyridyloxy)phenyl)amino]carboxamide |

From WO 1999/32436:

| Entry No | Name |
| --- | --- |
| 11 | N-[5-(tert-butyl)-2-methoxyphenyl][(3-(4-pyridylthio)phenyl)amino]carboxamide |
| 12 | N-[5-(tert-butyl)-2-(3-thienyl)phenyl][(4-(4-pyridyloxy)phenyl)amino]carboxamide |
| 17 | N-[3-(tert-butyl)phenyl][(4-(4-pyridyloxy)phenyl)amino]carboxamide |
| 23 | {[3-(tert-butyl)phenyl]amino}-N-(4-(3-pyridyl)phenyl)carboxamide |
| 33 | {[4-(4-methoxyphenoxy)phenyl]amino}-N-[2-methoxy-5-(trifluoromethyl)phenyl]carboxamide |
| 36 | N-[2-methoxy-5-(trifluoromethyl)phenyl][(3-(4-pyridyloxy)phenyl)amino]carboxamide |
| 37 | N-[2-methoxy-5-(trifluoromethyl)phenyl][(3-(4-pyridylthio)phenyl)amino]carboxamide |
| 38 | N-[2-methoxy-5-(trifluoromethyl)phenyl][(4-(4-pyridyloxy)phenyl)amino]carboxamide |

| Entry No | Name |
|---|---|
| 56 | N-[2-methoxy-5-(trifluoromethyl)phenyl]{[3-(2-methyl(4-pyridyloxy))phenyl]amino}carboxamide |
| 70 | [(3-chloro-4-(6-quinolyloxy)phenyl)amino]-N-[2-methoxy-5-(trifluoromethyl)phenyl]carboxamide |
| 81 | [(4-(4-pyridyloxy)phenyl)amino]-N-[3-(trifluoromethyl)phenyl]carboxamide |
| 82 | N-[2-chloro-5-(trifluoromethyl)phenyl][(4-(4-pyridyloxy)phenyl)amino]carboxamide |
| 83 | N-[2-fluoro-5-(trifluoromethyl)phenyl][(4-(4-pyridyloxy)phenyl)amino]carboxamide |
| 91 | {[4-chloro-3-(trifluoromethyl)phenyl]amino}-N-(2-methyl-4-(3-pyridyloxy)phenyl)carboxamide |
| 102 | N-[4-chloro-3-(trifluoromethyl)phenyl][(4-(4-pyridyloxy)phenyl)amino]carboxamide |
| 103 | N-[4-chloro-3-(trifluoromethyl)phenyl]{[4-(4-methoxyphenoxy)phenyl]amino}carboxamide |
| 105 | {[4-chloro-3-(trifluoromethyl)phenyl]amino}-N-[3-(4-pyridylcarbonyl)phenyl]carboxamide |
| 106 | {[4-chloro-3-(trifluoromethyl)phenyl]amino}-N-[3-(2-methyl(4-pyridyloxy))phenyl]carboxamide |
| 119 | N-[4-fluoro-3-(trifluoromethyl)phenyl][(4-(4-pyridyloxy)phenyl)amino]carboxamide |
| 132 | N-[4-chloro-2-methoxy-5-(trifluoromethyl)phenyl][(4-(4-pyridyloxy)phenyl)amino]carboxamide |
| 133 | N-[5-methoxy-3-(trifluoromethyl)phenyl][(4-(4-pyridyloxy)phenyl)amino]carboxamide |
| 135 | [(3-bromo-4-chlorophenyl)amino]-N-(4-(4-pyridyloxy)phenyl)carboxamide |
| 136 | [(4-(4-pyridyloxy)phenyl)amino]-N-[3-(trifluoromethoxy)phenyl]carboxamide |
| 141 | N-[3,5-bis(trifluoromethyl)phenyl][(4-(4-pyridyloxy)phenyl)amino]carboxamide |

From WO 1999/32111:

| Entry No | Name |
|---|---|
| 18 | N-[5-(tert-butyl)isoxazol-3-yl][(4-(4-pyridylthio)phenyl)amino]carboxamide |
| 32 | {[5-(tert-butyl)isoxazol-3-yl]amino}-N-(3-(4-pyridylthio)phenyl)carboxamide |
| 53 | N-[5-(tert-butyl)isoxazol-3-yl][(4-(4-pyridyloxy)phenyl)amino]carboxamide |
| 59 | N-[5-(tert-butyl)isoxazol-3-yl][(4-(3-pyridyloxy)phenyl)amino]carboxamide |
| 67 | {3-[4-({[5-(tert-butyl)isoxazol-3-yl]amino}carbonylamino)phenoxy]phenyl}-N-methylcarboxamide |
| 85 | {[5-(tert-butyl)isoxazol-3-yl]amino}-N-[3-(2-methyl(4-pyridyloxy))phenyl]carboxamide |
| 86 | N-[5-(tert-butyl)isoxazol-3-yl]{[4-(2-methyl(4-pyridyloxy))phenyl]amino}carboxamide |
| 103 | 4-[4-({[5-(tert-butyl)isoxazol-3-yl]amino}carbonylamino)phenoxy]pyridine-2-carboxamide |
| 104 | {[5-(tert-butyl)isoxazol-3-yl]amino}-N-{3-[2-(N-methylcarbamoyl)(4-pyridyloxy)]phenyl}carboxamide |
| 105 | 4-[3-({N-[5-(tert-butyl)isoxazol-3-yl]carbamoyl}amino)phenoxy]pyridine-2-carboxamide |
| 106 | 3-[4-({[5-(tert-butyl)isoxazol-3-yl]amino}carbonylamino)phenoxy]benzamide |
| 143 | N-[3-(methylethyl)isoxazol-5-yl][(4-(4-pyridyloxy)phenyl)amino]carboxamide |
| 146 | N-(3-cyclobutylisoxazol-5-yl)[(4-(4-pyridyloxy)phenyl)amino]carboxamide |
| 147 | N-(3-cyclobutylisoxazol-5-yl)[(4-(6-quinolyloxy)phenyl)amino]carboxamide |
| 162 | {[3-(tert-butyl)isoxazol-5-yl]amino}-N-(3-(4-pyridylthio)phenyl)carboxamide |
| 163 | N-[3-(tert-butyl)isoxazol-5-yl][(4-(4-pyridyloxy)phenyl)amino]carboxamide |
| 164 | N-[3-(tert-butyl)isoxazol-5-yl]{[4-(4-methoxyphenoxy)phenyl]amino}carboxamide |
| 188 | N-[3-(1,1-dimethylpropyl)isoxazol-5-yl][(3-(4-pyridylthio)phenyl)amino]carboxamide |
| 195 | N-[3-(1,1-dimethylpropyl)isoxazol-5-yl][(4-(4-pyridyloxy)phenyl)amino]carboxamide |
| 220 | {[3-(tert-butyl)pyrazol-5-yl]amino}-N-(3-(4-pyridylthio)phenyl)carboxamide |
| 221 | N-[3-(tert-butyl)pyrazol-5-yl][(4-(4-pyridylthio)phenyl)amino]carboxamide |
| 222 | {3-[4-({[3-(tert-butyl)pyrazol-5-yl]amino}carbonylamino)phenoxy]phenyl}-N-methylcarboxamide,2,2,2-trifluoroacetic acid |

-continued

| Entry No | Name |
|---|---|
| 225 | N-[3-(tert-butyl)-1-methylpyrazol-5-yl][(3-(4-pyridylthio)phenyl)amino]carboxamide |
| 251 | N-[3-(tert-butyl)-1-methylpyrazol-5-yl][(4-(4-pyridyloxy)phenyl)amino]carboxamide |
| 261 | N-[3-(tert-butyl)-1-methylpyrazol-5-yl]{[4-(4-pyridylmethyl)phenyl]amino}carboxamide |
| 266 | N-[3-(tert-butyl)-1-methylpyrazol-5-yl]{[4-(4-pyridylmethoxy)phenyl]amino}carboxamide |
| 277 | tert-butyl 3-(tert-butyl)-5-[({4-[3-(N-methylcarbamoyl)phenoxy]phenyl}amino)carbonylamino]pyrazolecarboxylate |
| 280 | N-[5-(tert-butyl)(1,3,4-thiadiazol-2-yl)][(4-(4-pyridyloxy)phenyl)amino]carboxamide |
| 281 | {[5-(tert-butyl)(1,3,4-thiadiazol-2-yl)]amino}-N-(3-(4-pyridylthio)phenyl)carboxamide |
| 284 | N-[5-(tert-butyl)(3-thienyl)][(4-(3-pyridyloxy)phenyl)amino]carboxamide |
| 293 | N-[5-(tert-butyl)(3-thienyl)][(4-(4-pyridyloxy)phenyl)amino]carboxamide |
| 299 | N-(6-chloro(1H-indazol-3-yl))[(4-(4-pyridyloxy)phenyl)amino]carboxamide |
| 302 | ({4-[2-(N-methylcarbamoyl)(4-pyridyloxy)]phenyl}amino)-N-(1-methyl-3-phenylpyrazol-5-yl)carboxamide |

From WO 1999/

| Entry No | Name |
|---|---|
| 21 | N-[5-(tert-butyl)isoxazol-3-yl][(4-(4-pyridylthio)phenyl)amino]carboxamide |
| 42 | {[5-(tert-butyl)isoxazol-3-yl]amino}-N-(3-(4-pyridylthio)phenyl)carboxamide |
| 59 | N-[5-(tert-butyl)isoxazol-3-yl][(4-(4-pyridyloxy)phenyl)amino]carboxamide |
| 64 | N-[5-(tert-butyl)isoxazol-3-yl][(4-(3-pyridyloxy)phenyl)amino]carboxamide |
| 69 | {3-[4-({[5-(tert-butyl)isoxazol-3-yl]amino}carbonylamino)phenoxy]phenyl}-N-methylcarboxamide |
| 81 | {[5-(tert-butyl)isoxazol-3-yl]amino}-N-[3-(2-methyl(4-pyridyloxy))phenyl]carboxamide |
| 82 | N-[5-(tert-butyl)isoxazol-3-yl]{[4-(2-methyl(4-pyridyloxy))phenyl]amino}carboxamide |
| 101 | {4-[4-({[5-(tert-butyl)isoxazol-3-yl]amino}carbonylamino)phenoxy](2-pyridyl)}-N-methylcarboxamide |
| 103 | 4-[4-({[5-(tert-butyl)isoxazol-3-yl]amino}carbonylamino)phenoxy]pyridine-2-carboxamide |
| 104 | 4-[3-({N-[5-(tert-butyl)isoxazol-3-yl]carbamoyl}amino)phenoxy]pyridine-2-carboxamide |
| 105 | {[5-(tert-butyl)isoxazol-3-yl]amino}-N-{3-[2-(N-methylcarbamoyl)(4-pyridyloxy)]phenyl}carboxamide |
| 106 | 3-[4-({[5-(tert-butyl)isoxazol-3-yl]amino}carbonylamino)phenoxy]benzamide |
| 118 | {4-[4-({[5-(tert-butyl)isoxazol-3-yl]amino}carbonylamino)-3-chlorophenoxy](2-pyridyl)}-N-methylcarboxamide |
| 124 | {3-[4-({[5-(tert-butyl)isoxazol-3-yl]amino}carbonylamino)phenoxy]phenyl}-N-(2-morpholin-4-ylethyl)carboxamide |
| 125 | {4-[4-({[5-(tert-butyl)isoxazol-3-yl]amino}carbonylamino)phenoxy](2-pyridyl)}-N-ethylcarboxamide |
| 126 | {4-[4-({[5-(tert-butyl)isoxazol-3-yl]amino}carbonylamino)-2-chlorophenoxy](2-pyridyl)}-N-methylcarboxamide |
| 127 | {[5-(tert-butyl)isoxazol-3-yl]amino}-N-{2-methyl-4-[2-(N-methylcarbamoyl)(4-pyridyloxy)]phenyl}carboxamide |
| 128 | {[5-(tert-butyl)isoxazol-3-yl]amino}-N-{3-[2-(N-methylcarbamoyl)(4-pyridylthio)]phenyl}carboxamide |
| 130 | {3-[4-({[5-(tert-butyl)isoxazol-3-yl]amino}carbonylamino)phenoxy]phenyl}-N-(3-pyridyl)carboxamide |
| 140 | {4-[4-({[5-(tert-butyl)isoxazol-3-yl]amino}carbonylamino)phenylthio](2-pyridyl)}-N-methylcarboxamide |

-continued

| Entry No | Name |
|---|---|
| 182 | N-methyl{4-[4-({[3-(methylethyl)isoxazol-5-yl]amino}carbonylamino)phenoxy](2-pyridyl)}carboxamide |
| 186 | N-methyl{4-[3-({[3-(methylethyl)isoxazol-5-yl]amino}carbonylamino)phenoxy](2-pyridyl)}carboxamide |
| 187 | N-(3-cyclobutylisoxazol-5-yl)[(4-(6-quinolyloxy)phenyl)amino]carboxamide |
| 188 | N-(3-cyclobutylisoxazol-5-yl)[(4-(4-pyridyloxy)phenyl)amino]carboxamide |
| 194 | N-[3-(tert-butyl)isoxazol-5-yl][(4-(4-pyridyloxy)phenyl)amino]carboxamide |
| 195 | N-[3-(tert-butyl)isoxazol-5-yl]{[4-(4-methoxyphenoxy)phenyl]amino}carboxamide |
| 206 | {[3-(tert-butyl)isoxazol-5-yl]amino}-N-(3-(4-pyridylthio)phenyl)carboxamide |
| 212 | N-[3-(tert-butyl)isoxazol-5-yl]{[4-(1,3-dioxoisoindolin-5-yloxy)phenyl]amino}carboxamide |
| 213 | {[3-(tert-butyl)isoxazol-5-yl]amino}-N-[4-(1-oxoisoindolin-5-yloxy)phenyl]carboxamide |
| 214 | {4-[4-({[3-(tert-butyl)isoxazol-5-yl]amino}carbonylamino)phenoxy](2-pyridyl)}-N-ethylcarboxamide |
| 215 | {4-[4-({[3-(tert-butyl)isoxazol-5-yl]amino}carbonylamino)-2-chlorophenoxy](2-pyridyl)}-N-methylcarboxamide |
| 216 | {[3-(tert-butyl)isoxazol-5-yl]amino}-N-{3-[2-(N-methylcarbamoyl)(4-pyridylthio)]phenyl}carboxamide |
| 217 | {4-[4-({[3-(tert-butyl)isoxazol-5-yl]amino}carbonylamino)phenylthio](2-pyridyl)}-N-methylcarboxamide |
| 218 | {4-[4-({[3-(tert-butyl)isoxazol-5-yl]amino}carbonylamino)phenoxy](2-pyridyl)}-N-methylcarboxamide |
| 228 | {[3-(tert-butyl)isoxazol-5-yl]amino}-N-[3-(6-methyl(3-pyridyloxy))phenyl]carboxamide |
| 240 | N-[3-(tert-butyl)isoxazol-5-yl][(6-(4-pyridylthio)(3-pyridyl))amino]carboxamide |
| 247 | {[3-(tert-butyl)isoxazol-5-yl]amino}-N-{3-[2-(N-methylcarbamoyl)(4-pyridyloxy)]phenyl}carboxamide |
| 253 | N-[3-(1,1-dimethylpropyl)isoxazol-5-yl][(3-(4-pyridylthio)phenyl)amino]carboxamide |
| 255 | N-[3-(1,1-dimethylpropyl)isoxazol-5-yl][(4-(4-pyridyloxy)phenyl)amino]carboxamide |
| 261 | N-[3-(1,1-dimethylpropyl)isoxazol-5-yl]({4-[2-(N-methylcarbamoyl)(4-pyridyloxy)]phenyl}amino)carboxamide |
| 263 | N-[3-(1,1-dimethylpropyl)isoxazol-5-yl]{[4-(2-methyl(4-pyridylthio))phenyl]amino}carboxamide |
| 292 | N-[3-(tert-butyl)pyrazol-5-yl]{[4-(6-methyl(3-pyridyloxy))phenyl]amino}carboxamide |
| 298 | {[3-(tert-butyl)pyrazol-5-yl]amino}-N-(3-(4-pyridylthio)phenyl)carboxamide |
| 299 | N-[3-(tert-butyl)pyrazol-5-yl][(4-(4-pyridylthio)phenyl)amino]carboxamide |
| 300 | {3-[4-({[3-(tert-butyl)pyrazol-5-yl]amino}carbonylamino)phenoxy]phenyl}-N-methylcarboxamide, 2,2,2-trifluoroacetic acid |
| 304 | N-[3-(tert-butyl)-1-methylpyrazol-5-yl]{[4-(4-pyridylmethoxy)phenyl]amino}carboxamide |
| 305 | {5-[4-({[3-(tert-butyl)-1-methylpyrazol-5-yl]amino}carbonylamino)phenoxy]-2-methoxyphenyl}-N-methylcarboxamide |
| 309 | N-[3-(tert-butyl)-1-methylpyrazol-5-yl][(3-(4-pyridylthio)phenyl)amino]carboxamide |
| 321 | N-[3-(tert-butyl)-1-methylpyrazol-5-yl][(4-(4-pyridyloxy)phenyl)amino]carboxamide |
| 326 | N-[3-(tert-butyl)-1-methylpyrazol-5-yl]{[4-(4-pyridylmethyl)phenyl]amino}carboxamide |
| 339 | tert-butyl 3-(tert-butyl)-5-[({4-[3-(N-methylcarbamoyl)phenoxy]phenyl}amino)carbonylamino]pyrazolecarboxylate |
| 341 | N-[5-(tert-butyl)(1,3,4-thiadiazol-2-yl)][(4-(4-pyridyloxy)phenyl)amino]carboxamide |
| 342 | {[5-(tert-butyl)(1,3,4-thiadiazol-2-yl)]amino}-N-(3-(4-pyridylthio)phenyl)carboxamide |
| 356 | N-[5-(tert-butyl)(1,3,4-thiadiazol-2-yl)]{[6-(6-methyl(3-pyridyloxy))(3-pyridyl)]amino}carboxamide |
| 366 | N-[5-(1,1-dimethylpropyl)(1,3,4-thiadiazol-2-yl)][(4-(4-pyridyloxy)phenyl)amino]carboxamide |
| 367 | N-[5-(1,1-dimethylpropyl)(1,3,4-thiadiazol-2-yl)][(3-(4-pyridylthio)phenyl)amino]carboxamide |

| Entry No | Name |
|---|---|
| 376 | N-[5-(tert-butyl)(3-thienyl)][(4-(3-pyridyloxy)phenyl)amino]carboxamide |
| 388 | {3-[4-({[5-(tert-butyl)(1,3,4-oxadiazol-2-yl)]amino}carbonylamino)phenoxy]phenyl}-N-ethylcarboxamide |
| 389 | {3-[4-({[5-(tert-butyl)(1,3,4-oxadiazol-2-yl)]amino}carbonylamino)phenoxy]phenyl}-N-(methylethyl)carboxamide |
| 390 | {3-[4-({[5-(tert-butyl)(1,3,4-oxadiazol-2-yl)]amino}carbonylamino)phenoxy]phenyl}-N-methylcarboxamide |
| 391 | N-[5-(tert-butyl)(1,3,4-oxadiazol-2-yl)][(4-(4-pyridyloxy)phenyl)amino]carboxamide |
| 392 | N-(3-cyclopropyl-1-methylpyrazol-5-yl)[(4-(6-quinolyloxy)phenyl)amino]carboxamide |
| 393 | ({4-[2-(N-methylcarbamoyl)(4-pyridyloxy)]phenyl}amino)-N-(1-methyl-3-phenylpyrazol-5-yl)carboxamide |
| 395 | N-[2-(tert-butyl)(1,3-thiazol-5-yl)]{[4-(6-methyl(3-pyridyloxy))phenyl]amino}carboxamide |

From WO 1999/32110

| Entry No | Name |
|---|---|
| 1 | [(2,3-dichlorophenyl)amino]-N-[3-(tert-butyl)-1-phenylpyrazol-5-yl]carboxamide |
| 2 | N-[1-(4-aminophenyl)-3-(tert-butyl)pyrazol-5-yl][(2,3-dichlorophenyl)amino]carboxamide |
| 11 | N-[1-(3-aminophenyl)-3-(tert-butyl)pyrazol-5-yl][(2,3-dichlorophenyl)amino]carboxamide |
| 18 | N-[3-(3-(tert-butyl)-5-{[(4-phenoxyphenyl)amino]carbonylamino}pyrazolyl)phenyl]acetamide |
| 23 | N-[1-(2,6-dichlorophenyl)-3-(tert-butyl)pyrazol-5-yl]{[4-(4-pyridylmethyl)phenyl]amino}carboxamide |
| 24 | N-[3-(tert-butyl)-1-(4-fluorophenyl)pyrazol-5-yl]{[4-(4-pyridylmethyl)phenyl]amino}carboxamide |
| 25 | N-[3-(tert-butyl)-1-(2-methylphenyl)pyrazol-5-yl]{[4-(4-pyridylmethyl)phenyl]amino}carboxamide |
| 26 | N-[3-(tert-butyl)-1-(3-fluorophenyl)pyrazol-5-yl]{[4-(4-pyridylmethyl)phenyl]amino}carboxamide |
| 27 | N-{3-(tert-butyl)-1-[4-(methylsulfonyl)phenyl]pyrazol-5-yl}{[4-(4-pyridylmethyl)phenyl]amino}carboxamide |
| 28 | N-[3-(tert-butyl)-1-(4-nitrophenyl)pyrazol-5-yl]{[4-(4-pyridylmethyl)phenyl]amino}carboxamide |
| 29 | N-[3-(tert-butyl)-1-(3-methoxyphenyl)pyrazol-5-yl]{[4-(4-pyridylmethyl)phenyl]amino}carboxamide |
| 30 | N-[1-(3-aminophenyl)-3-(tert-butyl)pyrazol-5-yl]{[4-(4-pyridylmethyl)phenyl]amino}carboxamide |
| 32 | N-[1-(3-aminophenyl)-3-(tert-butyl)pyrazol-5-yl][(4-(4-pyridylthio)phenyl)amino]carboxamide |
| 34 | N-[3-(tert-butyl)-1-(3-fluorophenyl)pyrazol-5-yl][(3-(4-pyridylthio)phenyl)amino]carboxamide |
| 35 | N-[3-(tert-butyl)-1-(4-fluorophenyl)pyrazol-5-yl][(3-(4-pyridylthio)phenyl)amino]carboxamide |
| 36 | N-[3-(tert-butyl)-1-(3-fluorophenyl)pyrazol-5-yl][(4-(4-pyridyloxy)phenyl)amino]carboxamide |
| 37 | N-[3-(tert-butyl)-1-(4-fluorophenyl)pyrazol-5-yl][(4-(4-pyridyloxy)phenyl)amino]carboxamide |

From WO 1999/32455

| Entry No | Name |
|---|---|
| 1 | [(2,3-dichlorophenyl)amino]-N-[3-(tert-butyl)-1-phenylpyrazol-5-yl]carboxamide |
| 2 | N-[1-(4-aminophenyl)-3-(tert-butyl)pyrazol-5-yl][(2,3-dichlorophenyl)amino]carboxamide |
| 14 | N-[1-(3-aminophenyl)-3-(tert-butyl)pyrazol-5-yl][(2,3-dichlorophenyl)amino]carboxamide |
| 22 | N-[3-(3-(tert-butyl)-5-{[(4-phenoxyphenyl)amino]carbonylamino}pyrazolyl)phenyl]acetamide |
| 27 | N-[1-(2,6-dichlorophenyl)-3-(tert-butyl)pyrazol-5-yl]{[4-(4-pyridylmethyl)phenyl]amino}carboxamide |
| 28 | N-[3-(tert-butyl)-1-(4-fluorophenyl)pyrazol-5-yl]{[4-(4-pyridylmethyl)phenyl]amino}carboxamide |
| 29 | N-[3-(tert-butyl)-1-(2-methylphenyl)pyrazol-5-yl]{[4-(4-pyridylmethyl)phenyl]amino}carboxamide |
| 30 | N-[3-(tert-butyl)-1-(3-fluorophenyl)pyrazol-5-yl]{[4-(4-pyridylmethyl)phenyl]amino}carboxamide |
| 31 | N-{3-(tert-butyl)-1-[4-(methylsulfonyl)phenyl]pyrazol-5-yl}{[4-(4-pyridylmethyl)phenyl]amino}carboxamide |
| 32 | N-[3-(tert-butyl)-1-(4-nitrophenyl)pyrazol-5-yl]{[4-(4-pyridylmethyl)phenyl]amino}carboxamide |
| 33 | N-[3-(tert-butyl)-1-(3-methoxyphenyl)pyrazol-5-yl]{[4-(4-pyridylmethyl)phenyl]amino}carboxamide |
| 34 | N-[1-(3-aminophenyl)-3-(tert-butyl)pyrazol-5-yl]{[4-(4-pyridylmethyl)phenyl]amino}carboxamide |
| 36 | N-[1-(3-aminophenyl)-3-(tert-butyl)pyrazol-5-yl][(4-(4-pyridylthio)phenyl)amino]carboxamide |

From WO 2000/41698

| Entry No | Name |
|---|---|
| 1 | {3-[4-({[3-(tert-butyl)phenyl]amino}carbonylamino)phenoxy]phenyl}-N-methylcarboxamide |
| 11 | N-[2-methoxy-5-(trifluoromethyl)phenyl]({3-[2-(N-methylcarbamoyl)(4-pyridyloxy)]phenyl}amino)carboxamide |
| 12 | 4-[3-({N-[2-methoxy-5-(trifluoromethyl)phenyl]carbamoyl}amino)phenoxy]pyridine-2-carboxamide |
| 13 | N-[2-methoxy-5-(trifluoromethyl)phenyl]({4-[2-(N-methylcarbamoyl)(4-pyridyloxy)]phenyl}amino)carboxamide |
| 14 | 4-[4-({N-[2-methoxy-5-(trifluoromethyl)phenyl]carbamoyl}amino)phenoxy]pyridine-2-carboxamide |
| 16 | {4-[4-({N-[2-methoxy-5-(trifluoromethyl)phenyl]carbamoyl}amino)-3-methylphenoxy](2-pyridyl)}-N-methylcarboxamide |
| 17 | ({2-chloro-4-[2-(N-methylcarbamoyl)(4-pyridyloxy)]phenyl}amino)-N-[2-methoxy-5-(trifluoromethyl)phenyl]carboxamide |

-continued

| Entry No | Name |
|---|---|
| 19 | ({4-[2-(N-ethylcarbamoyl)(4-pyridyloxy)]phenyl}amino)-N-[2-methoxy-5-(trifluoromethyl)phenyl]carboxamide |
| 20 | ({3-chloro-4-[2-(N-methylcarbamoyl)(4-pyridyloxy)]phenyl}amino)-N-[2-methoxy-5-(trifluoromethyl)phenyl]carboxamide |
| 22 | 3-[4-({N-[2-methoxy-5-(trifluoromethyl)phenyl]carbamoyl}amino)phenoxy]benzamide |
| 24 | ({4-[2-(N,N-dimethylcarbamoyl)(4-pyridyloxy)]phenyl}amino)-N-[2-methoxy-5-(trifluoromethyl)phenyl]carboxamide |
| 27 | N-[2-methoxy-5-(trifluoromethyl)phenyl]({4-[2-(N-methylcarbamoyl)(4-pyridylthio)]phenyl}amino)carboxamide |
| 29 | N-[2-methoxy-5-(trifluoromethyl)phenyl]({3-[2-(N-methylcarbamoyl)(4-pyridylthio)]phenyl}amino)carboxamide |
| 31 | N-[2-methoxy-5-(trifluoromethyl)phenyl][(4-{5-[N-(2-morpholin-4-ylethyl)carbamoyl](3-pyridyloxy)}phenyl)amino]carboxamide |
| 32 | N-[2-methoxy-5-(trifluoromethyl)phenyl]({4-[5-(N-methylcarbamoyl)(3-pyridyloxy)]phenyl}amino)carboxamide |
| 34 | N-[2-methoxy-5-(trifluoromethyl)phenyl]({4-[3-(N-(3-pyridyl)carbamoyl)phenoxy]phenyl}amino)carboxamide |
| 42 | {4-[4-({[4-chloro-3-(trifluoromethyl)phenyl]amino}carbonylamino)phenoxy](2-pyridyl)}-N-methylcarboxamide |
| 43 | 4-[4-({[4-chloro-3-(trifluoromethyl)phenyl]amino}carbonylamino)phenoxy]pyridine-2-carboxamide |
| 44 | 4-[3-({[4-chloro-3-(trifluoromethyl)phenyl]amino}carbonylamino)phenoxy]pyridine-2-carboxamide |
| 45 | {[4-chloro-3-(trifluoromethyl)phenyl]amino}-N-{3-[2-(N-methylcarbamoyl)(4-pyridyloxy)]phenyl}carboxamide |
| 47 | {[4-chloro-3-(trifluoromethyl)phenyl]amino}-N-{2-methyl-4-[2-(N-methylcarbamoyl)(4-pyridyloxy)]phenyl}carboxamide |
| 49 | {4-[3-chloro-4-({[4-chloro-3-(trifluoromethyl)phenyl]amino}carbonylamino)phenoxy](2-pyridyl)}-N-methylcarboxamide |
| 51 | N-[4-chloro-3-(trifluoromethyl)phenyl]({4-[2-(N-ethylcarbamoyl)(4-pyridyloxy)]phenyl}amino)carboxamide |
| 61 | {3-[4-({[4-chloro-3-(trifluoromethyl)phenyl]amino}carbonylamino)phenoxy]phenyl}-N-(2-morpholin-4-ylethyl)carboxamide |
| 62 | {3-[4-({[4-chloro-3-(trifluoromethyl)phenyl]amino}carbonylamino)phenoxy]phenyl}-N-(2-piperidylethyl)carboxamide |
| 65 | {4-[4-({[4-chloro-3-(trifluoromethyl)phenyl]amino}carbonylamino)phenylthio](2-pyridyl)}-N-methylcarboxamide |
| 69 | {[4-chloro-3-(trifluoromethyl)phenyl]amino}-N-{3-[2-(N-methylcarbamoyl)(4-pyridylthio)]phenyl}carboxamide |
| 70 | {4-[4-({[4-chloro-3-(trifluoromethyl)phenyl]amino}carbonylamino)phenoxy](2-pyridyl)}-N-(2-morpholin-4-ylethyl)carboxamide |
| 72 | {5-[4-({[4-chloro-3-(trifluoromethyl)phenyl]amino}carbonylamino)phenoxy](3-pyridyl)}-N-methylcarboxamide |
| 75 | N-[4-chloro-3-(trifluoromethyl)phenyl]({4-[3-(N-(3-pyridyl)carbamoyl)phenoxy]phenyl}amino)carboxamide |
| 84 | {4-[4-({[4-chloro-3-(trifluoromethyl)phenyl]amino}carbonylamino)phenoxy](2-pyridyl)}-N-(2-hydroxyethyl)carboxamide |
| 87 | {4-[4-({[4-bromo-3-(trifluoromethyl)phenyl]amino}carbonylamino)-2-chlorophenoxy](2-pyridyl)}-N-methylcarboxamide |
| 88 | N-[4-bromo-3-(trifluoromethyl)phenyl]({4-[2-(N-ethylcarbamoyl)(4-pyridyloxy)]phenyl}amino)carboxamide |
| 89 | {[4-bromo-3-(trifluoromethyl)phenyl]amino}-N-{3-[2-(N-methylcarbamoyl)(4-pyridyloxy)]phenyl}carboxamide |
| 90 | {[4-bromo-3-(trifluoromethyl)phenyl]amino}-N-{4-methyl-3-[2-(N-methylcarbamoyl)(4-pyridyloxy)]phenyl}carboxamide |
| 93 | {[4-bromo-3-(trifluoromethyl)phenyl]amino}-N-{3-[2-(N-methylcarbamoyl)(4-pyridylthio)]phenyl}carboxamide |
| 94 | {4-[4-({[4-bromo-3-(trifluoromethyl)phenyl]amino}carbonylamino)phenoxy](2-pyridyl)}-N-(2-morpholin-4-ylethyl)carboxamide |
| 95 | N-[4-chloro-2-methoxy-5-(trifluoromethyl)phenyl]({4-[2-(N-methylcarbamoyl)(4-pyridyloxy)]phenyl}amino)carboxamide |
| 96 | N-[4-chloro-2-methoxy-5-(trifluoromethyl)phenyl]({2-chloro-4-[2-(N-methylcarbamoyl)(4-pyridyloxy)]phenyl}amino)carboxamide |
| 97 | N-[4-chloro-2-methoxy-5-(trifluoromethyl)phenyl]({3-chloro-4-[2-(N-methylcarbamoyl)(4-pyridyloxy)]phenyl}amino)carboxamide |
| 98 | N-[4-chloro-2-methoxy-5-(trifluoromethyl)phenyl]({3-[2-(N-methylcarbamoyl)(4-pyridyloxy)]phenyl}amino)carboxamide |
| 99 | N-[4-chloro-2-methoxy-5-(trifluoromethyl)phenyl]({4-[2-(N-ethylcarbamoyl)(4-pyridyloxy)]phenyl}amino)carboxamide |

From WO 2000/42012

| Entry No | Name |
|---|---|
| 1 | {3-[4-({[3-(tert-butyl)phenyl]amino}carbonylamino)phenoxy]phenyl}-N-methylcarboxamide |
| 11 | N-[2-methoxy-5-(trifluoromethyl)phenyl]({3-[2-(N-methylcarbamoyl)(4-pyridyloxy)]phenyl}amino)carboxamide |
| 12 | 4-[3-({N-[2-methoxy-5-(trifluoromethyl)phenyl]carbamoyl}amino)phenoxy]pyridine-2-carboxamide |
| 13 | N-[2-methoxy-5-(trifluoromethyl)phenyl]({4-[2-(N-methylcarbamoyl)(4-pyridyloxy)]phenyl}amino)carboxamide |
| 14 | 4-[4-({N-[2-methoxy-5-(trifluoromethyl)phenyl]carbamoyl}amino)phenoxy]pyridine-2-carboxamide |
| 16 | {4-[4-({N-[2-methoxy-5-(trifluoromethyl)phenyl]carbamoyl}amino)-3-methylphenoxy](2-pyridyl)}-N-methylcarboxamide |
| 17 | ({2-chloro-4-[2-(N-methylcarbamoyl)(4-pyridyloxy)]phenyl}amino)-N-[2-methoxy-5-(trifluoromethyl)phenyl]carboxamide |
| 19 | ({4-[2-(N-ethylcarbamoyl)(4-pyridyloxy)]phenyl}amino)-N-[2-methoxy-5-(trifluoromethyl)phenyl]carboxamide |
| 20 | ({3-chloro-4-[2-(N-methylcarbamoyl)(4-pyridyloxy)]phenyl}amino)-N-[2-methoxy-5-(trifluoromethyl)phenyl]carboxamide |
| 22 | 3-[4-({N-[2-methoxy-5-(trifluoromethyl)phenyl]carbamoyl}amino)phenoxy]benzamide |
| 24 | ({4-[2-(N,N-dimethylcarbamoyl)(4-pyridyloxy)]phenyl}amino)-N-[2-methoxy-5-(trifluoromethyl)phenyl]carboxamide |
| 27 | N-[2-methoxy-5-(trifluoromethyl)phenyl]({4-[2-(N-methylcarbamoyl)(4-pyridylthio)]phenyl}amino)carboxamide |
| 29 | N-[2-methoxy-5-(trifluoromethyl)phenyl]({3-[2-(N-methylcarbamoyl)(4-pyridylthio)]phenyl}amino)carboxamide |
| 31 | N-[2-methoxy-5-(trifluoromethyl)phenyl][(4-{5-[N-(2-morpholin-4-ylethyl)carbamoyl](3-pyridyloxy)}phenyl)amino]carboxamide |
| 32 | N-[2-methoxy-5-(trifluoromethyl)phenyl]({4-[5-(N-methylcarbamoyl)(3-pyridyloxy)]phenyl}amino)carboxamide |
| 34 | N-[2-methoxy-5-(trifluoromethyl)phenyl]({4-[3-(N-(3-pyridyl)carbamoyl)phenoxy]phenyl}amino)carboxamide |
| 42 | {4-[4-({[4-chloro-3-(trifluoromethyl)phenyl]amino}carbonylamino)phenoxy](2-pyridyl)}-N-methylcarboxamide |
| 43 | 4-[4-({[4-chloro-3-(trifluoromethyl)phenyl]amino}carbonylamino)phenoxy]pyridine-2-carboxamide |
| 44 | 4-[3-({[4-chloro-3-(trifluoromethyl)phenyl]amino}carbonylamino)phenoxy]pyridine-2-carboxamide |
| 45 | {[4-chloro-3-(trifluoromethyl)phenyl]amino}-N-{3-[2-(N-methylcarbamoyl)(4-pyridyloxy)]phenyl}carboxamide |
| 47 | {[4-chloro-3-(trifluoromethyl)phenyl]amino}-N-{2-methyl-4-[2-(N-methylcarbamoyl)(4-pyridyloxy)]phenyl}carboxamide |
| 49 | {4-[3-chloro-4-({[4-chloro-3-(trifluoromethyl)phenyl]amino}carbonylamino)phenoxy](2-pyridyl)}-N-methylcarboxamide |
| 51 | N-[4-chloro-3-(trifluoromethyl)phenyl]({4-[2-(N-ethylcarbamoyl)(4-pyridyloxy)]phenyl}amino)carboxamide |

-continued

| Entry No | Name |
|---|---|
| 61 | {3-[4-({[4-chloro-3-(trifluoromethyl)phenyl]amino}carbonylamino)phenoxy]phenyl}-N-(2-morpholin-4-ylethyl)carboxamide |
| 62 | {3-[4-({[4-chloro-3-(trifluoromethyl)phenyl]amino}carbonylamino)phenoxy]phenyl}-N-(2-piperidylethyl)carboxamide |
| 65 | {4-[4-({[4-chloro-3-(trifluoromethyl)phenyl]amino}carbonylamino)phenylthio](2-pyridyl)}-N-methylcarboxamide |
| 69 | {[4-chloro-3-(trifluoromethyl)phenyl]amino}-N-{3-[2-(N-methylcarbamoyl)(4-pyridylthio)]phenyl}carboxamide |
| 70 | {4-[4-({[4-chloro-3-(trifluoromethyl)phenyl]amino}carbonylamino)phenoxy](2-pyridyl)}-N-(2-morpholin-4-ylethyl)carboxamide |
| 72 | {5-[4-({[4-chloro-3-(trifluoromethyl)phenyl]amino}carbonylamino)phenoxy](3-pyridyl)}-N-methylcarboxamide |
| 75 | N-[4-chloro-3-(trifluoromethyl)phenyl]({4-[3-(N-(3-pyridyl)carbamoyl)phenoxy]phenyl}amino)carboxamide |
| 84 | {4-[4-({[4-chloro-3-(trifluoromethyl)phenyl]amino}carbonylamino)phenoxy](2-pyridyl)}-N-(2-hydroxyethyl)carboxamide |
| 87 | {4-[4-({[4-bromo-3-(trifluoromethyl)phenyl]amino}carbonylamino)-2-chlorophenoxy](2-pyridyl)}-N-methylcarboxamide |
| 88 | N-[4-bromo-3-(trifluoromethyl)phenyl]({4-[2-(N-ethylcarbamoyl)(4-pyridyloxy)]phenyl}amino)carboxamide |
| 89 | {[4-bromo-3-(trifluoromethyl)phenyl]amino}-N-{3-[2-(N-methylcarbamoyl)(4-pyridyloxy)]phenyl}carboxamide |
| 90 | {[4-bromo-3-(trifluoromethyl)phenyl]amino}-N-{4-methyl-3-[2-(N-methylcarbamoyl)(4-pyridyloxy)]phenyl}carboxamide |
| 93 | {[4-bromo-3-(trifluoromethyl)phenyl]amino}-N-{3-[2-(N-methylcarbamoyl)(4-pyridylthio)]phenyl}carboxamide |
| 94 | {4-[4-({[4-bromo-3-(trifluoromethyl)phenyl]amino}carbonylamino)phenoxy](2-pyridyl)}-N-(2-morpholin-4-ylethyl)carboxamide |
| 95 | N-[4-chloro-2-methoxy-5-(trifluoromethyl)phenyl]({4-[2-(N-methylcarbamoyl)(4-pyridyloxy)]phenyl}amino)carboxamide |
| 96 | N-[4-chloro-2-methoxy-5-(trifluoromethyl)phenyl]({2-chloro-4-[2-(N-methylcarbamoyl)(4-pyridyloxy)]phenyl}amino)carboxamide |
| 97 | N-[4-chloro-2-methoxy-5-(trifluoromethyl)phenyl]({3-chloro-4-[2-(N-methylcarbamoyl)(4-pyridyloxy)]phenyl}amino)carboxamide |
| 98 | N-[4-chloro-2-methoxy-5-(trifluoromethyl)phenyl]({3-[2-(N-methylcarbamoyl)(4-pyridyloxy)]phenyl}amino)carboxamide |
| 99 | N-[4-chloro-2-methoxy-5-(trifluoromethyl)phenyl]({4-[2-(N-ethylcarbamoyl)(4-pyridyloxy)]phenyl}amino)carboxamide |

From WO 2002/85859

| Entry No | Name |
|---|---|
| 16 | [(4-fluorophenyl)amino]-N-(3-isoquinolyl)carboxamide |
| 25 | N-(2-methoxy(3-quinolyl))[(4-(4-pyridyloxy)phenyl)amino]carboxamide |
| 27 | N-(2-methoxy(3-quinolyl))[(3-(4-pyridylthio)phenyl)amino]carboxamide |
| 28 | N-[1-(4-methylpiperazinyl)(3-isoquinolyl)][(4-(4-pyridyloxy)phenyl)amino]carboxamide |

From WO 2002/85857

| Entry No | Name |
|---|---|
| 25 | N-(2-methoxy(3-quinolyl))[(4-(4-pyridyloxy)phenyl)amino]carboxamide |
| 27 | N-(2-methoxy(3-quinolyl))[(3-(4-pyridylthio)phenyl)amino]carboxamide |
| 28 | N-[1-(4-methylpiperazinyl)(3-isoquinolyl)][(4-(4-pyridyloxy)phenyl)amino]carboxamide |

Cell Mechanistic Assay-Inhibition of 3T3 KDR Phosphorylation:

NIH3T3 cells expressing the full length KDR receptor are grown in DMEM (Life Technologies, Inc., Grand Island, N.Y.) supplemented with 10% newborn calf serum, low glucose, 25 mM/L sodium pyruvate, pyridoxine hydrochloride and 0.2 mg/ml of G418 (Life Technologies Inc., Grand Island, N.Y.). The cells are maintained in collagen I-coated T75 flasks (Becton Dickinson Labware, Bedford, Mass.) in a humidified 5% CO2 atmosphere at 37° C.

Fifteen thousand cells are plated into each well of a collagen I-coated 96-well plate in the DMEM growth medium. Six hours later, the cells are washed and the medium is replaced with DMEM without serum. After overnight culture to quiesce the cells, the medium is replaced by Dulbecco's phosphate-buffered saline (Life Technologies Inc., Grand Island, N.Y.) with 0.1% bovine albumin (Sigma Chemical Co., St. Louis, Mo.). After adding various concentrations (0-300 nM) of test compounds to the cells in 1% final concentration of DMSO, the cells are incubated at room temperature for 30 minutes. Following VEGF stimulation, the buffer is removed and the cells are lysed by addition of 150 µl of extraction buffer (50 mM Tris, pH 7.8, supplemented with 10% glycerol, 50 mM BGP, 2 mM EDTA, 10 mM NaF, 0.5 mM NaVO4, and 0.3% TX-100) at 4° C. for 30 minutes.

To assess receptor phosphorylation, 100 microliters of each cell lysate are added to the wells of an ELISA plate precoated with 300 ng of antibody C20 (Santa Cruz Biotechnology, Inc., Santa Cruz, Calif.). Following a 60-minute incubation, the plate is washed and bound KDR is probed for phosphotyrosine using an anti-phosphotyrosine mAb clone 4G10 (Upstate Biotechnology, Lake Placid, N.Y.). The plate is washed and wells are incubated with anti-mouse IgG/HRP conjugate (Amersharn International plc, Buckinghamshire, England) for 60 minutes. Wells are washed and phosphotyrosine is quantitated by addition of 100 µl per well of 3,3,5,5' tetramethylbenzidine (Kirkegaard and Perry, TMB 1 Component Stop Solution).

Optical densities (OD) are determined spectrophotometrically at 450 mm in a 96-well plate reader (SpectraMax 250, Molecular Devices). Background (no VEGF added) OD values are subtracted from all Ods and percent inhibition is calculated according to the equation:

$$\% \text{ Inhibition} = \frac{(OD(VEGF \text{ control}) - OD(\text{with test compound}) \times 100}{OD(VEGF \text{ control}) - OD(\text{no } VEGF \text{ added})}$$

$IC_{50S}$ are determined on some of the exemplary materials with at least squares analysis program using compound concentration versus percent inhibition.

Matrigel® Angiogenesis Model:

Preparation of Martigel Plugs and in vivo Phase: Matrigel® (Collaborative Biomedical Products, Bedord, Mass.) is a basement membrane extract from a murine tumor composed primarily of laminin, collagen IV and heparan sulfate proteoglycan. It is provided as a sterile liquid at 4° C., but rapidly forms a solid gel at 37° C.

Liquid Matrigel at 4° C. is mixed with SK-MEL2 human tumor cells that are transfected with a plasmid containing the murine VEGF gene with a selectable marker. Tumor cells are grown in vitro under selection and cells are mixed with cold liquid Matrigel at a ratio of 2×10⁶ per 0.5 ml. One half milliliter is implanted subcutaneously near the abdominal midline using a 25 gauge needle. Test compounds are dosed as solutions in Ethanol/Ceremaphor EL/saline (12.5%:12.5%:75%) at 30, 100, and 300 mg/kg po once daily starting on the day of implantation. Mice are euthanized 12 days post-implantation and the Matrigel pellets are harvested for analysis of hemoglobin content.

Hemoglobin Assay: The Matrigel pellets are placed in 4 volumes (w/v) of 4° C. Lysis Buffer (20 mM Tris pH 7.5, 1 mM EGTA, 1 mM EDTA, 1% Triton X-100 [EM Science, Gibbstown, N.J.], and complete EDTA-free protease inhibitor cocktail [Mannheim, Germany]), and homogenized at 4° C. homogenates are incubated on ice for 30 minutes with shaking and centrifuged at 14K×g for 30 minutes at 4° C. Supernatants are transferred to chilled microfuge tubes and stored at 4° C. for hemoglobin assay.

Mouse hemoglobin (Sigma Chemical Co., St. Louis, Mo.) is suspended in autoclaved water (BioWhittaker, Inc, Walkersville, Md.) at 5 mg/ml. A standard curve is generated from 500 micrograms/ml to 30 micrograms/ml in Lysis Buffer (see above). Standard curve and lysate samples are added at 5 microliters/well in duplicate to a polystyrene 96-well plate. Using the Sigma Plasma Hemoglobin Kit (Sigma Chemical Co., St. Louis, Mo.), TMB substrate is reconstituted in 50 mls room temperature acetic acid solution. One hundred microliters of substrate is added to each well, followed by 100 microliters/well of Hydrogen Peroxide Solution at room temperature. The plate is incubated at room temperature for 10 minutes.

Optical densities are determined spectrophotometrically at 600 nm in a 96-well plate reader, SpectraMax 250 Microplate Spectrophotometer System (Molecular Devices, Sunnyvale, Calif.). Background Lysis Buffer readings are subtracted from all wells.

Total sample hemoglobin content is calculated according to the following equation:

Total Hemoglobin=(Sample Lysate Volume)×(Hemoglobin Concentration)

The average Total Hemoglobin of Matrigel samples without cells is subtracted from each Total Hemoglobin Matrigel sample with cells. Percent inhibition is calculated according to the following equation:

$$\% \text{ Inhibition} = \frac{(\text{Average Total Hemoglobin Drug-Treated Tumor Lysates}) \times 100}{(\text{Average Total Hemoglobin Non-Treated } Tumore \text{ Lysates})}.$$

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

We claim:

1. A method of blocking tumor angiogenesis in a human or other mammal comprising administering to a human or other mammal with a tumor of the breast, gastrointestinal tract, kidney, ovary or cervix, an effective amount of the compound N-(4-chloro-3-(trifluoromethyl)phenyl)-N'-(4-(2-(N-methylcarbamoyl)-4-pyridyloxy)phenyl)urea of the formula below or a pharmaceutically acceptable salt thereof

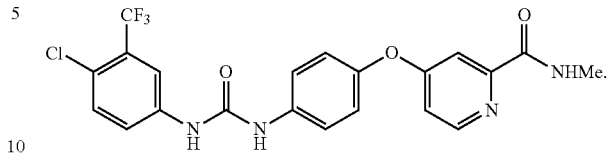

2. A method as in claim 1 wherein the compound N-(4-chloro-3-(trifluoromethyl)phenyl)-N'-(4-(2-(N-methylcarbamoyl)-4-pyridyloxy)phenyl)urea or a pharmaceutically acceptable salt thereof is administered simultaneously with another angiogenesis inhibiting agent to a human or other mammal with a tumor of the breast, gastrointestinal tract, kidney, ovary or cervix in the same formulation or in separate formulations.

3. A method as in claim 1 wherein the tumor that is treated is characterized by abnormal angiogenesis or hyperpermiability processes, which are mediated by KDR (VEGFR-2).

4. A method as in claim 1 wherein the tumor that is treated is characterized by abnormal angiogenesis or hyperpermiability processes, which are not raf-mediated.

5. A method as in claim 4 wherein the tumor that is treated is characterized by abnormal angiogenesis or hyperpermiability processes, which are not p38-mediated.

6. A method of blocking tumor angiogenesis in a human or other mammal comprising administering to a human or other mammal with a tumor of the breast, gastrointestinal tract, kidney, ovary or cervix, an effective amount of the compound N-(4-chloro-3-(trifluoromethyl)phenyl)-N'-(4-(2-(N-methylcarbamoyl)-4-pyridyloxy)phenyl)urea tosylate.

7. A method of blocking angiogenesis in a tumor of the kidney comprising administering to a human or other mammal with a tumor of the kidney an effective amount of the tosylate salt of N-(4-chloro-3-(trifluoromethyl)phenyl)-N'-(4-(2-(N-methylcarbamoyl)-4-pyridyloxy)phenyl)urea of the formula below

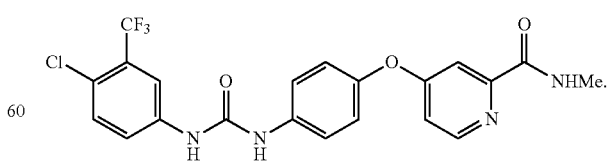

8. A method as in claim 7 wherein the tumor of the kidney that is treated is characterized by abnormal angiogenesis or hyperpermiability processes, which are not raf-mediated nor p38-mediated.

9. A method as in claim 8 wherein the tumor of the kidney that is treated is characterized by abnormal angiogenesis or hyperpermiability processes, which are mediated by KDR (VEGFR-2).

10. The method of claim 6, wherein the effective amount of the compound N-(4-chloro-3-(trifluoromethyl)phenyl)-N'-(4-(2-(N-methylcarbamoyl)-4-pyridyloxy)phenyl)urea tosylate is between 0.01 to 200 mg/Kg of total body weight.

11. The method of claim 7, wherein the effective amount of the compound N-(4-chloro-3-(trifluoromethyl)phenyl)-N'-(4-(2-(N-methylcarbamoyl)-4-pyridyloxy)phenyl)urea of the formula below is between 0.01 to 200 mg/Kg of total body weight

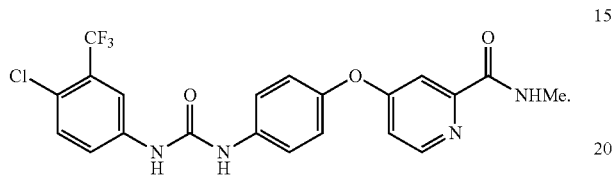

* * * * *